United States Patent
Ohkuchi et al.

(10) Patent No.: US 6,403,586 B1
(45) Date of Patent: Jun. 11, 2002

(54) PYRIDAZINE DERIVATIVES AND DRUGS CONTAINING THE SAME AS THE ACTIVE INGREDIENT

(75) Inventors: Masao Ohkuchi, Tokorozawa; Yoshinori Kyotani, Higashiyamato; Hiromichi Shigyo, Fuchu; Hideo Yoshizaki, Sayama; Tomoyuki Koshi, Shiki; Takahiro Kitamura, Higashimurayama; Takayuki Matsuda, Higashimurayama; Soichi Oda, Higashimurayama; Yuriko Habata, Higashiyamato; Kyoko Kotaki, Sakado, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/622,897

(22) PCT Filed: Feb. 26, 1999

(86) PCT No.: PCT/JP99/00925

§ 371 (c)(1), (2), (4) Date: Aug. 31, 2000

(87) PCT Pub. No.: WO99/44995

PCT Pub. Date: Sep. 10, 1999

(30) Foreign Application Priority Data

Mar. 2, 1998 (JP) .............................. 10-049396

(51) Int. Cl.$^7$ ...................... A61K 31/50; A61K 31/501; C07D 237/22; C07D 237/24; C07D 401/06
(52) U.S. Cl. .................. 514/247; 514/252.03; 544/238; 544/239
(58) Field of Search .................. 544/238, 239; 514/247, 252.03

(56) References Cited

U.S. PATENT DOCUMENTS 4,954,518 A    9/1990   Takano et al. .............. 514/456

FOREIGN PATENT DOCUMENTS

| EP | 537696 | 4/1993 |
| EP | 628550 | 12/1994 |
| JP | 5-221992 | 8/1993 |
| JP | 7-69894 | 3/1995 |
| WO | WO 98/41511 | 9/1998 |
| WO | WO 99/10331 | 3/1999 |
| WO | WO 99/10332 | 3/1999 |
| WO | WO 00/24719 | 5/2000 |

OTHER PUBLICATIONS

Livingston, *Journal of Cellular Biochemistry* 64 p. 19–26, 1997.*
C. Coudert, et al., Eur. J. Med. Chem., vol. 29, No. 6, pp. 471–477, "Synthesis of Pyridazine Acetic Acid Derivatives Possessing Aldose Reductase Inhibitory Activity and Antioxidant Properties", 1994.
Abstract for WO 00/50408 (Feb. 25, 2000).

* cited by examiner

*Primary Examiner*—Emily Bernhardt
(74) *Attorney, Agent, or Firm*—Oblon, Spivak, McClelland, Maier & Neustadt, P.C.

(57) ABSTRACT

This invention relates to pyridazine derivatives represented by the formula (1):

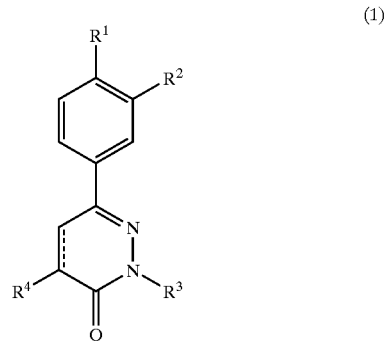

wherein $R^1$ represents a lower alkoxyl group, a lower alkylthio group or a halogen atom; $R^2$ represents H, a lower alkoxyl group, a lower alkylthio group or a halogen atom; $R^3$ represents a lower alkyl or lower alkenyl group, which may be substituted by one or more OHs, CNs, lower cycloalkyl groups, (substituted) aromatic groups or (substituted) carbamoyl groups; $R^4$ represents COOH, a lower alkoxycarbonyl group, a (substituted) carbamoyl group, a (substituted) amino group, or a (substituted) ureido group; and the dashed line indicates that the carbon-carbon bond between the 4-position and the 5-position is a single bond or a double bond, or salts thereof; and also to medicines containing them as effective ingredients. These compounds have excellent inhibitory activity against interleukin-1β production, and are useful as preventives and therapeutics for immune system diseases, inflammatory diseases, ischemic diseases and the like.

9 Claims, No Drawings

PYRIDAZINE DERIVATIVES AND DRUGS CONTAINING THE SAME AS THE ACTIVE INGREDIENT

TECHNICAL FIELD

This invention relates to novel pyridazine derivatives, which have excellent inhibitory activity against interleukin-1β production and are useful for the prevention and treatment of immune system diseases, inflammatory diseases, ischemic diseases and the like, and also to medicines containing them as effective ingredients.

BACKGROUND ART

In many diseases, for example, rheumatism, arthritis, osteoporosis, inflammatory colitis, immune deficiency syndrome, ichorrhemia, hepatitis, nephritis, ischemic diseases, insulin-dependent diabetes mellitus, arterial sclerosis, Parkinson's disease, Alzheimer's disease, leukemia and the like, stimulation of interleukin-1β production, an inflammatory cytokine, is observed. This interleukin-1β serves to induce synthesis of an enzyme which is considered to take part in inflammation like collagenase and PLA2 and, when intra-articularly injected to animals, causes multiarticular destruction highly resembling rheumatoid arthritis. On the other hand, interleukin-1β is controlled in activity by interleukin-1β receptor, soluble interleukin-1 receptor and interleukin-1 receptor antagonist.

From research conducted making use of recombinants of these bioactivity-inhibiting substances, anti-interleukin-1β antibodies and anti-receptor antibodies against various disease models, interleukin-1β has been found to play an important role in the body, leading to an increasing potential of substances having interleukin-1β inhibitory activity as therapeutics for such diseases.

For example, immunosuppressors and steroids which are used for the treatment of rheumatism out of such many diseases have been reported to inhibit the production of interleukin-1β. Even among medicaments currently under development, KE298, a benzoylpropionic acid derivative [The Japanese Society of Inflammation (11th), 1990], for example, has been reported to have inhibitory activity against interleukin-1β production although it is an immunoregulator. Inhibitory activity against interleukin-1β production is also observed on a group of compounds which are called "COX-2 selective inhibitors", for example, nimesulide as a phenoxysulfonanilide derivative (DE 2333643), T-614 as a phenoxybenzopyran derivative (U.S. Pat. No. 4,954, 518), and tenidap (hydroxyindole derivative) as a dual inhibitor (COX-1/5-LO).

For all of these compounds, however, interleukin-1β production inhibitory activity is not their primary action so that their inhibitory activity against interleukin-1β production is lower than their primary action.

In recent years, increasingly active research is under way for the synthesis of compounds with a focus placed on inhibitory activity against interleukin-1β production. Inhibitors synthesized in such research can be classified into a group of compounds which inhibit the transfer process of an inflammatory signal to a cell nucleus and another group of compounds which inhibit an enzyme ICE that functions in the processing of a precursor of interleukin-1β Known examples of compounds presumed to have the former action include SB203580 [Japanese Language Laid-Open (Kokai) Publication (PCT) No. HEI 7-503017], FR167653 (Eur. J. Pharm., 327, 169–175, 1997), E-5090 (EP 376288), CGP47969A (Gastroenterology, 109, 812–828, 1995), hydroxyindole derivatives (Eur. J. Med. Chem. 31, 187–198, 1996), and triarylpyrrole derivatives (WO 97/05878), while known examples of compounds presumed to have the latter action include VE-13,045 which is a peptide compound (Cytokine, 8(5), 377–386, 1996).

None of these compounds can however exhibit sufficient inhibitory activity against interleukin-1β production.

On the other hand, it is known that a variety of 5,6-diphenylpyridazine derivatives have analgesic and anti-inflammatory action (EUR. J. MED. CHEM., 14, 53–60, 1979) and also that 3,4,5,6-substituted pyridazine derivatives have inhibitory activity against interleukin-1β converting enzymes [Japanese Patent Application Laid-Open (Kokai) No. HEI 7-69894]. Absolutely nothing has however been known with respect to inhibitory activity of 2,4,6-substituted pyridazin-3-one derivatives against interleukin-1β production.

Accordingly, an object of the present invention is to provide a compound having excellent inhibitory activity against interleukin-1β production and also a medicine containing it as an effective ingredient.

DISCLOSURE OF THE INVENTION

Under such circumstances, the present inventors have proceeded with an extensive investigation. As a result, it has been found that pyridazine derivatives represented by the below-described formula (1) have excellent inhibitory activity against interleukin-1β production and are useful for the prevention and treatment of immune system diseases, inflammatory diseases, ischemic diseases and the like, leading to the completion of the present invention.

Namely, the present invention provides a pyridazine derivative represented by the following formula (1):

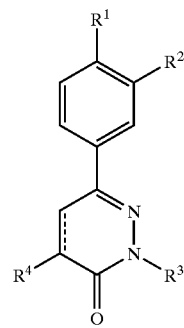

(1)

wherein $R^1$ represents a lower alkoxyl group, a lower alkylthio group or a halogen atom; $R^2$ represents a hydrogen atom, a lower alkoxyl group, a lower alkylthio group or a halogen atom; $R^3$ represents a linear or branched lower alkyl or lower alkenyl group, which may have one or more substituents each independently selected from a hydroxyl group, a halogen atom, a cyano group, a lower cycloalkyl group, a substituted or unsubstituted aromatic group or a substituted or unsubstituted carbamoyl group; $R^4$ represents a carboxyl group, a lower alkoxycarbonyl group, a substituted or unsubstituted thiocarbamoyl group, a substituted or unsubstituted amino group, or a substituted or unsubstituted ureido group; and the dashed line indicates that the carbon-carbon bond between the 4-position and the 5-position is a single bond or a double bond; or a salt thereof.

Further, the present invention also provides a medicine comprising the pyridazine derivative (1) or the salt thereof as an effective ingredient.

Furthermore, the present invention also provides a pharmaceutical composition comprising the pyridazine derivative (1) or the salt thereof and a pharmaceutically acceptable carrier.

Moreover, the present invention also provides use of the pyridazine derivative (1) or the salt thereof as a medicine.

In addition, the present invention also provides a method for treating a disease caused by stimulation of interleukin-1β production, which comprises administering the pyridazine derivative (1) or the salt thereof.

BEST MODE FOR CARRYING OUT THE INVENTION

The pyridazine derivative according to the present invention is represented by the formula (1). In the formula, illustrative of the lower alkoxyl groups represented by $R^1$ and $R^2$ can be those having 1 to 6 carbon atoms, for example, methoxy, ethoxy and propoxy. Illustrative of the lower alkylthio groups can be those having 1 to 6 carbon atoms, for example, methylthio, ethylthio and propylthio. Illustrative of the halogen atoms can be fluorine, chlorine, bromine and iodine.

Preferred as $R^1$ is a fluorine atom, a lower alkoxyl group or a lower alkylthio group, while preferred as $R^2$ is a hydrogen atom, a halogen atom or a lower alkoxyl group.

Examples of the lower alkyl group out of those represented by $R^3$ can include linear or branched lower alkyl groups having 1 to 6 carbon atoms, for example, methyl, ethyl, n-propyl, isopropyl and n-butyl. Examples of the lower alkenyl group can include linear or branched lower alkenyl groups having 2 to 9 carbon atoms, more preferably 2 to 6 carbon atoms and 1 to 3 double bonds, for example, ethenyl, propenyl and butenyl.

These lower alkyl groups and lower alkenyl groups may have one or more substituents each independently selected from a hydroxyl group, a halogen atom, a cyano group, a lower cycloalkyl group, a substituted or unsubstituted aromatic group, or a substituted or unsubstituted carbamoyl group.

Examples of the lower cycloalkyl group can include those having 3 to 8 carbon atoms, for example, cyclopropyl, cyclobutyl, cyclopentyl and cyclohexyl.

Examples of the aromatic group can include aromatic hydrocarbon groups and aromatic heterocyclic groups, for example, phenyl, naphthyl and pyridyl, with phenyl and pyridyl being particularly preferred. These aromatic groups may each contain 1 to 3 substituents. Examples of such substituents can include halogens, nitro, amino, and aromatic-group-substituted carbonylamino groups. Illustrative of aromatic group(s) substituted on the carbonylamino group can be phenyl and pyridyl.

Illustrative of substituent(s) which the carbamoyl group may have can be lower alkyl groups, lower alkyl groups each of which may be substituted by one or more hydroxyl groups or aromatic groups, and aromatic groups each of which may be substituted by one or more lower alkylthio groups.

Further, examples of the halogen atoms, aromatic groups, lower alkyl groups and lower alkylthio groups can be similar ones as those exemplified above (including those exemplified as $R^1$ and $R^2$).

$R^3$ may preferably be an alkyl group having 1 to 6 carbon atoms or a lower alkenyl group having 2 to 9 carbon atoms, which may have one or more substituents each independently selected from a hydroxyl group, a halogen atom, a cyano group or a lower cycloalkyl group; a phenyl or pyridyl group which may have 1 to 3 substituents each independently selected from a halogen atom, a nitro group, an amino group or an aromatic-group-substituted carbonylamino group; or a carbamoyl group which may have one or more substituents each independently selected from a lower alkyl groups, hydroxy lower alkyl group, an aromatic-group-substituted lower alkyl group or a lower alkylthiophenyl group.

Examples of the lower alkoxycarbonyl group out of those represented by $R^4$ can include carbonyl groups each of which has an alkoxyl group having 1 to 6 carbon atoms, for example, methoxycarbonyl, ethoxycarbonyl and butoxycarbonyl.

Examples of the substituent(s) in the substituted carbamoyl or thiocarbamoyl group can include lower alkyl groups, which may have one or more substituents such as aromatic groups, and aromatic groups.

Examples of the substituent(s) in the substituted amino group can include lower alkoxycarbonyl groups each of which may have one or more substituents such as aromatic groups; acyl groups; lower alkyl groups each of which may have one or more substituents such as aromatic groups; and lower alkylsulfonyl groups. Illustrative of the acyl groups can be those having 1–5 carbon atoms, for example, formyl, acetyl, propionyl and butyryl.

Examples of the substituent(s) in the substituted ureido group can include lower alkyl groups.

Incidentally, specific examples of the individual groups, such as the lower alkyl group, aromatic group and lower alkoxyl group, represented by $R^4$ can be similar to those exemplified above with respect to $R^1$, $R^2$ and $R^3$.

$R^4$ may preferably be a carboxyl group; a lower alkoxycarbonyl group; a carbamoyl or thiocarbamoyl group which may have one or more substituents each independently selected from a lower alkyl group, an aromatic group or an aromatic-group-substituted lower alkyl group; an amino group which may have one or more substituents each independently selected from a lower alkoxycarbonyl group, an aromatic-group-substituted lower alkoxycarbonyl group, an acyl group, a lower alkyl group, an aromatic-group-substituted lower alkyl group or a lower alkylsulfonyl group; or a ureido group which may have one or more lower alkyl groups as substituents.

Further, the dashed line in the formula (1), namely, the carbon-carbon bond between the 4-position and the 5-position may preferably be a double bond.

Preferred examples of the pyridazine derivative (1) can include those represented by the same formula in which $R^1$ represents a fluorine atom, a lower alkoxyl group or a lower alkylthio group; $R^2$ represents a hydrogen atom, a halogen atom or a lower alkoxyl group; $R^3$ represents a linear or branched lower alkyl group having 1 to 6 carbon atoms or a linear or branched lower alkenyl group having 2 to 9 carbon atoms, which may have one or more substitutents each independently selected from a hydroxyl group, a halogen atom, a cyano group, a lower cycloalkyl group; a phenyl or pyridyl group which may have 1 to 3 substituents each independently selected from a halogen atom, a nitro group, an amino group or an aromatic-group-substituted carbonylamino group; or a carbamoyl group which may be have one or more substituents each independently selected from a lower alkyl group, a hydroxy lower alkyl group, an aromatic-group-substituted lower alkyl group or a lower alkylthiophenyl group; and $R^4$ represents a carboxyl group; a lower alkoxycarbonyl group; a carbamoyl or thiocarbamoyl group which may have one or more substituents each independently selected from a lower alkyl group, an aromatic group or an aromatic-group-substituted lower alkyl group; an amino group which may be have one or more substitutents each independently selected from a lower alkoxycarbonyl group, an aromatic-group-substituted lower alkoxycarbonyl group, an acyl group, a lower alkyl groups, an aromatic-group-substituted lower alkyl group or a lower alkylsulfonyl group; or a ureido group which may have one or more lower alkyl groups as substituents.

Specific preferred examples can include 2-isobutyl-6-(4-methoxyphenyl)-4-methylcarbamoyl-2H-pyridazin-3-one, 2-(cyclopropylmethyl)-6-(4-methoxyphenyl)-4-methylcarbamoyl-2H-pyridazin-3-one, 2-(cyclopropylmethyl)-6-(3-fluoro-4-methoxyphenyl)-4-methylcarbamoyl-2H-pyridazin-3-one, 2-(cyclopropylmethyl)-4-ethylcarbamoyl-6-(4-methoxyphenyl)-2H-pyridazin-3-one, 2-(4-chlorocinnamyl)-4-ethoxycarbonylamino-6-(4-methoxyphenyl)-2H-pyridazin-3-one, or 2-(4-chlorocinnamyl)-4-formylamino-6-(4-methoxyphenyl)-2H-pyridazin-3-one.

No particular limitation is imposed on the salt of the pyridazine (1), said salt also pertaining to the present invention, insofar as it is a pharmacologically acceptable salt. Illustrative can be acid addition salts of mineral acids, such as the hydrochloride, hydrobromide, hydroiodide, sulfate, nitrate and phosphate; and acid addition salts of organic acids, such as the benzoate, methanesulfonate, ethanesulfonate, benzenesulfonate, p-toluenesulfonate, oxalate, maleate, fumarate, tartrate and citrate.

Further, the compounds according to the present invention may exist in the form of solvates represented by hydrates and also in the form of keto-enol tautomers. Such solvates and isomers should also be encompassed by the present invention.

The pyridazine derivatives (1) according to the present invention can be prepared, for example, by the following processes.

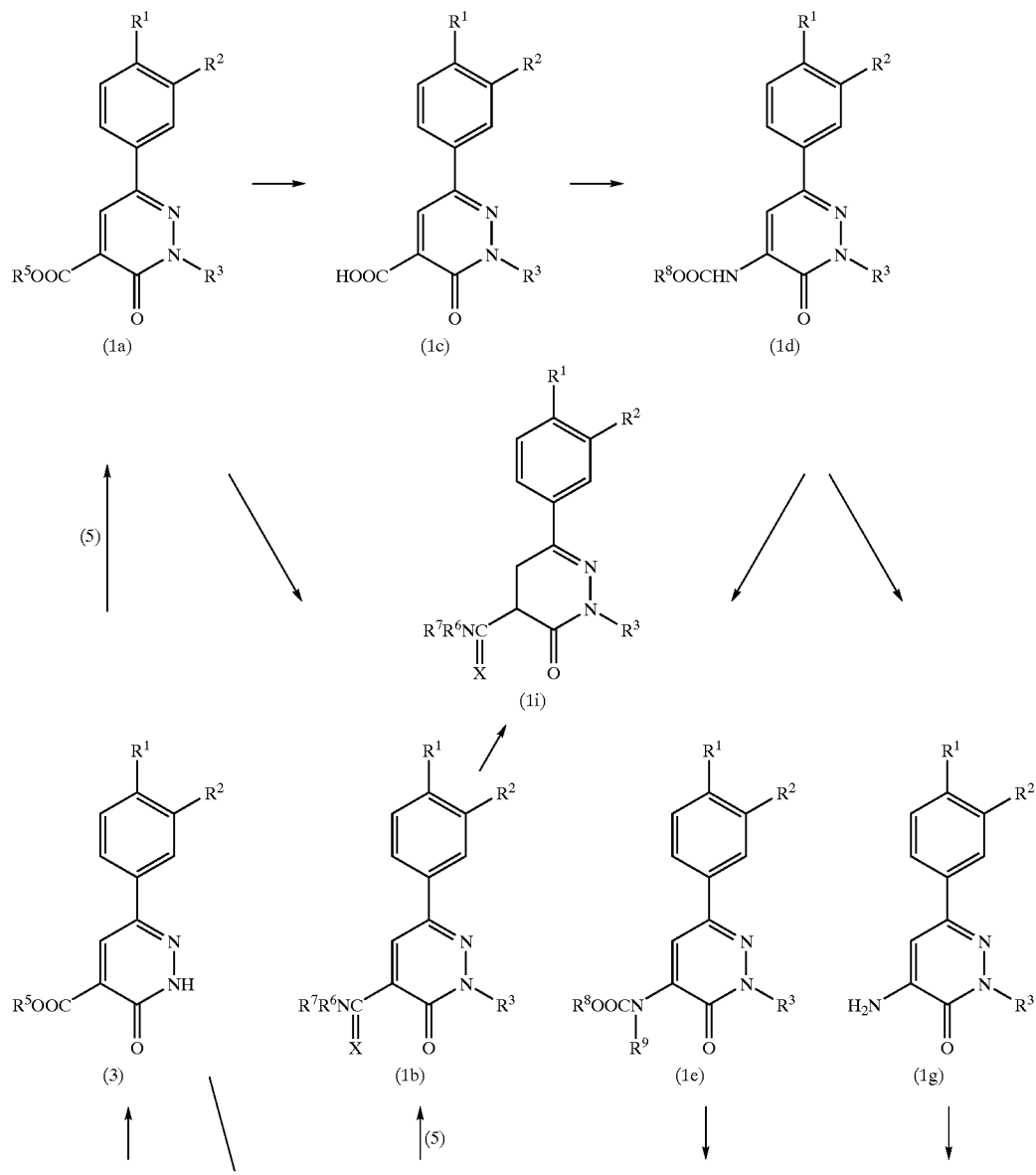

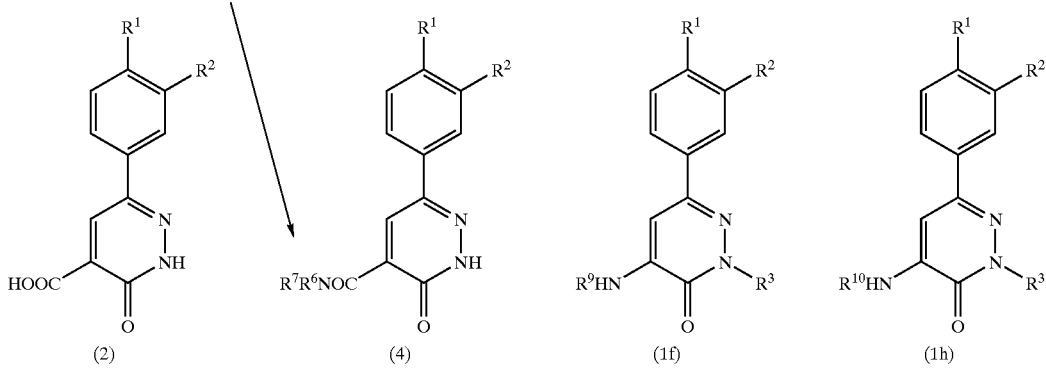

wherein $R^5$ represents a lower alkyl group, $R^6$ and $R^7$ each independently represent a hydrogen atom, a substituted or unsubstituted lower alkyl group or an aromatic group, $R^8$ represents a substituted or unsubstituted lower alkyl group, $R^9$ represents a substituted or unsubstituted lower alkyl group, $R^{10}$ represents an acyl group, a lower alkylsulfonyl, or a substituted or unsubstituted carbamoyl group, X represents an oxygen atom or a sulfur atom, and $R^1$, $R^2$ and $R^3$ have the same meanings as defined above.

A description will be made specifically about respective preparation processes of compounds (1a), (1b), (1c), (1d), (1e), (1f), (1g), (1h) and (1i) among the pyridazine derivatives (1).

(1) Preparation of compounds (1a) of the formula (1) in which $R^4$ is a lower alkoxycarbonyl group and a double bond is formed between the 4-position and the 5-position:

Each compound (1a) can be obtained by reacting a compound (3), which has been obtained by esterifying a compound (2) by a method known per se in the art, with a compound (5), which is represented by $R^3$-Y wherein $R^3$ has the same meaning as defined above and Y represents a halogen atom or an OH group already converted into a reactive ester group, in the presence of a base in a solvent.

The compound (2) employed here can be prepared, for example, by the process disclosed in Japanese Patent Application Laid-Open (Kokai) No. HEI 7-69891.

As the reactive ester group of the hydroxyl group, a tosyloxy group, a mesyloxy group, a benzenesulfonyloxy group or the like is preferred. A compound which contains such a group can be obtained by reacting para-toluenesulfonyl chloride, methanesulfonyl chloride, methanesulfonic anhydride, benzenesulfonyl chloride or the like with a hydroxyl derivative in the presence of a base such as pyridine, triethylamine or collidine. The reaction is brought to completion at −15 to 50° C. in 1 to 50 hours, preferably at −5 to 30° C. in 1 to 10 hours. As a solvent, pyridine, tetrahydrofuran, diethyl ether, ethyl acetate, methylene chloride, chloroform, N,N-dimethylformamide, dimethyl sulfoxide or the like can be used.

Examples of the base for use in the reaction between the compound (3) and the compound (5) can include inorganic bases such as potassium carbonate and sodium carbonate and organic bases such as pyridine, triethylamine, and 1,8-diazabicyclo[5.4.0]undeca-7-ene (DBU). Usable examples of the solvent can include N,N-dimethylformamide, dimethylsulfoxide, acetone, methyl ethyl ketone, chloroform, methylene chloride, toluene, and benzene. The reaction is brought to completion at 20 to 150° C. in 1 to 20 hours, preferably at 50 to 130° C. Among the compounds (1a), one containing an aminophenylalkyl group as $R^3$ can be obtained by reducing the nitro group of a compound (1a) in which $R^3$ is a nitrophenylalkyl group. Further, N-acylation of the aminophenylalkyl group makes it possible to obtain a compound in which $R^3$ is an N-acylaminophenylalkyl group.

(2) Preparation of compounds (1b) of the formula (1) in which $R^4$ is a substituted or unsubstituted carbamoyl group and a double bond is formed between the 4-position and the 5-position:

Each compound (1b) can be obtained by reacting in a solvent the compound (3) with an amine, which is represented by $R^6R^7NH_2$ in which $R^6$ and $R^7$ have the same meanings as defined above, to give the compound (4), followed by reacting it as a raw material in a similar manner as in the reaction between the compound (3) and the compound (5). In the reaction between the compound (3) and the amine, it is preferable to use the amine in an amount of from 1 to 30 equivalents, especially from 2 to 15 equivalents relative to the compound (3). Usable examples of the solvent can include methanol, ethanol, isopropanol, tetrahydrofuran, and N,N-dimethylformamide. The reaction is brought to completion at −10 to 200° C. in 0.5 to 24 hours, preferably at 20 to 150° C. in 0.5 to 3 hours.

On the other hand, the reaction between the compound (4) and the compound (5) is brought to completion at 20 to 150° C. in 1 to 20 hours, preferably at 50 to 130° C. in 2 to 10 hours.

Among the compounds (1b), one containing an arylalkylcarbamoylalkyl group or a hydroxyalkylcarbamoylalkyl group as $R^3$ can be obtained by reacting an arylalkylamine or a hydroxyalkylamine with a compound (1b) in which $R^3$ is an alkoxycarbonylalkyl group.

Each of the compounds (1b) can also be obtained by reacting the compound (1a) as a raw material in a similar manner as in the reaction conducted upon conversion of the compound (3) into the compound (4).

(3) Preparation of compounds (1i) of the formula (1) in which $R^4$ is a substituted or unsubstituted carbamoyl group and a single bond is formed between the 4-position and the 5-position:

Each compound (1i) can be obtained by subjecting the compound (1b) to catalytic reduction in a manner known per se in the art. The reaction can be conducted by effecting hydrogenation at room temperature or under heating in the presence of palladium on charcoal, Raney nickel or the like as a catalyst in a solvent such as methanol, ethanol or ethyl acetate.

(4) Preparation of compounds (1c) of the formula (1) in which $R^4$ is a carboxyl group and a double bond is formed between the 4-position and the 5-position:

Each compound (1c) can be obtained by hydrolyzing the compound (1a) under acidic or basic conditions in a solvent by a method known per se in the art.

Examples of an acid can include hydrochloric acid, sulfuric acid and trifluoroacetic acid, while examples of a base can include sodium hydroxide, potassium hydroxide and barium hydroxide. Usable examples of the solvent can include mixed solvents of water with methanol, ethanol, isopropanol, tetrahydrofuran, N,N-dimethylformamide and the like. The reaction is brought to completion at 0 to 150° C. in 10 minutes to 5 hours, preferably at 20 to 100° C. in 30 minutes to 2 hours.

(5) Preparation of compounds (1d) of the formula (1) in which $R^4$ is a substituted or unsubstituted alkoxycarbonylamino group and a double bond is formed between the 4-position and the 5-position:

Each compound (1d) can be obtained by reacting a compound (1c) with an alcohol, which is represented by $R^8OH$ in which $R^8$ has the same meaning as defined above, and diphenylphosphoryl azide (DPPA) in the presence of a base in a solventless manner or in a solvent.

Examples of the solvent can include benzene and toluene. Usable examples of the base can include triethylamine. The reaction is brought to completion at 50 to 150° C. in 0.5 to 24 hours, preferably at 80 to 120° C. in 1 to 8 hours.

(6) Preparation of compounds (1e) of the formula (1) in which $R^4$ is an amino group substituted by a substituted or unsubstituted lower alkyl group and a lower alkoxycarbonyl group and a double bond is formed between the 4-position and the 5-position:

Each compound (1e) can be obtained by reacting a compound (1d) with a compound, which is represented by $R^9$-Y wherein $R^9$ and Y have the same meanings as defined above, in the presence of a base in a solvent. The reaction can be conducted in a similar manner as the above-described reaction between the compound (3) and the compound (5).

(7) Preparation of compounds (1f) of the formula (1) in which $R^4$ is an amino group substituted by a substituted or unsubstituted lower alkyl group and a double bond is formed between the 4-position and the 5-position:

Each compound (1f) can be obtained by hydrolyzing a compound (1e) under acidic or basic conditions in a solvent by a method known per se in the art Examples of an acid can include hydrochloric acid and sulfuric acid, while examples of a base can include sodium hydroxide, potassium hydroxide and barium hydroxide. Usable examples of the solvent can include mixed solvents of water with methanol, ethanol, isopropanol, tetrahydrofuran, N,N-dimethylformamide and the like. The reaction is brought to completion at 0 to 180° C. in 10 minutes to 24 hours, preferably at 20 to 120° C. in 0.5 to 8 hours.

(8) Preparation of compounds (1g) of the formula (1) in which $R^4$ is an amino group and a double bond is formed between the 4-position and the 5-position:

Each compound (1g) can be obtained by hydrolyzing the compound (1d) under acidic or basic conditions in a solvent by a method known per se in the art.

Examples of an acid can include hydrochloric acid and sulfuric acid, while examples of a base can include sodium hydroxide, potassium hydroxide and barium hydroxide. Usable examples of the solvent can include mixed solvents of water with methanol, ethanol, isopropanol, tetrahydrofuran, N,N-dimethylformamide and the like. The reaction is brought to completion at 0 to 180° C. in 10 minutes to 24 hours, preferably at 2 to 120° C. in 0.5 to 8 hours.

(9) Preperation of compounds (1h) of the formula (1) in which $R^4$ is an acylamino group, a lower alkylsulfonylamino group or a substituted or unsubstituted ureido group and a double bond is formed between the 4-position and the 5-position:

(i) Each compound (1h) in which $R^4$ is an acylamino group can be obtained by reacting a compound (1g) with a compound, which is represented by $R^{11}COX$ or $(R^{11}CO)_2O$ wherein $R^{11}$ represents a lower alkyl group, an aryl group or a lower aralkyl group and X represents a halogen atom, in the presence of a base in a solvent.

Examples of the solvent can include pyridine, tetrahydrofuran, dioxane, ethyl acetate, chloroform, toluene and benzene. It is also possible to use a mixed solvent of water and ethyl acetate, chloroform, toluene, benzene or the like. Usable examples of the base can include organic bases such as pyridine, triethylamine and DBU and inorganic bases such as sodium hydroxide, potassium hydroxide, potassium carbonate and sodium carbonate. The reaction is brought to completion at −15 to 100° C. in 1 to 50 hours, preferably at −5 to 50° C. in 2 to 25 hours.

(ii) Each compound (1h) in which $R^4$ is a lower alkylsulfonylamino group can be obtained by reacting, in a solvent and in the presence of a base, the compound (1g) with 2 equivalents or more of a compound, which is represented by $R^{11}SO_2X$ or $(R^{11}SO_2)_2O$ wherein $R^{11}$ and X have the same meanings as defined above in a similar manner as in the process (i), to give a di(lower alkylsulfonyl)amino derivative, followed by hydrolyzing it under basic conditions in a solvent.

Examples of the solvent for use in the hydrolysis can include mixed solvents of water and methanol, ethanol, isopropanol, tetrahydrofuran, N,N-dimethylformamide and the like. Usable examples of the base can include organic bases such as pyridine and inorganic bases such as sodium hydroxide, potassium hydroxide, potassium carbonate and sodium carbonate. The reaction is brought to completion at −15 to 100° C. in 10 minutes to 10 hours, preferably at 0 to 80° C. in 0.5 to 5 hours.

(iii) Each compound (1h) in which $R^4$ is a substituted or unsubstituted ureido group can be obtained by reacting the compound (1g) with a compound, which is represented by $R^{11}NCO$ wherein $R^{11}$ has the same meaning as defined above, in a solvent.

Usable examples of the solvent can include toluene and benzene. The reaction is brought to completion at 20 to 150° C. in 0.5 to 30 hours, preferably at 50 to 120° C. in 1 to 8 hours.

(10) Compounds (1b) or compounds (1i) of the formula (1) in each of which $R^4$ is a substituted or unsubstituted thiocarbamoyl group can each be obtained by converting X of the compound (1b) or the compound (1i), in which X is an oxygen atom, into a sulfur atom. For example, X in the compound (1b) in which X is an oxygen atom can be converted into a sulfur atom by reacting the compound (1b) with Lawesson's reagent [2,4-bis(4-methoxyphenyl)-1,3-dithia-2,4-diphosphetane-2,4-disulfide) in a solvent. It is preferred to use Lawesson's reagent in 0.5 to 3 equivalents, notably 1 to 1.5 equivalents relative to the compound (1b). The reaction is brought to completion at 30 to 150° C. in 1 to 20 hours, preferably at 50 to 100° C. in 5 to 15 hours. Usable examples of the solvent can include toluene and xylene.

(11) Preparation of compounds (1i) of the formula (1) in which $R^4$ is a substituted or unsubstituted carbamoyl group or thiocarbamoyl group and a single bond is formed between the 4-position and the 5-position:

Each compound (1i) can be prepared by hydrogenating the compound (1b), in which $R^4$ is a substituted or unsubstituted carbamoyl group or thiocarbamoyl group, in a solvent in the presence of palladium on charcoal or the like as a catalyst. Usable examples of the solvent can include methanol, ethanol, isopropanol, tetrahydrofuran, ethyl acetate, and N,N-dimethylformamide. The reaction is brought to completion at 15 to 200° C. in 1 to 50 hours, preferably at 50 to 120° C. in 2 to 20 hours.

The intermediates and target compounds obtained in the above-described individual reactions can be separated and purified by purification methods commonly employed in organic synthesis chemistry, for example, by subjecting them to filtration, extraction, washing, drying, concentration, recrystallization, various chromatographic treatment, and the like. The intermediates may be provided for the next reactions without purifying them specifically. Further, they may also be obtained as solvates of solvents such as reaction solvents or recrystallization solvents, especially as hydrates.

The pyridazine derivatives (1) and their salts according to the present invention, which are available as described above, have excellent inhibitory activity against interleukin-1β production, and are useful for the prevention and treatment of diseases caused by stimulation of interleukin-1β production, for example, immune system diseases, inflammatory diseases, ischemic diseases, osteoporisis, ichorrhemia and the like, especially as medicines such as preventives and therapeutics for rheumatism, immune deficiency syndrome, arthritis, inflammatory colitis, ischemic heart diseases, ischemic encephalopathy, ischemic nephritis, ischemic hepatitis, insulin-dependent diabetes mellitus, arterial sclerosis, Parkinson's disease, Alzheimer's disease, leukemia and the like or as interleukin-1β production inhibitors.

Medicines according to the present invention contain the pyridazine derivatives (1) or their salts as effective ingredients. Their administration routes can include, for example, oral administration by tablets, capsules, granules, powders, syrups or the like and parenteral administration by intravenous injections, intramuscular injections, suppositories, inhalants, transdermal preparations, eye drops, nasal drops or the like. Upon formulation of pharmaceutical compositions of these various unit dosage forms, the effective ingredients can be used singly or in combination with pharmaceutically acceptable carriers, for example, excipients, binders, extenders, disintegrators, surfactants, lubricants, dispersants, buffers, preservatives, corrigents, perfumes, coating agents, vehicles, diluents or the like, as desired.

The dosage of each medicine according to the present invention varies depending on the age, body weight, conditions, administration form, administration frequency and the like. In general, however, it is preferred to orally or parenterally administer to an adult the effective ingredient in an amount of about 0.01 to 1,000 mg, preferably 0.1 to 100 mg per day at once or in several portions.

EXAMPLES

The present invention will next be described in further detail by the following Examples. It should however be borne in mind that the present invention is not limited to these Examples.

Example 1

Preparation of 4-Methoxycarbonyl-6-(4-methoxyphenyl)-2-methyl-2H-pyridazin-3-one Potassium carbonate (346 mg, 2.50 mmol) and methyl iodide (284 mg, 2.00 mmol) were added to a solution of 4-methoxycarbonyl-6-(4-methoxyphenyl)-2H-pyridazin-3-one (260 mg, 1.00 mmol) in N,N-dimethylformamide (5 ml), followed by stirring at 60° C. for 2 hours. Inorganic matter was filtered off, the solvent was distilled off under reduced pressure, and the residue was then separated and purified by chromatography on a silica gel column [silica gel: 20 g, ethyl acetate/hexane (2/1)]. Crystallization was conducted from chloroform-hexane, whereby the title compound (233 mg, 85.0%) was obtained as yellow needles.

Melting point: 109.2–109.5° C.; $^1$H-NMR (CDCl$_3$) δ: 3.87(3H,s), 3.92(3H,s), 3.97(3H,s), 6.99(2H,d,J=8.9 Hz), 7.75(2H,d,J=8.9 Hz), 8.23(1H,s). IR (KBr) cm$^{-1}$: 1743, 1713,1660,1607,1518,1278,1250,1141, 1120,1101,839. Mass (m/z): 274 (M$^+$).

Example 2

Preparation of 2-Ethyl-4-methoxycarbonyl-6-(4-methoxyphenyl)-2H-pyridazin-3-one

Using 4-methoxycarbonyl-6-(4-methoxyphenyl)-2H-pyridazin-3-one and ethyl iodide as starting materials, the procedures of Example 1 were repeated likewise, whereby the title compound was obtained in a yield of 79.4%.

Pale yellow needles (chloroform-hexane); Melting point: 76.5–77.6° C.; $^1$H-NMR (CDCl$_3$) δ: 1.46(3H,t,J=7.2 Hz), 3.87(3H,s), 3.98(3H,s), 4.35(2H,q,J=7.2 Hz), 6.99(2H,d,J=8.9 Hz), 7.76(2H,d,J=8.9 Hz), 8.22(1H,s). IR (KBr) cm$^{-1}$: 1749,1721,1712,1661,1599,1519,1272. Mass (m/z): 288 (M$^+$).

Example 3

Preparation of 2-Cyanomethyl-4-methoxycarbonyl-6-(4-methoxyphenyl)-2H-pyridazin-2-one Using 4-methoxycarbonyl-6-(4-methoxyphenyl)-2H-pyridazin-3-one and bromoacetonitrile as starting materials, the procedures of Example 1 were repeated likewise, whereby the title compound was obtained in a yield of 77.4%.

Yellow prisms (chloroform-hexane); Melting point: 128.0–129.8° C. (dec.); $^1$H-NMR (CDCl$_3$) δ: 3.88(3H,s), 4.00(3H,s), 5.15(2H,s), 7.01(2H,d,J=9.0 Hz), 7.78(2H,d,J=9.0 Hz), 8.31(1H,s). IR (KBr) cm$^{-1}$: 1721,1669,1608,1520, 1313,1276,1251. Mass (m/z): 299 (M$^+$).

Example 4

Preparation of 4-Methoxycarbonyl-6-(4-methoxyphenyl)-2-n-propyl-2H-pyridazin-3-one Using 4-methoxycarbonyl-6-(4-methoxyphenyl)-2H-pyridazin-3-one and bromopropane as starting materials, the procedures of Example 1 were repeated likewise, whereby the title compound was obtained in a yield of 78.3%.

Pale yellow needles (chloroform-hexane); Melting point: 104.8–105.8° C.; $^1$H-NMR (CDCl$_3$) δ: 1.00(3H,t,J=7.4 Hz), 1.84–1.99(2H,m), 3.87(3H,s), 3.98(3H,s), 4.26(2H,t,J=7.4 Hz), 6.99(2H,d,J=8.9 Hz), 7.75(2H,d,J=8.9 Hz), 8.21(1H,s). IR (KBr) cm$^{-1}$: 1718,1668,1609,1519,1316,1277,1253, 1187, 1021,838,797. Mass (m/z): 302 (M$^+$).

Example 5

Preparation of 2-(2-Cyanoethyl)-4-methoxycarbonyl-6-(4-methoxyphenyl)-2H-pyridazin-3-one Using 4-methoxycarbonyl-6-(4-methoxyphenyl)-2H-pyridazin-3-one and 3-chloropropionitrile as starting materials, the procedures of Example 1 were repeated likewise, whereby the title compound was obtained in a yield of 78.9%.

Yellow prisms (chloroform-hexane); Melting point: 140.6–143.1° C.; $^1$H-NMR (CDCl$_3$) δ: 2.99(2H,t,J=6.7 Hz), 3.87(3H,s), 3.99(3H,s), 4.56(2H,t,J=6.7 Hz), 7.00(2H,d,J=9.0 Hz), 7.77(2H,d,J=9.0 Hz), 8.28(1H,s). IR (KBr) cm$^{-1}$: 2246,1717,1664,1520,1275,1250. Mass (m/z): 313 (M$^+$).

Example 6

Preparation of 2-(2-Chloroethyl)-4-ethyoxycarbonyl-6-(4-methoxyphenyl)-2H-pyridazin-3-one Using 4-ethoxycarbonyl-6-(4-methoxyphenyl)-2H-pyridazin-3-one and 1-bromo-2-chloroethane as starting materials, the procedures of Example 1 were repeated likewise, whereby the title compound was obtained in a yield of 88.8%.

Yellow needles (chloroform-hexane); Melting point: 97.2–97.7° C.; $^1$H-NMR (CDCl$_3$) δ: 1.43(3H,t,J=7.3 Hz), 3.87(3H,s), 3.97(2H,t,J=6.4 Hz), 4.45(2H,q,J=7.3 Hz), 4.61 (2H,t,J=6.4 Hz), 7.00(2H,d,J=8.9 Hz), 7.75(2H,d,J=8.9 Hz), 8.21(1H,s). IR (KBr) cm$^{-1}$: 1707,1673,1605,1523,1389, 1321,1275,1261, 1184,1130,1034,842. Mass (m/z): 338 (M$^+$), 336 (M$^+$).

Example 7

Preparation of 4-Ethoxycarbonyl-6-(4-methoxyphenyl)-2-vinyl-2H-pyridazin-3-one and 4-ethoxycarbonyl-2-(2-hydroxyethyl)-6-(4-methoxyphenyl)-2H-pyridazin-3-one Potassium carbonate (115 mg, 0.83 mmol) was added to a solution of 2-(2-chloroethyl)-4-ethoxycarbonyl-6-(4-methoxyphenyl)-2H-pyridazin-3-one (140 mg, 0.15 mmol) in N,N-dimethylformamide (1 ml), followed by stirring at 80° C. for 2 hours. Inorganic matter was filtered off, the solvent was distilled off under reduced pressure, and the residue was then subjected to chromatography on a silica gel column (silica gel: 5 g). From ethyl acetate/hexane (½) eluate fractions, the title compound [4-ethoxycarbonyl-6-(4-methoxyphenyl)-2-vinyl-2H-pyridazin-3-one; 34 mg, 27.2%) was obtained as a yellow oil.

$^1$H-NMR (CDCl$_3$) δ: 1.42(3H,t,J=7.1 Hz), 3.87(3H,s), 4.44(2H,q,J=7.1 Hz), 5.10(1H,d,J=8.5 Hz), 5.95(1H,d,J=8.5 Hz), 7.00(2H,d,J=8.8 Hz), 7.80(2H,d,J=8.8 Hz), 7.87(1H, dd,J=8.5,15.6 Hz), 8.18(1H,s).

Subsequently, from chloroform/methanol (20/1) eluate fractions, the title compound [4-ethoxycarbonyl-2-(2-hydroxyethyl)-6-(4-methoxyphenyl)-2H-pyridazin-3-one (93 mg, 70.4%) was obtained as yellow crystals.

Yellow needles (chloroform-hexane); Melting point: 104.6–105.4° C.; $^1$H-NMR (CDCl$_3$) δ: 1.41(3H,t,J=7.3 Hz), 2.75(1H,br), 3.86(3H,s), 4.11(2H,t,J=5.1 Hz), 4.44(2H,q,J= 7.3 Hz), 4.50(2H,t,J=5.1 Hz), 6.99(2H,d,J=8.6 Hz), 7.73 (2H,d,J=8.6 Hz), 8.19(1H,s). IR (KBr) cm$^{-1}$: 3426,1717, 1706,1655,1596,1520,1389,1316, 1266,1027,831,795. Mass (m/z): 318 (M$^+$).

Example 8

Preparation of 6-(3-Chloro-4-fluorophenyl)-2-cinnamyl-4-ethoxycarbonyl-2H-pyridazin-3-one Using 6-(3-chloro-4-fluorophenyl)-4-ethoxycarbonyl-2H-pyridazin-3-one and cinnamyl bromide as starting materials, the procedures of Example 1 were repeated likewise, whereby the title compound was obtained in a yield of 59.3%.

Pale yellow oil; $^1$H-NMR (CDCl$_3$) δ: 1.43(3H,t,J=7.3 Hz), 4.45(2H,q,J=7.3 Hz), 5.04(2H,dd,J=1.0,6.6 Hz), 6.44 (1H,td,J=6.6,15.8 Hz), 6.77(1H,d,J=15.8 Hz), 7.21–7.41 (7H,m), 7.90(1H,dd,J=2.3,6.9 Hz), 8.17(1H,s). IR (film) cm$^{-1}$: 1749,1668,1605,1504,1264,1148,1021,968, 924,753, 693.

Example 9

Preparation of 4-Ethoxycarbonyl-2-isopropyl-6-(4-methoxyphenyl)-2H-pyridazin-3-one Using 4-methoxycarbonyl-6-(4-methoxyphenyl)-2H-pyridazin-3-one and 2-bromopropane as starting materials, the procedures of Example 1 were repeated likewise, whereby the title compound was obtained in a yield of 86.7%.

Pale yellow needles (chloroform-hexane); Melting point: 140.6–141.1° C.; $^1$H-NMR (CDCl$_3$) δ: 1.42(3H,t,J=7.1 Hz), 1.44(6H,d,J=6.6 Hz), 3.87(3H,s), 4.44(2H,q,J=7.1 Hz), 5.39–5.54(1H,m), 6.99(2H,d,J=9.0 Hz), 7.77(2H,d,J=9.0 Hz), 8.14(1H,s). IR (KBr) cm$^{-1}$: 1713,1664,1601,1518, 1390,1323,1271,1177, 1132,1030,829. Mass (m/z): 316 (M$^+$).

Example 10

Preparation of 4-Ethoxycarbonyl-2-isobutyl-6-(4-methoxyphenyl)-2H-pyridazin-3-one Potassium carbonate (605 mg, 4.38 mmol) and 1-bromo-2-methylpropane (360 mg, 2.63 mmol) were added to a solution of 4-ethoxycarbonyl-6-(4-methoxyphenyl)-2H-pyridazin-3-one (600 mg, 2.19 mmol) in N,N-dimethylformamide (6 m), followed by stirring at 80° C. for 30 minutes. After inorganic matter was filtered off, the solvent was distilled off under reduced pressure. The residue was separated and purified by chromatography on a silica gel column [silica gel: 15 g, hexane/ethyl acetate (1/1)], whereby the title compound (705 mg, 97.5%) was obtained.

Pale yellow needles (chloroform-hexane); Melting point: 83.0–83.3° C.; $^1$H-NMR (CDCl$_3$) δ: 0.99(6H,d,J=6.8 Hz), 1.42(3H,t,J=7.1 Hz), 2.29–2.45(1H,m), 3.87(3H,s), 4.11 (2H,d,J=7.3 Hz), 4.44(2H,q,J=7.1 Hz), 6.99(2H,d,J=8.9 Hz), 7.75(2H,d,J=8.9 Hz), 8.17(1H,s). IR (KBr) cm$^{-1}$: 1717, 1709,1665,1599,1518,1388,1333,1271, 1177,1159,1113, 1019,829. Mass (m/z): 330 (M$^+$).

Example 11

Preparation of 6-(3,4-Dimethoxyphenyl)-2-isobutyl-4-methoxycarbonyl-2H-pyridazin-3-one Using 6-(3,4-dimethoxyphenyl)-4-methoxycarbonyl-2H-pyridazin-3-one and 1-bromo-2-methylpropane as starting materials, the procedures of Example 1 were repeated likewise, whereby the title compound was obtained in a yield of 86.6%.

Yellow needles (chloroform-hexane); Melting point: 104.2–105.5° C.; $^1$H-NMR (CDCl$_3$) δ: 1.00(6H,d,J=6.8 Hz), 2.29–2.45(1H,m), 3.94(3H,s), 3.98(3H,s), 4.02(3H,s), 4.13 (2H,d,J=7.3 Hz), 6.94(2H,d,J=8.6 Hz), 7.33(1H,dd,J=2.2, 8.6 Hz), 7.38(1H,d,J=2.2 Hz), 8.23(1H,s). IR (Kbr) cm$^{-1}$: 1710,1665,1522,1429,1423,1297,1248,1228, 1177,1112, 1026. Mass (m/z): 346 (M$^+$).

Example 12

Preparation of 6-(3-Fluoro-4-methoxyphenyl)-2-isobutyl-4-methoxycarbonyl-2H-pyridaz in-3 -one Using 6-(3-fluoro-4-methoxyphenyl)-4-methoxycarbonyl-2H-pyridazin-3-one and 1-bromo-2-methylpropane as starting materials, the procedures of Example 1 were repeated likewise, whereby the title compound was obtained in a yield of 69.9%.

Yellow needles (chloroform-hexane); Melting point: 119.3–121.3° C; $^1$H-NMR (CDCl$_3$) δ: 0.99(6H,d,J=6.6 Hz), 2.37–2.44(1H,m), 3.95(3H,s), 3.98(3H,s), 4.11(2H,d,J=7.3 Hz), 6.99–7.07(1H,m), 7.47–7.53(1H,m), 7.57–7.64(1H,m), 8.23(1H,s). IR (KBr) cm$^{-1}$: 1746,1660,1522,1434,1290, 1195,1178,1136, 1099,1013.

Example 13

Preparation of 6-(3-Chloro-4-methoxyphenyl)-2-isobutyl-4-methoxycarbonyl-2H-pyridazin-3-one Using 6-(3-chloro-4-methoxyphenyl)-4-methoxycarbonyl-2H-pyridazin-3-one and 1-bromo-2-methylpropane as starting materials, the procedures of Example 1 were repeated likewise, whereby the title compound was obtained in a yield of 79.5%.

Yellow needles (chloroform-hexane); Melting point: 108.2–109.4° C.; $^1$H-NMR (CDCl$_3$) δ: 0.99(6H,d,J=6.6 Hz), 2.29–2.45(1H,m), 3.97(3H,s), 3.98(3H,s), 4.12(2H,d,J=7.3 Hz), 7.01(1H,d,J=8.8 Hz), 7.67(1H,dd,J=2.2,8.8 Hz), 7.86 (1H,d,J=2.2 Hz), 8.19(1H,s). IR (KBr) cm$^{-1}$: 1713,1663, 1603,1510,1293. Mass (m/Z): 352 (M$^+$), 350 (M$^+$).

Example 14

Preparation of 2-Isobutyl-4-methoxycarbonyl-6-[4-(methylthio)phenyl]-2H-pyridazin-3-one Using 4-methoxycarbonyl-6-[4-(methylthio)phenyl]-2H-pyridazin-3-one and 1-bromo-2-methylpropane as starting materials, the procedures of Example 1 were repeated likewise, whereby the title compound was obtained in a yield of 77.3%.

Yellow needles (chloroform-hexane); Melting point: 90.4–91.4° C.; $^1$H-NMR (CDCl$_3$) δ: 0.99(6H,d,J=6.6 Hz), 2.29–2.42(1H,m), 2.53(3H,s), 3.98(3H,s), 4.12(2H,d,J=7.3 Hz), 7.32(2H,d,J=8.8 Hz), 7.73(2H,d,J=8.8 Hz), 8.23(1H,s). IR (KBr) cm$^{-1}$: 1714,1672,1601,1502,1268,1251. Mass (m/z): 332 (M$^+$).

Example 15

Preparation of 4-Ethoxycarbonyl-6-(4-methoxyphenyl)-2-(3-methyl-2-butenyl)-2H-pyridazin-3-one Using 4-ethoxycarbonyl-6-(4-methoxyphenyl)-2H-pyridazin-3-one and 1-bromo-3-methyl-2-butene as starting materials, the procedures of Example 1 were repeated likewise, whereby the title compound was obtained in a yield of 87.6%.

Oil; $^1$H-NMR (CDCl$_3$) δ: 1.42(3H,t,J=7.1 Hz), 1.75(3H, s), 1.86(3H,s), 3.86(3H,s), 4.44(2H,q,J=7.1 Hz), 4.87(2H,d, J=7.1 Hz), 5.43–5.52(1H,m), 6.99(2H,d,J=8.9 Hz), 7.75(2H, d,J=8.9 Hz), 8.16(1H,s). IR (KBr) cm$^{-1}$: 1745,1713,1668, 1609,1519,1309,1260,1181, 1134,1022,835. Mass (m/z): 342 (M$^+$).

Example 16

Preparation of 2-Cyclopropylmethyl-4-ethoxycarbonyl-6-(4-methoxyphenyl)-2H-pyridazin-3-one Using 4-ethoxycarbonyl-6-(4-methoxyphenyl)- 2H-pyridazin-3-one and (chloromethyl)cyclopropane as starting materials, the procedures of Example 1 were repeated likewise, whereby the title compound was obtained in a yield of 89.6%.

Pale yellow needles (chloroform-hexane); Melting point: 80.1–80.9° C.; $^1$H-NMR (CDCl3) δ: 0.46–0.59(4H,m), 1.40–1.51(4H,m), 3.87(3H,s), 4.14(2H,d,J=7.3 Hz), 4.44 (2H,q,J=7.1 Hz), 6.99(2H,d,J=9.0 Hz), 7.75(2H,d,J=9.0 Hz), 7.47–7.51(2H,m), 8.18(1H,s). IR (KBr) cm$^{-1}$: 1715,1706, 1664,1598,1389,1273,1128,1114, 1020,828. Mass (m/z): 328 (M$^+$).

Example 17

Preparation of 2-Cyclopropylmethyl-6-(3,4-dimethoxyphenyl)-4-methoxycarbonyl-2H-pyridazin-3-one Using 6-(3,4-dimethoxyphenyl)-4-methoxycarbonyl-2H-pyridazin-3-one and (chloromethyl)cyclopropane as starting materials, the procedures of Example 1 were repeated likewise, whereby the title compound was obtained in a yield of 78.7%.

Yellow needles (chloroform-hexane); Melting point: 136.5–137.3° C.; $^1$H-NMR (CDCl$_3$) δ: 0.46–0.62(4H,m), 1.39–1.52(1H,m), 3.94(3H,s), 3.97(3H,s), 3.99(3H,s), 4.16 (2H,d,J=7.3 Hz), 6.94(1H,d,J=8.3 Hz), 7.33(1H,dd,J=2.2, 8.3 Hz), 7.39(1H,d,J=2.2 Hz), 8.23(1H,s). IR (Kbr) cm$^{-1}$: 1709,1664,1525,1431,1300,1248,1229,1176, 1120,1026, 1020. Mass (m/z): 344 (M$^+$).

Example 18

Preparation of 2-Cyclopropylmethyl-6-(3-fluoro-4-methoxyphenyl)-4-methoxycarbonyl-2H-pyridazin-3-one Using 6-(3-fluoro-4-methoxyphenyl)-4-methoxycarbonyl-2H-pyridazin-3-one and (chloromethyl) cyclopropane as starting materials, the procedures of Example 1 were repeated likewise, whereby the title compound was obtained in a yield of 54.7%.

Yellow needles (chloroform-hexane); Melting point: 113.6–116.6° C.; $^1$H-NMR (CDCl$_3$) δ: 0.44–0.62(4H,m), 1.37–1.52(1H,m), 3.95(3H,s), 3.98(3H,s), 4.14(2H,d,J=7.3 Hz), 7.00–7.07(1H,m), 7.48–7.53(1H,m), 7.58–7.64(1H,m), 8.21(1H,s). IR (KBr) cm$^{-1}$: 1721,1660,1521,1437,1295, 1275,1258,1106, 1023.

Example 19

Preparation of 6-(3-Chloro-4-methoxyphenyl)-2-cyclopropylmethyl-4-methoxycarbonyl-2H-pyridazin- 3-one Using 6-(3-chloro-4-methoxyphenyl)-4-methoxycarbonyl-2H-pyridazin-3-one and (chloromethyl) cyclopropane as starting materials, the procedure of Example 1 were repeated likewise, whereby the title compound was obtained in a yield of 72.7%.

Pale yellow needles (chloroform-hexane); Melting point: 101.4–103.8° C.; $^1$H-NMR (CDCl$_3$) δ: 0.45–0.62(4H,m), 1.48–1.52(1H,m), 3.97(3H,s), 3.99(3H,s), 4.15(2H,d,J=4.5 Hz), 7.01(1H,d,J=8.5 Hz), 7.66(1H,dd,J=2.4,8.5 Hz), 7.87 (1H,d,J=2.4 Hz), 8.21(1H,s). IR (KBr) cm$^{-1}$: 1718,1660, 1602,1509,1293. Mass (m/z): 350 (M$^+$), 348 (M$^+$).

Example 20

Preparation of 2-Cyclopropylmethyl-4-methoxycarbonyl-6-[4-(methylthio)phenyl]-2H-pyridazin-3-one Using 4-methoxycarbonyl-6-[4-(methylthio)phenyl]-2H-pyridazin-3-one and (chloromethyl)cyclopropane as starting materials, the procedures of Example 1 were repeated likewise, whereby the title compound was obtained in a yield of 61.5%.

Yellow needles (chloroform-hexane); Melting point: 100.2–101.8° C.; $^1$H-NMR (CDCl3) δ: 0.41–0.61(4H,m), 1.38–1.51(1H,m), 2.53(3H,s), 3.98(3H,s), 4.15(2H,d,J=7.3 Hz), 7.32(2H,d,J=8.4 Hz), 7.73(2H,d,J=8.4 Hz), 8.24(1H,s). IR (KBr) cm$^{-1}$: 1731,1668,1602,1328,1267,1249. Mass (m/z): 330 (M$^+$).

Example 21

Preparation of 2-Cyclopentylmethyl-4-ethoxycarbonyl-6-(4-methoxyphenyl)-2H-pyridazin-3-one Using 4-ethoxycarbonyl-6-(4-methoxyphenyl)-2H-pyridazin-3-one and cyclopentylmethyl methanesulfonate as starting materials, the procedures of Example 1 were repeated likewise, whereby the title compound was obtained in a yield of 88.5%.

Pale yellow needles (chloroform-hexane); Melting point: 63.6–64.4° C.; $^1$H-NMR (CDCl$_3$) δ: 1.26–1.46(5H,m), 1.49–1.81(6H,m), 2.50–2.66(1H,m), 3.87(3H,s), 4.23(2H,d, J=7.6 Hz), 4.44(2H,q,J=7.1 Hz), 6.99(2H,d,J=8.8 Hz), 7.75 (2H,d,J=8.8 Hz), 8.17(1H,s). IR (KBr) cm$^{-1}$: 1708,1667, 1601,1518,1388,1272,1178, 1130,1114,1027,827,794. Mass (m/z): 356 (M$^+$).

Example 22

Preparation of 2-Benzyl-4-methoxycarbonyl-6-(4-methoxyphenyl)-2H-pyridazin-3-one Using 4-methoxycarbonyl-6-(4-methoxyphenyl)-2H-pyridazin-3-one and benzyl bromide as starting materials, the procedures of Example 1 were repeated likewise, whereby the title compound was obtained in a yield of 96.9%.

Pale yellow crystals; $^1$H-NMR (CDCl$_3$) δ: 3.86(3H,s), 3.96(3H,s), 5.43(2H,s), 6.98(2H,d,J=9.1 Hz), 7.28–7.37(3H, m), 7.47–7.55(2H,m), 7.75(2H,d,J=9.1 Hz), 8.22(1H,s). Mass (m/z): 350 (M$^+$).

Example 23

Preparation of 2-Benzyl-4-ethoxycarbonyl-6-(4-methoxyphenyl)-2H-pyridazin-3-one

Using 4-ethoxycarbonyl-6-(4-methoxyphenyl)-2H-pyridazin-3-one and benzyl bromide as starting materials, the procedures of Example 1 were repeated likewise, whereby the title compound was obtained in a yield of 75.3%.

Pale yellow crystals; $^1$H-NMR (CDCl$_3$) δ: 1.41(3H,t,J= 7.1 Hz), 3.86(3H,s), 4.42(2H,q,J=7.1 Hz), 5.43(2H,s), 6.98 (2H,d,J=9.0 Hz), 7.26–7.36(3H,m), 7.50–7.55(2H,m), 7.75 (2H,d,J=9.0 Hz), 8.17(1H,s).

Example 24

Preparation of 2-(2,4-Dichlorobenzyl)-4-ethoxycarbonyl- 6-(4-methoxyphenyl)-2H-pyridazin-3-one Using 4-ethoxycarbonyl-6-(4-methoxyphenyl)-2H-pyridazin-3-one and 2,4-dichlorobenzyl chloride as starting materials, the procedures of Example 1 were repeated likewise, whereby the title compound was obtained in a yield of 88.3%.

Yellow needles (chloroform-hexane); Melting point: 135.7–136.3° C.; $^1$H-NMR (CDCl$_3$) δ: 1.42(3H,t,J=7.1 Hz), 3.86(3H,s), 4.44(2H,q,J=7.1 Hz), 5.54(2H,s), 6.98(2H,d,J= 8.9 Hz), 7.20(1H,dd,J=2.2,8.3 Hz), 7.29(1H,d,J=8.3 Hz), 7.43(1H,d,J=2.2 Hz), 7.71(2H,d,J=8.9 Hz), 8.22(1H,s). IR (KBr) cm$^{-1}$: 1748,1719,1664,1608,1518,1311,1254, 1242, 1163,1136,1026,836. Mass (m/z): 436 (M$^+$), 434 (M$^+$), 432 (M$^+$).

Example 25

Preparation of 4-Methoxycarbonyl-6-(4-methoxyphenyl)-2-(4-nitrobenzyl)-2H-pyridazin-3-one Using 4-methoxycarbonyl-6-(4-methoxyphenyl)-2H-pyridazin-3-one and 4-nitrobenzyl chloride as starting materials, the procedures of Example 1 were repeated likewise, whereby the title compound was obtained in a yield of 92.6%.

Yellow fine needles (chloroform-hexane); Melting point: 215.4–216.6° C.; $^1$H-NMR (CDCl$_3$) δ: 3.87(3H,s), 3.97(3H, s), 5.50(2H,s), 7.00(2H,d,J=9.0 Hz), 7.67(2H,d,J=8.8 Hz), 7.74(2H,d,J=9.0 Hz), 8.20(2H,d,J=8.8 Hz), 8.26(1H,s). IR (KBr) cm$^{-1}$: 1720,1663,1601,1522,1347,1255. Mass (m/z): 395 (M$^+$).

Example 26

Preparation of 2-(4-Aminobenzyl)-4-methoxycarbonyl-6-(4-methoxyphenyl)-2H-pyridazin-3-one To a solution of 4-methoxycarbonyl-6-(4-methoxyphenyl)-2-(4-nitrobenzyl)-2H-pyridazin-3-one (100 mg, 0.25 mmol) in methanol (30 m), 10% palladium on charcoal (40 mg) was added, followed by catalytic reduction at room temperature under atmospheric pressure. Thirty minutes later, the catalyst was filtered off. The methanol was distilled off under reduced pressure. The residue was crystallized from chloroform-diethyl ether-hexane, whereby the title compound (91 mg, 98.5%) was obtained as yellow fine needles.

Melting point: 160.0–161.9° C.; $^1$H-NMR (CDCl$_3$) δ: 3.65(2H,br), 3.87(3H,s), 3.95(3H,s), 5.31(2H,s), 6.63(2H,d, J=8.4 Hz), 6.98(2H,d,J=8.8 Hz), 7.36(2H,d,J=8.4 Hz), 7.75 (2H,d,J=8.8 Hz), 8.19(1H,s). IR (KBr) cm$^{-1}$: 3417,3331, 1741,1646,1611,1595,1517,1286, 1256,1181. Mass (m/z): 365 (M$^+$).

Example 27

Preparation of 4-Methoxycarbonyl-6-(4-methoxyphenyl)-2-[4-(3-pyridylcarbonylamino) benzyl]-2H-pyridazin-3-one To a suspension of nicotinic acid (38 mg, 0.31 mmol) in tetrahydrofuran (2 ml), N-[3-(dimethylamino)-propyl]-N'- ethylcarbodiimide.hydrochloride (WSC.HCl) (60 mg,0.31 mmol) was added at room temperature, followed by stirring for 5 minutes. A solution of 2-(4-aminobenzyl)-4-methoxycarbonyl-6-(4-methoxyphenyl)-2H-pyridazin-3-one (76 mg, 0.21 mmol) in tetrahydrofuran (2 ml) was then added, followed by stirring at the same temperature for 13 hours. The solvent was distilled off under reduced pressure, and the residue was dissolved in chloroform (30 ml). The solution was washed successively with water (30 ml) and a saturated aqueous solution of sodium chloride (brine) (30 ml), and was then dried over anhydrous sodium sulfate. The solvent was distilled off under reduced pressure. The residue was separated and purified by silica gel preparative chromatography [developer: chloroform/methanol (10/1)], followed by crystallization from chloroform-hexane. The title compound (78 mg, 79.7%) was obtained as yellow prisms.

Melting point: 235.7–236.9° C. (dec.); $^1$H-NMR (CDCl$_3$) δ: 3.87(3H,s), 3.92(3H,s), 5.42(2H,s), 7.00(2H,d,J=9.0 Hz), 7.40–7.46(1H,m), 7.56(2H,d,J=8.5 Hz), 7.63(2H,d,J=8.5 Hz), 7.76(2H,d,J=9.0 Hz), 8.07(1H,br), 8.19–8.25(2H,m), 8.75–8.78(1H,m), 8.99–9.12(1H,s). IR (KBr) cm$^{-1}$: 3303, 3266,1740,1668,1640,1606,1542,1518, 1412,1321,1253. Mass (m/z): 470 (M$^+$)

Example 28

Preparation of 4-Methoxycarbonyl-6-(4-methoxyphenyl)-2-(3-pyridylmethyl)-2H-pyridazin-3-one Using 4-methoxycarbonyl-6-(4-methoxyphenyl)-2H-pyridazin-3-one and 3-(chloromethyl)pyridine hydrochloride as starting materials, the procedures of Example 1 were repeated likewise, whereby the title compound was obtained in a yield of 38.5%.

Pale yellow needles (chloroform-ether-hexane); Melting point: 112.3–115.3° C. (dec.); $^1$H-NMR (CDCl$_3$) δ: 3.87 (3H,s), 3.97(3H,s), 5.44(2H,s), 6.99(2H,d,J=9.0 Hz), 7.24–7.30(1H,m), 7.74(2H,d,J=9.0 Hz), 7.86–7.92(1H,m), 8.24(1H,s), 8.54–8.57(1H,m), 7.98–8.81(1H,m). IR (KBr) cm$^{-1}$: 1720,1665,1599,1518,1311,1270. Mass (m/z): 351 (M$^+$).

Example 29

Preparation of 4-Methoxycarbonyl-6-(4-methoxyphenyl)-2-(3-phenylpropyl)-2H-pyridazin-3-one Using 4-methoxycarbonyl-6-(4-methoxyphenyl)-2H-pyridazin-3-one and 3-phenylpropyl bromide as starting materials, the procedures of Example 1 were repeated likewise, whereby the title compound was obtained in a yield of 94.0%.

Yellow oil; $^1$H-NMR (CDCl$_3$) δ: 1.42(3H,t,J=7.1Hz), 2.17–2.30(2H,m), 2.74(2H,t,J=7.8 Hz), 3.86(3H,s), 4.33 (2H,t,J=7.1 Hz), 4.44(2H,q,J=7.1 Hz), 6.98(2H,d,J=8.9 Hz), 7.13–7.30(5H,m), 7.74(2H,d,J=8.9 Hz), 8.14(1H,s). IR (film) cm$^{-1}$: 1744,1713,1664,1610,1519,1256,1180, 1131, 1021. Mass (m/z): 392 (M$^+$). HRMS: Calcd. for C$_{23}$H$_{24}$N$_2$O$_4$ (Found): 392.17358 (392.17107).

Example 30

Preparation of 2-Cinnamyl-4-ethoxycarbonyl-6-(4-methoxyphenyl)-2H-pyridazin-3-one Using 4-ethoxycarbonyl-6-(4-methoxyphenyl)-2H-pyridazin-3-one and cinnamyl bromide as starting materials, the procedures of Example 1 were repeated likewise, whereby the title compound was obtained in a yield of 92.1%.

Pale yellow oil; $^1$H-NMR (CDCl$_3$) δ: 1.42(3H,t,J=7.1 Hz), 3.86(3H,s), 4.45(2H,q,J=7.1 Hz), 5.03(2H,d,J=6.6 Hz), 6.46(1H,td,J=6.6,15.9 Hz), 6.75(1H,d,J=15.9 Hz), 6.99(2H, d,J=9.0 Hz), 7.20–7.41(5H,m), 7.76(2H,d,J=9.0 Hz), 8.19 (1H,s). IR (film) cm$^{-1}$: 1744,1713,1668,1609,1518,1309, 1256, 1025,835.

Example 31

Preparation of 2-(4-Chlorocinnamyl)-4-ethoxycarbonyl-6-(4-methoxyphenyl)-2H-pyridazin-3-one Using 4-ethoxycarbonyl-6-(4-methoxyphenyl)-2H-pyridazin-3-one and 4-chlorocinnamyl chloride as starting materials, the procedures of Example 1 were repeated likewise, whereby the title compound was obtained in a yield of 85.7%.

Yellow needles (chloroform-hexane); Melting point: 127.0–127.9° C.; $^1$H-NMR (CDCl$_3$) δ: 1.42(3H,t,J=7.1 Hz), 3.87(3H,s), 4.45(2H,q,J=7.1 Hz), 5.02(2H,td,J=1.0,6.6 Hz), 6.42(1H,td,J=6.6,15.9 Hz), 6.69(1H,td,J=1.0,15.9 Hz), 6.99 (2H,d,J=8.9 Hz), 7.26(2H,d,J=8.9 Hz), 7.32(2H,d,J=8.9 Hz), 7.76(2H,d,J=8.9 Hz), 8.20(1H,s). 1181,1149,1026,1015, 831. Mass (m/z): 426 (M$^+$), 424 (M$^+$).

Example 32

Preparation of 2-(4-Chlorocinnamyl)-6-(3,4-dimethoxyphenyl)-4-methoxycarbonyl-2H-pyridazin-3-one Melting point: 117.5–118.7° C.; $^1$H-NMR (CDCl$_3$) δ: 3.94(3H,s), 3.95(3H,s), 3.99(3H,s), 5.03(2H,dd,J=1.0,6.6 Hz), 6.43(1H,td,J=6.6,15.9 Hz), 6.70(1H,td,J=1.0,15.9 Hz), 6.94(1H,d,J=8.3 Hz), 7.27(2H,d,J=8.8 Hz), 7.31(2H,d,J=8.8 Hz), 7.33(1H,dd,J=2.2,8.3 Hz), 7.38(1H,d,J=2.2 Hz), 8.26 (1H,s). IR (KBr) cm$^{-1}$: 3046,1704,1674,1516,1419,1247, 1226, 1151,1023,979. Mass (m/z): 442 (M$^+$), 440 (M$^+$).

Example 33

Preparation of 2-(4-Chlorocinnamyl)-6-(3-fluoro-4-methoxyphenyl)-4-methoxycarbonyl-2H-pyridazin-3-one Using 6-(3-fluoro-4-methoxyphenyl)-4-methoxycarbonyl- 2H-pyridazin-3-one and 4-chlorocinnamyl chloride as starting materials, the procedures of Example 1 were repeated likewise, whereby the title compound was obtained in a yield of 75.5%.

Pale yellow needles (chloroform-hexane); Melting point: 131.3–132.3° C.; $^1$H-NMR (CDCl$_3$) δ: 3.95(3H,s), 3.99(3H, s), 5.02(2H,dd,J=1.1,6.7 Hz), 6.42(1H,td,J=6.7,15.9 Hz), 6.70(1H,td,J=1.1,15.9 Hz), 7.00–7.07(1H,m), 7.28(2H,d,J= 8.9 Hz), 7.31(2H,d,J=8.9 Hz), 7.48–7.53(1H,m), 7.59–7.66 (1H,m), 8.22(1H,s). IR (KBr) cm$^{-1}$: 1725,1661,1654,1523, 1319,1271,1129. Mass (m/z): 430 (M$^+$), 428 (M$^+$).

Example 34

Preparation of 2-(4-Chlorocinnamyl)-6-(3-chloro-4-methoxyphenyl)-4-methoxycarbonyl-2H-pyridazin-3-one Using 6-(3-chloro-4-dimethoxyphenyl)-4-methoxycarbonyl-2H-pyridazin-3-one and 4-chlorocinnamyl chloride as starting materials, the procedures of Example 1 were repeated likewise, whereby the title compound was obtained in a yield of 76.8%.

Yellow prisms (chloroform-hexane); Melting point: 179.7–181.6° C.; $^1$H-NMR (CDCl$_3$) δ: 3.97(3H,s), 3.99(3H, s), 5.02(2H,dd,J=1.1,6.7 Hz), 6.42(1H,td,J=6.7,15.9 Hz), 6.71(1H,td,J=1.1,15.9 Hz), 7.01(1H,d,J=8.6 Hz), 7.28(2H, d,J=8. 8 Hz), 7.31(2H,d,J=8.8 Hz), 7.66(1H,dd,J=2.2,8.6 Hz), 7.88(1H,d,J=2.2 Hz), 8.22(1H,s). IR (KBr) cm$^{-1}$: 1747, 1652,1605,1508,1286,1260,1240. Mass (m/z): 446 (M$^+$), 444 (M$^+$).

Example 35

Preparation of 2-(4-Chlorocinnamyl)-4-methoxycarbonyl-6-[4-(methylthio)phenyl]-2H-pyridazin-3-one Using 4-methoxycarbonyl-6-[4-(methylthio)phenyl]-2H-pyridazin-3-one and 4-chlorocinnamyl chloride as starting materials, the procedures of Example 1 were repeated likewise, whereby the title compound was obtained in a yield of 82.3%.

Yellow prisms (chloroform-hexane); Melting point: 123.3–126.2° C.; $^1$H-NMR (CDCl$_3$) δ: 2.53(3H,s), 3.98(3H, s), 5.03(2H,dd,J=1.1,6.7 Hz), 6.43(1H,td,J=6.7,15.9 Hz), 6.70(1H,td,J=1.1,15.9 Hz), 7.27(2H,d,J=8.8 Hz), 7.30(2H, d,J=8.8 Hz),7.32(2H,d,J=8.7 Hz), 7.73(2H,d,J=8.7 Hz), 8.26 (1H,s). IR (KBr) cm$^{-1}$: 1712,1666,1600,1502,1490,1270, 1095,977. Mass (m/z): 428 (M$^+$), 426 (M$^+$).

Example 36

Preparation of 2-(2,4-Difluorocinnamyl)-4-ethoxycarbonyl-6-(4 -methoxyphenyl)-2H-pyridazin-3-one Using 4-ethoxycarbonyl-6-(4-methoxyphenyl)-2H-pyridazin-3-one and 2,4-difluorocinnamyl chloride as starting materials, the procedures of Example 1 were repeated likewise, whereby the title compound was obtained in a yield of 92.0%.

Yellow oil; $^1$H-NMR (CDCl$_3$) δ: 1.42(3H,t,J=7.1 Hz), 3.87(3H,s), 4.45(2H,q,J=7.1 Hz), 5.04(2H,dd,J=1.0,6.6 Hz), 6.48(1H,dd,J=6.6,16.0 Hz), 6.73–6.87(3H,m), 6.99(2H,d,J= 8.9 Hz), 7.37–7.47(1H,m), 7.76(2H,d,J=8.9 Hz), 8.20(1H,s). IR (film) cm$^{-1}$: 3074,1745,1713,1668,1610,1519,1503, 1258,1141,1026,967. Mass (m/z): 426 (M$^+$). HRMS: Calcd. for C$_{23}$H$_{20}$F$_2$N$_2$O$_4$ (Found): 426.13908 (426.14058).

Example 37

Preparation of 4-Methoxycarbonyl-6-(4-methoxyphenyl)-2-[4-(methylthio) phenylcarbamoylmethyl]-2H-pyridazin-3-one (1) Preparation of 2-Bromo-4'-(methylthio)acetanilide To a solution of 4-(methylthio)aniline (200 mg, 1.44 mmol) in chloroform (2 ml), a saturated aqueous solution of sodium hydrogencarbonate (2 ml) was added, followed by the dropwise addition of a solution of bromoacetyl bromide (300 mg, 1.49 mmol) in chloroform (2 ml) under ice cooling. The mixture was then stirred for 1 hour. The chloroform layer was separated, washed successively with 2N hydrochloric acid (10 ml) and brine (10 ml), and then dried over anhydrous sodium sulfate. The solvent was distilled off under reduced pressure, whereby the title compound (356 mg, 95.3%) was obtained as pale brown crystals.

(2) Preparation of 4-Methoxycarbonyl-6-(4-methoxyphenyl)-2-[4-(methylthio) phenylcarbamoylmethyl]-2H-pyridazin-3-one Using 4-methoxycarbonyl-6-(4-methoxyphenyl)-2H-pyridazin-3-one and 2-bromo-4'-(methylthio)acetanilide as starting materials, the procedures of Example 1 were repeated likewise, whereby the title compound was obtained in a yield of 90.0%.

Yellow prisms (chloroform-hexane); Melting point: 130.2–132.4° C.; $^1$H-NMR (CDCl$_3$) δ: 2.44(3H,s), 3.87(3H, s), 3.98(3H,s), 5.08(2H,s), 6.98(2H,d,J=8.9 Hz), 7.19(2H,d, J=8.7 Hz), 7.46(2H,d,J=8.7 Hz), 7.78(2H,d,J=8.9 Hz), 8.32 (1H,s), 8.64(1H,br). IR (KBr) cm$^{-1}$: 3273,1744,1702,1652, 1598,1518,1250. Mass (m/z): 439 (M$^+$).

Example 38

Preparation of 2-Benzyl-4-carbamoyl-6-(4-methoxyphenyl)-2H-pyridazin-3-one

To 2-benzyl-4-methoxycarbonyl-6-(4-methoxyphenyl)-2H-pyridazin-3-one (73 mg, 0.20 mmol), an ammonia-methanol solution (about 10% W/W, 3 ml) was added, followed by stirring at room temperature for 17 hours. Precipitated crystals were collected by filtration, whereby the title compound (59 mg, 90.7%) was obtained as colorless fine needles.

Melting point: 196.0–198.0° C.; $^1$H-NMR (CDCl$_3$) δ: 3.87(3H,s), 5.48(2H,s), 5.93(1H,brs), 6.99(2H,d,J=9.0 Hz), 7.30–7.40(3H,m), 7.49(2H,dd,J=2.0,8.1 Hz), 7.83(2H,d,J= 9.0 Hz), 8.67(1H,s), 9.41(1H,br). IR (KBr) cm$^{-1}$: 3157, 1703,1518,1391,1255,1034,830,729.

Example 39

Preparation of 4-Carbamoyl-2-cyclopropylmethyl-6-(4-methoxyphenyl)-2H-pyridazin-3-one Using 2-cyclopropylmethyl-4-ethoxycarbonyl-6-(4-methoxyphenyl)-2H-pyridazin-3-one as a starting material, the procedures of Example 38 were repeated likewise, whereby the title compound was obtained in a yield of 90.5%.

Slightly yellow prisms (methanol-diethyl ether); Melting point: 182.2–183.3° C.; $^1$H-NMR (CDCl$_3$) δ: 0.47–0.62(4H, m), 1.40–1.51(1H,m), 3.87(3H,s), 4.19(2H,d,J=7.3 Hz), 5.95(1H,br), 7.00(2H,d,J=8.8 Hz), 7.82(2H,d,J=8.8 Hz), 8.68(1H,s), 9.50(1H,br). IR (KBr) cm$^{-1}$: 3322,3161,1694, 1610,1519,1419,1386,1269, 1252,1184,1024, 839. Mass (m/z): 299 (M$^+$).

Example 40

Preparation of 4-Carbamoyl-2-cyclopentylmethyl-6-(4-methoxyphenyl)-2H-pyridazin-3-one Using 2-cyclopentylmethyl-4-ethoxycarbonyl-6-(4-methoxyphenyl)-2H-pyridazin-3-one as a starting material, the procedures of Example 38 were repeated likewise, whereby the title compound was obtained in a yield of 91.5%.

Colorless needles (chloroform-hexane); Melting point: 182.2–183.3° C.; $^1$H-NMR (CDCl$_3$) δ: 1.31–1.46(2H,m), 1.50–1.83(6H,m), 2.48–2.65(1H,m), 3.87(3H,s), 4.28(2H,d, J=7.6 Hz), 5.94(1H,br), 7.00(2H,d,J=8.9 Hz), 7.82(2H,d,J= 8.9 Hz), 8.67(1H,s), 9.51(1H,br). IR (KBr) cm$^{-1}$: 3350, 3158,1701,1517,1457,1389,1254,1189, 1177, 1131,1033, 828,799. Mass (m/z): 327 (M$^+$).

Example 41

Preparation of 4-Carbamoyl-2-cinnamyl-6-(4-methoxyphenyl)-2H-pyridazin-3-one

Using 2-cinnamyl-4-ethoxycarbonyl-6-(4-methoxyphenyl)-2H-pyridazin-3-one as a starting material, the procedures of Example 38 were repeated likewise, whereby the title compound was obtained in a yield of 40.0%.

Colorless fine needles (chloroform-diethyl ether); Melting point: 184.0–186.0° C.; $^1$H-NMR (CDCl$_3$) δ: 3.87(3H,s), 5.08(2H,dd,J=1.0,6.6 Hz), 5.93(1H,brs), 6.44(1H,td,J=6.6, 15.9 Hz), 6.75(1H,td,J=1.0,15.9 Hz), 6.99(2H,d,J=8.9 Hz), 7.24–7.43(5H,m), 7.83(2H,d,J=9.0 Hz), 8.69(1H,s), 9.44 (1H,br). IR (KBr) cm$^{-1}$: 3347,3148,1704,1633,1610,1517, 1391,1254, 1034,829.

Example 42

Preparation of 4-Carbamoyl-2-(4-chlorocinnamyl)-6-(4-methoxyphenyl)-2H-pyridazin-3-one Using 2-(4-chlorocinnamyl)-4-ethoxycarbonyl-6-(4-methoxyphenyl)-2H-pyridazin-3-one as a starting material, the procedures of Example 38 were repeated likewise, whereby the title compound was obtained in a yield of 96.6%.

Pale yellow fine needles (chloroform-hexane); Melting point: 195.1–195.5° C.; $^1$H-NMR (CDCl$_3$) δ: 3.87(3H,s), 5.07(2H,td,J=1.0,6.6 Hz), 5.98(1H,br), 6.42(1H,td,J=6.6, 15.8 Hz), 6.69(1H,td,J=1.0,15.8 Hz), 6.99(2H,d,J=8.9 Hz), 7.27(2H,d,J=8.6 Hz), 7.33(2H,d,J=8.6 Hz), 7.83(2H,d,J=8.9 Hz), 8.69(1H,s), 9.43(1H,br). IR (KBr) cm$^{-1}$: 3324,3142, 1702,1611,1570,1518,1491, 1388,1257,1169,1034,831. Mass (m/z): 397 (M$^+$), 395 (M$^+$).

Example 43

Preparation of 2-Isobutyl-6-(4-methoxyphenyl)-4-methylcarbamoyl-2H-pyridazin-3-one To 4-ethoxycarbonyl-2-isobutyl-6-(4-methoxyphenyl)-2H-pyridazin-3-one (40 mg, 0.13 mmol), a 30% methylamine-ethanol (2 ml) was added, followed by stirring at room temperature for 30 minutes. The solvent was distilled off under reduced pressure and the residue was crystallized from chloroform-hexane, whereby the title compound (35 mg, 91.9%) was obtained as colorless needles.

Melting point: 124.9–125.2° C.; $^1$H-NMR (CDCl$_3$) δ: 1.00(6H,d,J=6.6 Hz), 2.37–2.44(1H,m), 3.02(3H,d,J=5.3 Hz), 3.87(3H,s), 4.15(2H,d,J=7.3 Hz), 6.99(2H,d,J=8.9 Hz), IR (KBr) cm$^{-1}$: 3244,1686,1590,1253,1184,1026,834. Mass (m/z): 315 (M$^+$).

Example 44

Preparation of 6-(4-Methoxyphenyl)-2-methyl-4-methylcarbamoyl-2H-pyridazin-3 -one Using 2-methoxycarbonyl-6-(4-methoxyphenyl)-2-methyl-2H-pyridazin-3-one as a starting material, the procedures of Example 43 were repeated likewise, whereby the title compound was obtained in a yield of 95.3%.

Slightly yellow needles (chloroform-hexane); Melting point: 150.5–150.7° C.; $^1$H-NMR (CDCl$_3$) δ: 3.03(3H,d,J= 5.0 Hz), 3.87(3H,s), 3.95(3H,s), 6.99(2H,d,J=8.9 Hz), 7.82 (2H,d,J=8.9 Hz), 8.68(1H,s), 9.67(1H,br). IR (KBr) cm$^{-1}$: 3248,1679,1625,1610,1517,1459,1284,1249, 1185,1004, 838.

Example 45

Preparation of 2-Ethyl-6-(4-methoxyphenyl)-4-methylcarbamoyl-2H-pyridazin-3-one

Using 2-ethyl-4-methoxycarbonyl-6-(4-methoxyphenyl)-2H-pyridazin-3-one as a starting material, the procedures of Example 43 were repeated likewise, whereby the title compound was obtained in a yield of 82.8%.

Slightly yellow needles (chloroform-hexane); Melting point: 122.4–122.9° C.; $^1$H-NMR (CDCl$_3$) δ: 1.50(3H,t,J= 7.3 Hz), 3.03(3H,d,J=5.0 Hz), 3.87(3H,s), 4.38(2H,q,J=7.3 Hz), 7.00(2H,d,J=8.9 Hz), 7.83(2H,d,J=8.9 Hz), 8.67(1H,s), 9.72(1H,br). IR (KBr) cm$^{-1}$: 3241,1674,1567,1553,1517, 1415,1251,1183, 1025. Mass (m/z): 287 (M$^+$).

Example 46

Preparation of 2-Cyanomethyl-6-(4-methoxyphenyl)-4-methylcarbamoyl-2H-pyridazin-3-one Using 2-cyanomethyl-4-methoxycarbonyl-6-(4-methoxyphenyl)-2H-pyridazin-3-one as a starting material, the procedures of Example 43 were repeated likewise, whereby the title compound was obtained in a yield of 82.8%.

Pale brown prisms (chloroform-hexane); Melting point: 153.4–154.9° C.; $^1$H-NMR (CDCl$_3$) δ: 3.04(3H,t,J=5.3 Hz), 3.88(3H,s), 5.16(2H,s), 7.01(2H,d,J=8.9 Hz), 7.83(2H,d,J= 8.9 Hz), 8.74(1H,s), 9.28(1H,br). IR (KBr) cm$^{-1}$: 3292, 2261,1690,1679,1554,1517,1257. Mass (m/z): 298 (M$^+$).

Example 47

Preparation of 6-(4-Methoxyphenyl)-4-methylcarbamoyl-2-methylcarbamoylmethyl-2H-pyridazin-3-one (1) Preparation of 4-Ethoxycarbonyl-2-ethoxycarbonylmethyl-6-(4-methoxyphenyl)-2H-pyridazin-3-one Using 4-ethoxycarbonyl-6-(4-methoxyphenyl)-2H-pyridazin-3-one and ethyl bromoacetate as starting materials, the procedures of Example 1 were repeated likewise, whereby the title compound was obtained in a yield of 84.5%.

Pale yellow needles (chloroform-diethyl ether-hexane); Melting point: 77.1–77.8° C.; $^1$H-NMR (CDCl$_3$) δ: 1.29(3H, t,J=7.1 Hz), 1.41(3H,t,J=7.1 Hz), 3.8.6(3H,s), 4.26(2H,q,J= 7.1 Hz), 4.43(2H,q,J=7.1 Hz), 4.99(2H,s), 6.98(2H,d,J=8.9 Hz), 7.73(2H,d,J=8.9 Hz), 8.25(1H,s). IR (KBr) cm$^{-1}$: 1754, 1718,1675,1607,1518,1313,1284,1264, 1217,1159,1030, 1018,842,794. Mass (m/z): 360 (M$^+$).

(2) Preparation of 6-(4-Methoxyphenyl)-4-methylcarbamoyl-2-methylcarbamoylmethyl-2H-pyridazin-3-one Using 4-ethoxycarbonyl-2-ethoxycarbonylmethyl-6-(4-methoxyphenyl)-2H-pyridazin-3-one as a starting material, the procedures of Example 43 were repeated likewise, whereby the title compound was obtained in a yield of 84.5%.

Colorless fine needles; Melting point: 250.1–250.8° C.; $^1$H-NMR (CDCl$_3$) δ: 2.87(3H,d,J=4.6 Hz), 2.99(3H,d,J=5.0 Hz), 3.87(3H,s), 4.95(2H,s), 6.14(2H,br), 6.98(2H,d,J=9.1 Hz), 7.82(2H,d,J=9.1 Hz), 8.70(1H,s), 9.44(1H,br). IR (KBr) cm$^{-1}$: 3293,3114,1683,1666,1516,1252,1164,1026, 834,798. Mass (m/z): 330 (M$^+$).

Example 48

Preparation of 6-(4-Methoxyphenyl)-4-methylcarbamoyl-2-vinyl-2H-pyridazin-3-one

Using 4-ethoxycarbonyl-6-(4-methoxyphenyl)-2-vinyl-2H-pyridazin-3-one as a starting material, the procedures of Example 43 were repeated likewise, whereby the title compound was obtained in a yield of 36.7%.

Yellow needles (chloroform-hexane); Melting point: 130.3–132.8° C.; $^1$H-NMR (CDCl$_3$) δ: 3.03(3H,d,J=5.0 Hz), 3.88(3H,s), 5.18(1H,d,J=8.6 Hz), 6.03(1H,d,J=15.4 Hz), 7.01(2H,d,J=9.0 Hz), 7.85(1H,dd,J=8.6,15.4 Hz), IR (KBr) cm$^{-1}$: 3238,3121,1683,1632,1607,1548,1516,1411, 1314, 1272,1245,1180.

Example 49

Preparation of 2-(2-Hydroxyethyl)-6-(4-methoxyphenyl)-4-methylcarbamoyl-2H-pyridazin-3-one Using 4-ethoxycarbonyl-2-(2-hydroxyethyl)-6-(4-methoxyphenyl)-2H-pyridazin-3-one as a starting material, the procedures of Example 43 were repeated likewise, whereby the title compound was obtained in a yield of 97.2%.

Pale yellow needles (chloroform-hexane); Melting point: 160.3–160.6° C.; $^1$H-NMR (CDCl$_3$) δ: 2.87(1H,brt,J=5.7 Hz), 3.00(3H,d,J=5.1 Hz), 3.87(3H,s), 4.17–4.19(2H,m), 4.51–4.56(2H,m), 7.00(2H,d,J=8.9 Hz), 7.80(2H,d,J=8.9 Hz), 8.69(1H,s), 9.57(1H,br). IR (KBr) cm$^1$: 3462,3228, 1671,1619,1592,1536,1519,1265, 1187,1070,833. Mass (m/z): 303 (M$^+$).

Example 50

Preparation of 2-(2-Cyanoethyl)-6-(4-methoxyphenyl)- 4-methylcarbamoyl-2H-pyridazin-3-one Using 2-(2-cyanoethyl)-4-methoxycarbonyl-6-(4-methoxyphenyl)-2H-pyridazin-3-one as a starting likewise, whereby the title compound was obtained in a yield of 90.3%.

Pale yellow fine needles (chloroform-hexane); Melting point: 164.5–167.2° C. (dec.); $^1$H-NMR (CDCl$_3$) δ: 2.99 (2H,t,J=6.7 Hz), 3.03(3H,d,J=5.0 Hz), 3.87(3H,s), 4.59(2H, t,J=6.9 Hz), 7.00(2H,d,J=8.6 Hz), 7.83(2H,d,J=8.6 Hz), 8.71 (1H,s), 9.44(1H,br). IR (KBr) cm$^{-1}$: 2246,1717,1664,1520, 1275,1250. Mass (m/z): 312 (M$^+$).

Example 51

Preparation of 6-(4-Methoxyphenyl)-4-methylcarbamoyl-2-n-propyl-2H-pyridazin-3-one Using 4-methoxycarbonyl-6-(4-methoxyphenyl)-2-n-propyl-2H-pyridazin-3-one as a starting material, the procedures of Example 43 were repeated likewise, whereby the title compound was obtained in a yield of 85.3%.

Colorless needles (chloroform-hexane); Melting point: 106.5–107.1° C.; $^1$H-NMR (CDCl$_3$) δ: 1.02(3H,t,J=7.3 Hz), 1.85–2.00(2H,m), 3.02(3H,d,J=5.0 Hz), 3.87(3H,s), 4.29 (2H,t,J=7.3 Hz), 6.99(2H,d,J=8.9 Hz), 7.82(2H,d,J=8.9 Hz), 8.66(1H,s), 9.72(1H,br). Mass (m/z): 301 (M$^+$).

Example 52

Preparation of 2-Isopropyl-6-(4-methoxyphenyl)-4-methylcarbamoyl-2H-pyridazin-3-one Using 4-ethoxycarbonyl-2-isopropyl-6-(4-methoxyphenyl)-2H-pyridazin-3-one as a starting material, the procedures of Example 43 were repeated likewise, whereby the title compound was obtained in a yield of 91.9%.

Colorless needles (chloroform-hexane); Melting point: 154.0–154.3° C.; $^1$H-NMR (CDCl$_3$) δ: 1.47(6H,d,J=6.6 Hz), 3.03(3H,d,J=5.0 Hz), 3.87(3H,s), 5.36–5.52(1H,m), 7.00 (2H,d,J=8.9 Hz), 7.85(2H,d,J=8.9 Hz), 8.66(1H,s), 9.77(1H, br). IR (KBr) cm$^{-1}$: 3262,1677,1547,1518,1417,1310,1269, 1250, 1175,1021,831,801. Mass (m/z): 301 (M$^+$).

Example 53

Preparation of 6-(3,4-Dimethoxyphenyl)-2-isobutyl-4-methylcarbamoyl-2H-pyridazin-3-one Using 4-ethoxycarbonyl-6-(3,4-dimethoxyphenyl)-2-isobutyl-2H-pyridazin-3-one as a starting material, the procedures of Example 43 were repeated likewise, whereby the title compound was obtained in a yield of 92.8%.

Slightly yellow needles (chloroform-hexane); Melting point: 111.4–112.6° C.; $^1$H-NMR (CDCl$_3$) δ: 1.01(6H,d,J= 6.6 Hz), 2.28–2.43(1H,m), 3.03(3H,d,J=5.0 Hz), 3.95(3H,s), 3.97(3H,s), 4.16(2H,d,J=7.3 Hz), 6.96(1H,d,J=8.6 Hz), 7.41–7.46(2H,m), 8.68(1H,s), 9.72(1H,br). IR (KBr) cm$^{-1}$: 3276,1683,1585,1551,1512,1257,1227,1171, 1118,1021, 871. Mass (m/z): 345 (M$^+$).

Example 54

Preparation of 6-(3-Fluoro-4-methoxyphenyl)-2-isobutyl-4-methylcarbamoyl-2H-pyridazin-3-one Using 6-(3-fluoro-4-methoxyphenyl)-2-isobutyl-4-methoxycarbonyl-2H-pyridazin-3-one as a starting material, the procedures of Example 43 were repeated likewise, whereby the title compound was obtained in a yield of 88.3%.

Pale yellow needles (chloroform-hexane); Melting point: 153.3–154.9° C.; $^1$H-NMR (CDCl$_3$) δ: 1.00(6H,d,J=6.6 Hz), 2.27–2.43(1H,m), 3.02(3H,d,J=5.0 Hz), 3.95(3H,s), 4.15 (2H,d,J=7.3 Hz), 7.00–7.08(1H,m), 7.55–7.61(1H,m), 7.65–7.72(1H,m), 9.68(1H,br). IR (KBr) cm$^{-1}$: 3248,1684, 1522,1509,1435,1297,1276. Mass (m/z): 333 (M$^+$).

Example 55

Preparation of 6-(3-Chloro-4-methoxyphenyl)-2-isobutyl-4-methylcarbamoyl-2H-pyridazin-3-one Using 6-(3-chloro-4-methoxyphenyl)-2-isobutyl-4-methoxycarbonyl-2H-pyridazin-3-one as a starting material, the procedures of Example 43 were repeated likewise, whereby the title compound was obtained in a yield of 94.3%.

Slightly yellow needles (chloroform-hexane); Melting point: 181.8–183.5° C.; $^1$H-NMR (CDCl$_3$) δ: 1.00(6H,d,J= 6.6 Hz), 2.27–2.43(1H,m), 3.02(3H,d,J=5.0 Hz), 3.97(3H,s), 4.15(2H,d,J=7.3 Hz), 7.01(1H,d,J=8.6 Hz), 7.72(1H,dd,J= 2.3,8.6 Hz), 7.85(1H,d,J=2.3 Hz), 8.64(1H,s), 9.68(1H,br). IR (KBr) cm$^{-1}$: 3248,1685,1546,1509,1410,1294,1264. Mass (m/z): 351 (M$^+$), 349 (M$^+$).

Example 56

Preparation of 2-Isobutyl-4-methylcarbamoyl-6-[4-(methylthio)phenyl]-2H-pyridazin-3-one Using 2-isobutyl-4-methoxycarbonyl-6-[4-(methylthio) phenyl]-2H-pyridazin-3-one as a starting material, the procedures of Example 43 were repeated likewise, whereby the title compound was obtained in a yield of 92.3%.

Slightly yellow needles (chloroform-hexane); Melting point: 129.6–130.6° C.; $^1$H-NMR (CDCl$_3$) δ: 1.00(6H,d,J=

6.6 Hz), 2.27–2.43(1H,m), 2.53(3H,s), 3.02(3H,d,J=4.9 Hz), 4.16(2H,d,J=7.3 Hz), 7.33(2H,d,J=8.7 Hz), 7.80(2H,d,J=8.7 Hz), 8.68(1H,s), 9.69(1H,br). IR (KBr) cm$^{-1}$: 3275,1687, 1624,1575,1506,1400,1394. Mass (m/z): 331 (M$^+$).

Example 57

Preparation of 6-(4-Methoxyphenyl)-2-(3-methyl-2-butenyl)-4-methylcarbamoyl-2H-pyridazin-3-one Using 4-ethoxycarbonyl-6-(4-methoxyphenyl)-2-(3-methyl-2-butenyl)-2H-pyridazin-3-one as a starting material, the procedures of Example 43 were repeated likewise, whereby the title compound was obtained in a yield of 79.0%.

Slightly yellow needles (chloroform-hexane); Melting point: 103.6–104.0° C.; $^1$H-NMR (CDCl$_3$) δ: 1.77(3H,s), 1.88(3H,s), 3.02(3H,d,J=5.0 Hz), 3.87(3H,s), 4.90(2H,d,J= 7.3 Hz), 5.41–5.50(1H,m), 6.99(2H,d,J=8.9 Hz), 7.82(2H, d,J=8.9 Hz), 8.66(1H,s), 9.71(1H,br). IR (KBr) cm$^{-1}$: 3244, 1675,1546,1517,1248,1175,1025,831, 798. Mass (m/z): 327 (M$^+$).

Example 58

Preparation of 6-(4-Methoxyphenyl)-4-methylcarbamoyl-2-(2-pyridylmethyl) carbamoylmethyl-2H-pyridazin-3-one (1) Preparation of 6-(4-methoxyphenyl)-4-methylcarbamoyl-2H-pyridazin-3-one Using 4-ethoxycarbonyl-6-(4-methoxyphenyl)-2H-pyridazin-3-one as a starting material, the procedures of Example 43 were repeated likewise, whereby the title compound was obtained in a yield of 97.9%.

Colorless needles (chloroform-hexane); Melting point: 246.5–246.9° C.; $^1$H-NMR (CDCl$_3$) δ: 3.06(3H,d,J=5.0 Hz), 3.87(3H,s), 7.00(2H,d,J=8.9 Hz), 7.83(2H,d,J=8.9 Hz), 8.74 (1H,s), 9.46(1H,br), 11.89(1H,br). IR (KBr) cm$^{-1}$: 3219, 3142,1675,1568,1518,1257,1226,1184, 1032,832. Mass (m/z): 259 (M$^+$).

(2) Preparation of 2-ethoxycarbonylmethyl-6-(4-methoxyphenyl)- 4-methylcarbamoyl-2H-pyridazin-3-one Using 6-(4-methoxyphenyl)-4-methylcarbamoyl-2H-pyridazin-3-one as a starting material, the procedures or Example 47-(1) were repeated likewise, whereby the title compound was obtained in a yield of 98.5%.

Melting point: 141.0–142.2° C.; $^1$H-NMR (CDCl$_3$) δ: 1.31(3H,t,J=7.3 Hz), 3.01(3H,d,J=5.0 Hz), 3.87(3H,s), 4.28 (2H,q,J=7.3 Hz), 5.02(2H,s), 6.99(2H,d,J=8.9 Hz), 7.81(2H, d,J=8.9 Hz), 8.72(1H,s), 9.47(1H,br). IR (KBr) cm$^{-1}$: 3283, 1735,1691,1508,1259,1226,1169,1028. Mass (m/z): 345 (M$^+$).

(3) Preparation of 6-(4-methoxyphenyl)-4-methylcarbamoyl-2-(2-pyridylmethyl)carbamoylmethyl-2H-pyridazin-3-one In xylene, 2-ethoxycarbonylmethyl-6-(4-methoxyphenyl)-4-methylcarbamoyl-2H-pyridazin-3-one and 2-(aminomethyl)pyridine were refluxed at 150° C. for 7 hours. Post-treatments were conducted as in Example 47-(2), whereby the title compound was obtained in a yield of 44.5%.

Slightly yellow prisms (chloroform-hexane); Melting point: 194.7–195.8° C.; $^1$H-NMR (CDCl$_3$) δ: 3.00(3H,t,J= 5.0 Hz), 3.87(3H,s), 4.62(2H,d,J=5.0 Hz), 5.06(2H,s), 6.98 (2H,d,J=8.9 Hz), 7.15–7.21(1H,m), 7.33–7.38(1H,m), 7.35 (1H,brt,J=5.0 Hz), 7.61–7.69(1H,m), 7.83(2H,d,J=8.9 Hz), 8.43–8.47(1H,m), 8.72(1H,s), 9.49(1H,br). IR (KBr) cm$^{-1}$: 3283,1681,1664,1518,1251,1167,1024. Mass (m/z): 407 (M$^+$).

Example 59

Preparation of 2-(2-Hydroxyethyl)carbamoylmethyl-6-(4-methoxyphenyl)-4-methylcarbamoyl-2H-pyridazin-3-one In methanol, 2-ethoxycarbonylmethyl-6-(4-methoxyphenyl)-4-methylcarbamoyl-2H-pyridazin-3-one and 2-aminoethanol were heated under reflux for 4 hours. Post-treatments were conducted as in Example 43, whereby the title compound was obtained in a yield of 91.0%.

Colorless fine needles (chloroform-hexane); Melting point: 240.2–241.2° C.; $^1$H-NMR (CDCl$_3$) δ: 2.34(1H,t,J= 5.7 Hz), 2.98(3H,d,J=5.1 Hz), 3.46–3.53(2H,m), 3.72–3.80 (2H,m), 3.87(3H,s), 4.98(2H,s), 6.52(1H,br), 6.99(2H,d,J= 8.9 Hz), 7.82(2H,d,J=8.9 Hz), 8.70(1H,s), 9.42(1H,br). IR (KBr) cm$^{-1}$: 3405,3288,1675,1657,1574,1554,1519,1508, 1416,1402,1253,1074,835. Mass (m/z): 360 (M$^+$).

Example 60

Preparation of 6-(4-Methoxyphenyl)-4-methylcarbamoyl-2-[4-(methylthio) phenylcarbamoylmethyl]-2H-pyridazin-3-one Using 4-methoxycarbonyl-6-(4-methoxyphenyl)-2-[4-(methylthio)phenylcarbamoylmethyl]-2H-pyridazin-3-one as a starting material, the procedures of Example 43 were repeated likewise, whereby the title compound was obtained in a yield of 92.2%.

Slightly yellow prisms (chloroform-hexane); Melting point: 230.6–232.0° C.; $^1$H-NMR (CDCl$_3$) δ: 2.46(3H,s), 3.03(3H,d,J=5.0 Hz), 3.87(3H,s), 3.98(3H,s), 5.10(2H,s), 6.99(2H,d,J=9.1 Hz), 7.23(2H,d,J=8.7 Hz), 7.46(2H,d,J=8.7 Hz), 7.84(2H,d,J=9.1 Hz), 8.16(1H,br), 8.74(1H,s), 9.42 (1H,br). IR (KBr) cm$^{-1}$: 3290,3236,1680,1539,1518,1254. Mass (m/z): 438 (M$^+$).

Example 61

Preparation of 2-Cyclopropylmethyl-6-(4-methoxyphenyl)-4-methylcarbamoyl-2H-pyridazin-3-one Using 2-cyclopropylmethyl-4-ethoxycarbonyl-6-(4-methoxyphenyl)-2H-pyridazin-3-one as a starting material, the procedures of Example 43 were repeated likewise, whereby the title compound was obtained in a yield of 89.1%.

Slightly yellow needles (methanol-diethyl ether); Melting point: 136.6–137.5° C.; $^1$H-NMR (CDCl$_3$) δ: 0.47–0.62(4H, m), 1.39–1.49(1H,m), 3.03(3H,d,J=5.1 Hz), 3.87(3H,s), 4.18(2H,d,J=7.3 Hz), 7.00(2H,d,J=8.9 Hz), 7.83(2H,d,J=8.9 Hz), 8.67(1H,s), 9.72(1H,brd,J=5.1 Hz). IR (KBr) cm$^{-1}$ 3339,1684,1627,1609,1518,1252,1183,1027, 845,836,811. Mass (m/z): 313 (M$^+$).

Example 62

Preparation of 2-Cyclopropylmethyl-6-(3,4-dimethoxyphenyl)-4-methylcarbamoyl-2H-pyridazin-3-one Using 2-cyclopropylmethyl-6-(3,4-dimethoxyphenyl)-4-methoxycarbonyl-2H-pyridazin-3-one as a starting material, the procedures of Example 43 were repeated likewise, whereby the title compound was obtained in a yield of 95.3%.

Pale yellow needles (chloroform-hexane); Melting point: 156.1–154.1° C.; $^1$H-NMR (CDCl$_3$) δ: 0.47–0.65(4H,m), 1.38–1.51(1H,m), 3.03(3H,d,J=5.0 Hz), 3.95(3H,s), 3.97 (3H,s), 4.19(2H,d,J=7.3 Hz), 6.96(1H,d,J=8.9 Hz), 7.43(1H, d,J=2.3 Hz), 7.44(1H,dd,J=2.3,8.9 Hz), 8.69(1H,s), 9.72 (1H,br). IR (KBr) cm$^{-1}$: 3267,1686,1552,1520,1508,1422, 1255,1232, 1034. Mass (m/z): 343 (M$^+$).

Example 63

Preparation of 2-Cyclopropylmethyl-6-(3-fluoro-4-methoxyphenyl)-4-methylcarbamoyl-2H-pyridazin-3-one Using 2-cyclopropylmethyl-6-(3-fluoro-4-methoxyphenyl)-4-methoxycarbonyl-2H-pyridazin-3-one as a starting material, the procedures of Example 43 were repeated likewise, whereby the title compound was obtained in a yield of 90.3%.

Pale yellow needles (chloroform-hexane); Melting point: 139.6–140.7° C.; $^1$H-NMR (CDCl$_3$) δ: 0.45–0.64(4H,m), 1.36–1.51(1H,m), 3.03(3H,d,J=5.0 Hz), 3.96(3H,s), 4.18 (2H,d,J=7.3 Hz), 7.01–7.08(1H,m), 7.56–7.61(1H,m), 7.65–7.72(1H,m), 8.66(1H,s), 9.69(1H,br). IR (KBr) cm$^{-1}$: 3281,1688,1523,1510,1436,1299,1275. Mass (m/z): 331 (M$^+$).

Example 64

Preparation of 6-(3-Chloro-4-methoxyphenyl)- 2-cyclopropylmethyl-4-methylcarbamoyl-2H-pyridazin-3-one Using 6-(3-chloro-4-methoxyphenyl)-2-cyclopropylmethyl-4-methoxycarbonyl-2H-pyridazin-3-one as a starting material, the procedures of Example 43 were repeated likewise, whereby the title compound was obtained in a yield of 90.3%.

Slightly yellow needles (chloroform-hexane); Melting point: 172.4–173.4° C.; $^1$H-NMR (CDCl$_3$) δ: 0.46–0.64(4H, m), 1.38–1.50(1H,m), 3.03(3H,d,J=5.3 Hz), 3.97(3H,s), 4.18(2H,d,J=7.3 Hz), 7.02(1H,d,J=8.8 Hz), 7.73(1H,dd,J= 2.3,8.8 Hz), 7.95(1H,d,J=2.3 Hz), 8.65(1H,s), 9.68(1H,br). IR (KBr) cm$^{-1}$: 3244,1684,1552,1509,1410,1294,1264. Mass (m/z): 349 (M$^+$), 347 (M$^+$).

Example 65

Preparation of 2-Cyclopropylmethyl-4-methylcarbamoyl-6-[4-(methylthio)phenyl]-2H-pyridazin-3-one Using 2-cyclopropylmethyl-4-methoxycarbonyl-6-[4-(methylthiophenyl)]-2H-pyridazin-3-one as a starting material, the procedures of Example 43 were repeated likewise, whereby the title compound was obtained in a yield of 94.3%.

Yellow prisms (chloroform-hexane); Melting point: 116.5–118.0° C.;. $^1$H-NMR (CDCl$_3$) δ: 0.45–0.64(4H,m), 1.36–1.51(1H,m), 2.53(3H,s), 3.03(3H,d,J=4.9 Hz), 4.18 (2H,d,J=7.3 Hz), 7.33(2H,d,J=8.7 Hz), 7.80(2H,d,J=8.7 Hz), 8.69(1H,s), 9.69(1H,br). IR (KBr) cm$^{-1}$: 3275,1686,1625, 1595,1545,1505,1400. Mass (m/z): 329 (M$^+$).

Example 66

Preparation of 2-Cyclopropylmethyl-4-ethylcarbamoyl-6-(4-methoxyphenyl)-2H-pyridazin-3-one In methanol, 2-cyclopropylmethyl-4-ethoxycarbonyl-6-(4-methoxyphenyl)-2H-pyridazin-3-one and 70% aqueous solution of ethylamine were reacted at 70° C. for 4 hours. Post-treatments were conducted as in Example 43, whereby the title compound was obtained in a yield of 80.2%.

Colorless needles (chloroform-hexane); Melting point: 136.3–136.9° C.; $^1$H-NMR (CDCl$_3$) δ: 0.47–0.64(4H,m), 1.28(3H,t,J=7.3 Hz), 1.37–1.53(1H,m), 3.51(2H,d,J=8.9 Hz), 3.87(3H,s), 4.18(2H,d,J=7.3 Hz), 7.00(2H,d,J=8.9 Hz), 7.83(2H,d,J=8.9 Hz), 8.68(1H,s), 9.76(1H,brt,J=5.9 Hz). IR (KBr) cm$^{-1}$: 3211,1679,1622,1610,1517,1417,1249,1182, 1033,834. Mass (m/z): 327 (M$^+$).

Example 67

Preparation of 2-Cyclopropylmethyl-6-(4-methoxyphenyl)-4-n-propylcarbamoyl-2H-pyridazin-3-one Using 2-cyclopropylmethyl-4-ethoxycarbonyl-6-(4-methoxyphenyl)-2H-pyridazin-3-one and an n-propylaminemethanol solution as starting materials, the procedures of Example 43 were repeated likewise, whereby the title compound was obtained in a yield of 65.4%.

Colorless needles (chloroform-hexane); Melting point: 101.3–101.6° C.; $^1$H-NMR (CDCl$_3$) δ: 0.46–0.63(4H,m), 1.01(3H,t,J=7.3 Hz), 1.39–1.52(1H,m), 1.60–1.76(2H,m), 3.44(2H,d,J=6.9 Hz), 3.87(3H,s), 4.18(2H,d,J=7.3 Hz), 7.00 (2H,d,J=8.9 Hz), 7.83(2H,d,J=8.9 Hz), 8.68(1H,s), 9.81(1H, br). IR (KBr) cm$^{-1}$: 3216,1679,1622,1608,1517,1416,1252, 1182, 1033,833. Mass (m/z): 341 (M$^+$).

Example 68

Preparation of 4-Benzylcarbamoyl-2-cyclopropylmethyl-6-(4-methoxyphenyl)-2H-pyridazin-3-one Benzylamine (318 mg, 2.97 mmol) was added to a solution of 2-cyclopropylmethyl-4-ethoxycarbonyl-6-( 4-methoxyphenyl)-2H-pyridazin-3-one (65 mg, 0.20 mmol) in xylene (1 ml), followed by stirring at 140° C. for 24 hours. The reaction mixture was added with ethyl acetate (20 ml), washed successively with 2N hydrochloric acid (20 ml) and brine (20 ml), and then dried over anhydrous sodium sulfate. The solvent was distilled off and the residue (98 mg) was crystallized from chloroform-hexane, whereby the title compound (72 mg, 93.4%) was obtained as pale yellow fine needles.

Melting point: 119.7–120.1° C.; $^1$H-NMR (CDCl$_3$) δ: 0.44–0.62(4H,m), 1.37–1.50(1H,m), 3.89(3H,s), 4.16(2H,d, J=7.3 Hz), 4.67(2H,d,J=5.9 Hz), 7.00(2H,d,J=8.8 Hz), 7.24–7.41(5H,m), 7.83(2H,d,J=8.8 Hz), 8.71(1H,s), 10.18 (1H,brt,J=5.9 Hz). IR (KBr) cm$^{-1}$: 3210,1675,1622,1610, 1516,1274,1250,1185, 1028,838. Mass (m/z): 389 (M$^+$).

Example 69

Preparation of 2-Cyclopropylmethyl-6-(4-methoxyphenyl)-4-(2-pyridylmethyl)carbamoyl-2H-pyridazin-3-one In xylene, 2-cyclopropylmethyl-4-ethoxycarbonyl-6-(4-methoxyphenyl)-2H-pyridazin-3-one and 2-(aminomethyl) pyridine were reacted at 140° C. for 1 hour. Post-treatments were conducted as in Example 58-(3), whereby the title compound was obtained in a yield of 84.2%.

Slightly yellow needles (chloroform-hexane); Melting point: 98.6–99.3° C.; $^1$H-NMR (CDCl$_3$) δ: 0.46–0.63(4H, m), 1.39–1.55(1H,m), 3.87(3H,s), 4.20(2H,d,J=7.3 Hz), 4.83(2H,d,J=5.4 Hz), 7.00(2H,d,J=9.3 Hz), 7.17–7.23(1H, m), 7.32–7.37(1H,m), 7.63–7.71(1H,m), 7.83(2H,d,J=9.3 Hz), 8.61–8.65(1H,m), 8.71(1H,s), 10.55(1H,brt,J=5.4 Hz). IR (KBr) cm$^{-1}$: 3252,1683,1624,1609,1516,1417,1273, 1253, 1181,1022,834. Mass (m/z): 390 (M$^+$).

Example 70

Preparation of 2-Cyclopropylmethyl-6-(4-methoxyphenyl)-4-(4-pyridyl)carbamoyl-2H-pyridazin-3-one

Sodium hydride (9 mg, 0.38 mmol; used after removal of oil by washing it with toluene) was added to a solution of 4-aminopyridine (34 mg, 0.361 mmol) in dimethylsulfoxide (0.5 ml), followed by stirring at room temperature for 15 minutes. Thereafter, 2-cyclopropylmethyl-4-ethoxycarbonyl-6-(4-methoxyphenyl)- 2H-pyridazin-3-one (80 mg, 0.24 mmol) was added, followed by stirring at the same temperature for 30 minutes. The reaction mixture was added with ethyl acetate (30 ml), washed successively with water (20 ml) and brine (20 ml), and then dried over anhydrous sodium sulfate. The solvent was distilled off and the residue (61 mg) was separated and purified by silica gel preparative chromatography [developer: chloroform/methanol (10/1)], whereby the title compound (61 mg, 61.1%) was obtained.

Pale yellow fine needles (chloroform-hexane); Melting point: 181.3–181.5° C.; $^1$H-NMR (CDCl$_3$) δ: 0.49–0.68(4H, m), 1.40–1.56(1H,m), 3.89(3H,s), 4.24(2H,d,J=7.3 Hz), 7.02(2H,d,J=8.9 Hz), 7.69(2H,d,J=6.3 Hz), 7.85(2H,d,J=8.9 Hz), 8.57(2H,d,J=6.3 Hz), 8.75(1H,s), 12.25(1H,br). IR (KBr) cm$^{-1}$: 1697,1629,1607,1517,1273,1254,1184,1017, 835, 813,805,791. Mass (m/z): 376 (M$^+$).

Example 71

Preparation of 2-Cyclopropylmethyl-6-(4-methoxyphenyl)-4-phenylcarbamoyl-2H-pyridazin-3-one

2-Cyclopropylmethyl-4-ethoxycarbonyl-6-(4-methoxyphenyl)-2H-pyridazin-3-one and aniline were processed as in Example 70, whereby the title compound was obtained in a yield of 12.2%.

Pale yellow fine needles (chloroform-hexane); Melting point: 162.8–163.3° C. $^1$H-NMR (CDCl$_3$) δ: 0.49–0.67(4H, m), 1.41–1.68(1H,m), 3.88(3H,s), 4.23(2H,d,J=7.3 Hz), 7.01(2H,d,J=8.9 Hz), 7.13–7.20(1H,m), 7.34–7.42(2H,m), 7.75–7.81(2H,m), 7.85(2H,d,J=8.9 Hz), 8.77(1H,s), 12.00 (1H,br). IR (KBr) cm$^{-1}$: 3189,1687,1602,1518,1274,1254, 1184,1025, 834,804,791. Mass (m/z): 375 (M$^+$).

Example 72

Preparation of 2-Cyclopentylmethyl-6-(4-methoxyphenyl)-4-methylcarbamoyl-2H-pyridazin-3-one

Using 2-cyclopentylmethyl-4-ethoxycarbonyl-6-(4-methoxyphenyl)-2H-pyridazin-3-one as a starting material, the procedures of Example 43 were repeated likewise, whereby the title compound was obtained in a yield of 75.2%.

Colorless needles (chloroform-hexane); Melting point: 107.4–107.8° C.; $^1$H-NMR (CDCl$_3$) δ: 1.30–1.45(2H,m), 1.50–1.82(6H,m), 2.47–2.64(1H,m), 3.02(3H,d,J=5.0 Hz), 3.87(3H,s), 4.27(2H,d,J=7.6 Hz), 7.00(2H,d,J=8.9 Hz), 7.83 (2H,d,J=8.9 Hz), 8.66(1H,s), 9.74(1H,br). IR (KBr) cm$^{-1}$: 3218,1679,1624,1611,1560,1550,1517,1414, 1249,1188, 1138,1030,844,802. Mass (m/z): 341 (M$^+$).

Example 73

Preparation of 2-Cyclopentylmethyl-4-ethylcarbamoyl-6-(4-methoxyphenyl)-2H-pyridazin-3-one

In methanol, 2-cyclopentylmethyl-4-ethoxycarbonyl-6-(4-methoxyphenyl)-2H-pyridazin-3-one and a 70% aqueous solution of ethylamine were processed as in Example 43, whereby the title compound was obtained in a yield of 82.2%.

Colorless needles (chloroform-hexane); Melting point: 129.1–129.4° C.; $^1$H-NMR (CDCl$_3$) δ: 1.27(3H,t,J=7.3 Hz), 1.34–1.45(2H,m), 1.50–1.82(6H,m), 2.48–2.65(1H,m), 3.44–3.56(2H,m), 3.87(3H,s), 4.27(2H,d,J=7.6 Hz), 6.99 (2H,d,J=8.9 Hz), 7.82(2H,d,J=8.9 Hz), 8.67(1H,s), 9.76(1H, br). IR (KBr) cm$^{-1}$: 3242,1683,1623,1609,1518,1417,1311, 1249, 1181,1033,834,800. Mass (m/z): 355 (M$^+$).

Example 74

Preparation of 2-Cyclopentylmethyl-6-(4-methoxyphenyl)-4-n-propylcarbamoyl-2H-pyridazin-3-one

Using 2-cyclopentylmethyl-4-ethoxycarbonyl-6-(4-methoxyphenyl)-2H-pyridazin-3-one as a starting material, the procedures of Example 67 were repeated likewise, whereby the title compound was obtained in a yield of 79.1%.

Colorless needles (chloroform-hexane); Melting point: 109.9–110.2° C.; $^1$H-NMR (CDCl$_3$) δ: 1.01(3H,t,J=7.3 Hz), 1.31–1.46(2H,m), 1.50–1.83(8H,m), 2.48–2.65(1H,m), 3.44 (2H,q,J=6.4 Hz), 3.87(3H,s), 4.27(2H,d,J=7.6 Hz), 7.00(2H, d,J=8.9 Hz), 7.82(2H,d,J=8.9 Hz), 8.67(1H,s), 9.81(1H,br). IR (KBr) cm$^{-1}$: 3246,1683,1544,1519,1417,1311,1273, 1252, 1030,835,797. Mass (m/z): 369 (M$^+$).

Example 75

Preparation of 4-Benzylcarbamoyl-2-cyclopentylmethyl-6-(4-methoxyphenyl)-2H-pyridazin-3-one

In xylene, 2-cyclopentylmethyl-4-ethoxycarbonyl-6-(4-methoxyphenyl)-2H-pyridazin-3-one and benzylamine were reacted at 140° C. for 2 hours. Post-treatments were conducted as in Example 68, whereby the title compound was obtained in a yield of 78.5%.

Pale yellow needles (chloroform-hexane); Melting point: 107.6–108.1° C.; $^1$H-NMR (CDCl$_3$) δ: 1.28–1.44(2H,m), 1.48–1.81(6H,m), 2.46–2.63(1H,m), 3.87(3H,s), 4.25(2H,d, J=7.6 Hz), 4.66(2H,d,J=5.9 Hz), 7.00(2H,d,J=8.9 Hz), 7.23–7.40(5H,m), 7.82(2H,d,J=8.9 Hz), 8.70(1H,s), 10.18 (1H,brt,J=5.9 Hz). IR (KBr) cm$^{-1}$: 3251,1677,1624,1611, 1517,1386,1259,1179, 1136,1033,831. Mass (m/z): 417 (M$^+$).

Example 76

Preparation of 2-Cyclopentylmethyl-6-(4-methoxyphenyl)-4-(2-pyridylmethyl)carbamoyl-2H-pyridazin-3-one

Using 2-cyclopentylmethyl-4-ethoxycarbonyl-6-(4-methoxyphenyl)-2H-pyridazin-3-one as a starting material, the procedures of Example 58-(3) were repeated likewise, whereby the title compound was obtained in a yield of 88.6%.

Colorless needles (chloroform-hexane); Melting point: 126.6–127.5° C.; $^1$H-NMR (CDCl$_3$) δ: 1.30–1.46(2H,m), 1.49–1.82(6H,m), 2.50–2.67(1H,m), 3.87(3H,s), 4.29(2H,d, J=7.6 Hz), 4.82(2H,d,J=5.3 Hz), 7.00(2H,d,J=8.9 Hz), 7.16–7.23(1H,m), 7.31–7.36(1H,m), 7.62–7.70(1H,m), 7.83 (2H,d,J=8.9 Hz), 8.60–8.64(1H,m), 8.69(1H,s), 10.53(1H, brt,J=5.3 Hz). IR (KBr) cm$^{-1}$: 3255,1673,1624,1610,1511, 1457,1433,1259, 1251,1028,832. Mass (m/z): 418 (M$^+$).

Example 77

Preparation of 4-Benzylcarbamoyl-6-(4-methoxyphenyl)-2-methyl-2H-pyridazin-3-one In xylene, 4-ethoxycarbonyl-6-(4-methoxyphenyl)-2-methyl-2H-pyridazin-3-one and benzylamine were reacted at 140° C. for 1 hour. Post-treatments were conducted as in Example 68, whereby the title compound was obtained in a yield of 94.2%.

Pale yellow needles (chloroform-hexane); Melting point: 144.8–145.8° C.; $^1$H-NMR (CDCl$_3$) δ: 3.87(3H,s), 3.94(3H, s), 4.67(2H,d,J=5.9 Hz), 7.00(2H,d,J=8.9 Hz), 7.23–7.40 (5H,m), 7.82(2H,d,J=8.9 Hz), 8.71(1H,s), 10.13(1H,brt,J= 5.9 Hz). IR (KBr) cm$^{-1}$: 3244,1679,1624,1583,1516,1455, 1251,1182, 1030,836. Mass (m/z): 349 (M$^+$).

Example 78

Preparation of 6-(4-Methoxyphenyl)-2-methyl-4-(2-pyridylmethyl)carbamoyl-2H-pyridazin-3-one Using 4-ethoxycarbonyl-2-methyl-6-(4-methoxyphenyl)-2H-pyridazin-3-one as a starting material, the procedures of Example 58-(3) were repeated likewise, whereby the title compound was obtained in a yield of 86.1%.

Pale yellow needles (chloroform-hexane); Melting point: 122.4–122.9° C.; $^1$H-NMR (CDCl$_3$) δ: 3.87(3H,s), 3.97(3H, s), 4.82(2H,d,J=5.6 Hz), 7.00(2H,d,J=8.9 Hz), 7.17–7.23 (1H,m), 7.31–7.36(1H,m), 7.63–7.71(1H,m), 7.82(2H,d,J= 8.9 Hz), 8.61–8.65(1H,m), 8.71(1H,s), 10.53(1H,brt,J=5.6 Hz). IR (KBr) cm$^{-1}$: 3238,1683,1625,1613,1516,1435,1248, 1180, 1035,836. Mass (m/z): 350 (M$^+$).

Example 79

Preparation of 2-Benzyl-6-(4-methoxyphenyl)-4-methylcarbamoyl-2H-pyridazin-3-one and 2-benzyl-4-dimethylcarbamoyl-6-(4-methoxyphenyl)-2H-pyridazin-3-one To 40% aqueous solution of dimethylamine (3 ml), 2-benzyl-4-ethoxycarbonyl-6-(4-methoxyphenyl)-2H-pyridazin-3-one (71 mg, 0.19 mmol) was added, followed by stirring at room temperature for 17 hours. The solvent was distilled off, and the residue (74 mg) was separated and purified by silica gel preparative chromatography [developer: chloroform/methanol (20/1)]. From fractions of large Rf values, the title compound [2-benzyl-6-(4-methoxyphenyl)-4-methylcarbamoyl-2H-pyridazin-3-one] (29.4 mg, 44.7%) was obtained. Pale yellow needles (chloroform-diethyl ether)

Melting point: 181.7–182.1° C.; $^1$H-NMR (CDCl$_3$) δ: 3.00(3H,d,J=4.9 Hz), 3.87(3H,s), 5.47(2H,s), 7.00(2H,d,J= 8.8 Hz), 7.30–7.36(2H,m), 7.47(2H,d,J=6.4 Hz), 7.84(2H, d,J=9.3 Hz), 8.67(1H,s), 9.65(1H,br). IR (KBr) cm$^{-1}$: 3270, 1680,1607,1518,1408,1251,1026,850, 743.

From fractions of small Rf values, the title compound [2-benzyl-6-(4-methoxyphenyl)-4-(dimethylcarbamoyl)-2H-pyridazin-3-one] (10.5 mg, 14.8%) was also obtained.

Colorless fine needles (chloroform-diethyl ether-hexane); Melting point: 183.0–184.0° C.; $^1$H-NMR (CDCl$_3$) δ: 2.96 (3H,s), 3.11(3H,s), 3.86(3H,s), 5.41(2H,s), 6.97(2H,d,J=9.0 Hz), 7.26–7.33(3H,m), 7.50(2H,dd,J=2.0,8.0 Hz), 7.72(2H, d,J=9.0 Hz), 7.74(1H,s). IR (KBr) cm$^{-1}$: 1654,1641,1610, 1521,1250,1025,832.

Example 80

Preparation of 6-(4-Methoxyphenyl)-4-methylcarbamoyl-2-(4-nitrobenzyl)-2H-pyridazin-3-one Using 4-methoxycarbonyl-6-(4-methoxyphenyl)-2-(4-nitrobenzyl)-2H-pyridazin-3-one as a starting material, the procedures of Example 43 were repeated likewise, whereby the title compound was obtained in a yield of 92.2%.

Yellow needles (chloroform-hexane); Melting point: 198.8–199.4° C.; $^1$H-NMR (CDCl$_3$) δ: 3.01(3H,d,J=5.0 Hz), 3.88(3H,s), 5.54(2H,s), 7.01(2H,d,J=9.2 Hz), 7.62(2H,d,J= 8.9 Hz), 7.82(2H,d,J=9.2 Hz), 8.22(2H,d,J=8.9 Hz), 8.71 (1H,s), 9.48(1H,br). IR (KBr) cm$^{-1}$: 3282,1680,1515,1344, 1254. Mass (m/z): 394 (M$^+$).

Example 81

Preparation of 6-(4-Methoxyphenyl)-4-methylcarbamoyl-2-[4-(3-pyridylcarbonylamino)benzyl]-2H-pyridazin-3-one Using 4-methoxycarbonyl-4-methylcarbamoyl-2-[4-(3-pyridylcarbonylamino)benzyl]-2H-pyridazin-3-one as a starting material, the procedures of Example 43 were repeated likewise, whereby the title compound was obtained in a yield of 92.7%.

Slightly yellow fine needles (chloroform-hexane); Melting point: 226.7–227.6° C. (dec.); $^1$H-NMR (CDCl$_3$) δ: 3.00(3H,d,J=5.0 Hz), 3.87(3H,s), 5.46(2H,s), 7.00(2H,d,J= 9.0 Hz), 7.44(1H,ddd,J=1.1,4.6,6.8 Hz), 7.53(2H,d,J=8.5 Hz), 7.63(2H,d,J=8.5 Hz), 7.83(2H,d,J=9.0 Hz), 7.87(1H, br), 8.19(2H,ddd,J=1.6,1.7,8.1 Hz), 8.66(1H,s), 8.78(1H,dd, J=1.7,4.6 Hz), 9.08(1H,dd,J=1.1,1.6 Hz), 9.62(1H,brq,J=5.0 Hz). IR (KBr) cm$^{-1}$: 3339,1679,1601,1535,1515,1412,1317, 1253. Mass (m/z): 469 (M$^+$).

Example 82

Preparation of 2-(2,4-Dichlorobenzyl)-6-(4-methoxy-phenyl)-4-methylcarbamoyl-2H-pyridazin-3-one Using 2-(2,4-dichlorobenzyl)-4-ethoxycarbonyl-6-(4-methoxyphenyl)-2H-pyridazin-3-one as a starting material, the procedures of Example 43 were repeated likewise, whereby the title compound was obtained in a yield of 97.4%.

Fine pale yellow needles (chloroform-hexane); Melting point: 154.2–156.2° C.; $^1$H-NMR (CDCl$_3$) δ: 3.01(3H,d,J= 5.0 Hz), 3.86(3H,s), 5.57(2H,s), 6.98(2H,d,J=8.9 Hz), 7.16 (1H,d,J=8.3 Hz), 7.22(1H,dd,J=2.0,8.3 Hz), 7.45(1H,d,J= 2.0 Hz), 7.79(2H,d,J=8.9 Hz), 8.72(1H,s), 9.54(1H,br). IR (KBr) cm$^{-1}$: 3288,1683,1629,1610,1592,1474,1516,1411, 1255,1165,834. Mass (m/z): 421 (M$^+$), 419 (M$^+$), 417 (M$^+$).

Example 83

Preparation of 6-(4-Methoxyphenyl)-4-methylcarbamoyl-2-(3-pyridylmethyl)-2H-pyridazin-3-one Using 4-methoxycarbonyl-6-(4-methoxyphenyl)-2-(3-pyridylmethyl)-2H-pyridazin-3-one as a starting material, the procedures of Example 43 were repeated likewise, whereby the title compound was obtained in a yield of 87.7%.

Slightly yellow needles (chloroform-hexane); Melting point: 153.8–154.3° C. (dec.); $^1$H-NMR (CDCl$_3$) δ: 3.01 (3H,d,J=5.0 Hz), 3.87(3H,s), 5.47(2H,s), 7.00(2H,d,J=9.1 Hz), 7.25–7.32(1H,m), 7.78–7.85(3H,m), 8.56–8.59(1H,m), 8.67(1H,s), 8.77–8.80(1H,m), 9.55(1H,br). IR (KBr) cm$^{-1}$: 3253,1679,1547,1518,1417,1316,1251,1028, 833,796. Mass (m/z): 350 (M$^+$).

Example 84

Preparation of 2-Cinnamyl-6-(4-methoxyphenyl)-4-methylcarbamoyl-2H-pyridazin-3-one Using 2-cinnamyl-4-ethoxycarbonyl-6-(4-methoxyphenyl)-2H-pyridazin-3-one as a starting material, the procedures of Example 43 were repeated likewise, whereby the title compound was obtained in a yield of 100%.

Pale yellow prisms (chloroform-diethyl ether-hexane); Melting point: 160.0–161.0° C.; $^1$H-NMR (CDCl$_3$) δ: 3.02 (3H,d,J=5.1 Hz), 3.86(3H,s), 5.07(2H,dd,J=1.2,6.6 Hz), 6.43(1H,td,J=6.6,15.8 Hz), 6.73(1H,d,J=15.9 Hz), 6.99(2H, d,J=8.8 Hz), 7.27(2H,d,J=8.6 Hz), 7.23–7.34(3H,m), 7.40 (2H,dd,J=1.2,8.1 Hz), 7.83(2H,d,J=9.0 Hz), 8.68(1H,s), 9.66(1H,brs). IR (KBr) cm$^{-1}$: 3245,1686,1611,1516,1024, 835.

Example 85

Preparation of 2-(4-Chlorocinnamyl)-6-(4-methoxyphenyl)-4-methylcarbamoyl-2H-pyridazin-3-one Using 2-(4-chlorocinnamyl-4-ethoxycarbonyl-6-(4-methoxyphenyl)-2H-pyridazin-3-one as a starting material, the procedures of Example 43 were repeated likewise, whereby the title compound was obtained in a yield of 93.3%.

Pale yellow fine needles (chloroform-hexane); Melting point: 184.2–185.4° C.; $^1$H-NMR (CDCl$_3$) δ: 3.03(3H,d,J= 4.6 Hz), 3.87(3H,s), 5.06(2H,d,J=6.6 Hz), 6.40(1H,td,J=6.6, 15.8 Hz), 6.67(1H,d,J=15.8 Hz), 7.00(2H,d,J=8.6 Hz), 7.27 (2H,d,J=8.6 Hz), 7.33(2H,d,J=8.6 Hz), 7.84(2H,d,J=8.6 Hz), 8.69(1H,s), 9.63(1H,brd,J=4.6 Hz). IR (KBr) cm$^{-1}$: 3246, 1677,1550,1519,1491,1402,1260,1186, 1158, 1029,841. Mass (m/z): 411 (M$^+$), 409 (M$^+$).

Example 86

Preparation of 4-Carboxy-2-(4-chlorocinnamyl)-6-(4-methoxyphenyl)-2H-pyridazin-3-one To a suspension of 2-(4-chlorocinnamyl)-4-methoxycarbonyl-6-(4-methoxyphenyl)-2H-pyridazin-3-one (1.35 g, 3.29 mmol) in methanol (50 ml), a 4N aqueous solution of sodium hydroxide (20 ml) was added at room temperature, followed by stirring at the same temperature for 30 minutes. The methanol was distilled off under reduced pressure, and water (100 ml) was added to the residue. The mixture was acidified with hydrochloric acid under ice-water cooling, followed by extraction with chloroform. The organic layer was washed with brine and then dried over anhydrous sodium sulfate. The solvent was distilled off, whereby the title compound (1.30 g, 99.7%) was obtained as yellow crystals.

Melting point: 222.6–224.0° C. (dec.); $^1$H-NMR (CDCl$_3$) δ: 3.88(3H,s), 5.10(2H,d,J=6.8 Hz), 6.40(1H,td,J=6.8,15.6 Hz), 6.74(1H,d,J=15.6 Hz), 7.01(2H,d,J=8.8 Hz), 7.34(2H, d,J=8.8 Hz), 7.81(2H,d,J=8.8 Hz), 8.65(1H,s), 14.10(1H, brd). IR (KBr) cm$^{-1}$: 1743,1630,1609,1561,1518,1475, 1420,1252, 1029,900,837,814. Mass (m/z): 398 (M$^+$), 396 (M$^+$).

Example 87

Preparation of 2-(4-Chlorocinnamyl)-4-ethoxycarbonylamino-6-(4-methoxyphenyl)-2H-pyridazin-3-one To a suspension of 4-carboxy-2-(4-chlorocinnamyl)-6-(4-methoxyphenyl)-2H-pyridazin-3-one (657 mg, 1.66 mmol) in benzene (15 ml), triethylamine (168 mg, 1.66 mmol) and diphenylphosphorylazide (456 mg, 1.66 mmol) were added at room temperature. The mixture was stirred at the same temperature for 30 minutes and then heated under reflux at 100° C. for 30 minutes. Ethanol (20 ml) was then added to the reaction mixture, followed by heating under reflux at 100° C. for 15 hours. The solvent was distilled off under reduced pressure, and the residue was separated and purified by chromatography on a silica gel column [silica gel: 50 g, hexane/ethyl acetate (3/1)]. Crystallization was conducted from chloroform-hexane, whereby the title compound (327 mg, 44.9%) was obtained as slightly yellow fine needles.

Melting point: 171.2–172.1° C. $^1$H-NMR (CDCl$_3$) δ: 1.34(3H,t,J=7.1 Hz), 3.86(3H,s), 4.28(2H,q,J=7.1 Hz), 4.99 (2H,dd,J=1.0,6.3 Hz), 6.40(1H,td,J=6.3,15.9 Hz), 6.65(1H, td,J=1.0,15.9 Hz), 6.96(2H,d,J=8.8 Hz), 7.26(2H,d,J=8.6 Hz), 7.31(2H,d,J=8.6 Hz), 7.78(2H,d,J=8.8 Hz), 8.08(1H, brs), 8.26(1H,s). IR (KBr) cm$^{-1}$: 3224,1727,1642,1606, 1540,1518,1491,1256,1225,1177,830. Mass (m/z): 441 (M$^+$), 439 (M$^+$).

Example 88

Preparation of 2-(4-chlorocinnamyl)-6-(4-methoxyphenyl)-4-isopropoxycarbonylamino-2H-pyridazin-3-one Using 4-carboxy-2-(4-chlorocinnamyl-6-(4-methoxyphenyl)-2H-pyridazin-3-one as a starting material, the procedures of Example 87 were repeated likewise in isopropyl alcohol, whereby the title compound was obtained in a yield of 41.4%.

Pale yellow fine needles (chloroform-hexane)

Melting point: 123.9–127.4° C. $^1$H-NMR (CDCl3) δ: 1.33(6H,d,J=6.4 Hz), 3.86(3H,s), 4.97–5.10(3H,m), 6.40 (1H,td,J=6.4,15.9 Hz), 6.64(1H,td,J=1.2,15.9 Hz), 6.96(2H, d,J=8.9 Hz), 7.29(2H,d,J=8.9 Hz), 7.30(2H,d,J=8.9 Hz), 7.30(2H,d,J=8.9 Hz), 7.79(2H,d,J=8.9 Hz), 8.03(1H,brs), 8.26(1H,s). IR (KBr) cm$^{-1}$: 3370,3056,1732,1645,1613, 1535,1518,1497,1256,1178,1111,832. Mass (m/z): 455 (M$^+$), 453 (M$^+$).

Example 89

Preparation of 4-n-butoxycarbonylamino-2-(4-chlorocinnamyl)-6-(4-methoxyphenyl)-2H-pyridazin-3-one Using 4-carboxy-2-(4-chlorocinnamyl-6-(4-methoxyphenyl)-2H-pyridazin-3-one as a starting material, the procedures of Example 87 were repeated likewise in n-butanol, whereby the title compound was obtained in a yield of 37.3%.

Pale yellow needles (chloroform-hexane)

Melting point: 150.2–150.9° C. $^1$H-NMR (CDCl$_3$) δ: 0.96(3H,t,J=7.4 Hz), 1.35–1.50(2H,m), 1.63–1.75(2H,m), 3.86(3H,s), 4.23(2H,t,J=6.6 Hz), 4.99(2H,dd,J=1.2,6.4 Hz), 6.40(1H,td,J=6.4,15.8 Hz), 6.64(1H,td,J=1.2,15.8 Hz), 6.96 (2H,d,J=8.9 Hz), 7.27(2H,d,J=8.9 Hz), 7.30(2H,d,J=8.9 Hz), 7.78(2H,d,J=8.9 Hz), 8.08(1H,brs), 8.26(1H,s). IR (KBr) cm$^{-1}$: 3223,3031,1728,1641,1606,1541,1516,1491,1247, 1220,1181. Mass (m/z): 469 (M$^+$), 467 (M$^+$).

Example 90

Preparation of 4-benzyloxycarbonylamino-2-(4-chlorocinnamyl)-6-(4-methoxyphenyl)-2H-pyridazin-3-one Using 4-carboxy-2-(4-chlorocinnamyl-6-(4-methoxyphenyl)-2H-pyridazin-3-one as a starting material, the procedures of Example 87 were repeated likewise in benzyl alcohol, whereby the title compound was obtained in a yield of 12.1%.

Pale yellow fine needles (chloroform-hexane)

Melting point: 190.5–191.7° C. $^1$H-NMR (CDCl$_3$) δ: 3.85(3H,s), 4.98(2H,dd,J=1.0,6.4 Hz), 5.25(2H,s), 6.39(1H, td,J=6.4,15.9 Hz), 6.63(1H,td,J=1.0,15.9 Hz), 6.96(2H,d,J= 9.0 Hz), 7.29(2H,d,J=8.8 Hz), 7.30(2H,d,J=8.8 Hz), 7.32–7.44(5H,m), 7.77(2H,d,J=9.0 Hz), 8.17(1H,brs), 8.26 (1H,s). IR (KBr) cm$^{-1}$: 3231,3034,1729,1640,1607,1540, 1516,1252,1223,1210. Mass (m/z): 503 (M$^+$), 501 (M$^+$).

Example 91

Preparation of 2-(4-chlorocinnamyl)-6-(4-methoxyphenyl)-4-[4-(methylthio)benzyloxycarbonylamino]-2H-pyridazin-3-one Using 4-carboxy-2-(4-chlorocinnamyl)-6-(4-methoxyphenyl)-2H-pyridazin-3-one as a starting material, the procedures of Example 87 were repeated likewise in 4-(methylthio)benzyl alcohol, whereby the title compound was obtained in a yield of 46.0%.
Slightly yellow fine needles (chloroform-hexane)
Melting point: 187.6–188.7° C. $^1$H-NMR (CDCl3) δ: 2.49(3H,s), 3.85(3H,s), 4.98(2H,dd,J=1.2,6.4 Hz), 5.20(2H, s), 6.39(1H,td,J=6.4,15.9 Hz), 6.42(1H,td,J=1.2,15.9 Hz), 6.96(2H,d,J=8.9 Hz), 7.23–7.36(8H,m), 7.77(2H,d,J=8.9 Hz), 8.15(1H,brs), 8.24(1H,s). IR (KBr) cm$^{-1}$: 3224,3028, 1729,1640,1605,1541,1518,1501,1491,1252,1176. Mass (m/z): 549 (M$^+$), 547 (M$^+$).

Example 92

Preparation of 4-carboxy-6-(4-methoxyphenyl)-2-(3-methyl-2-butenyl)-2H-pyridazin-3-one Using 6-(4-methoxyphenyl)-4-ethoxycarbonyl-2-(3-methyl-2-butenyl)-2H-pyridazin-3-one as a starting material, the procedures of Example 86 were repeated likewise, whereby the title compound was obtained in a yield of 93.1%.
Pale yellow needles (chloroform-hexane)
Melting point: 153.5–156.6° C. $^1$H-NMR (CDCl$_3$) δ: 1.78(3H,s), 1.88(3H,s), 3.87(3H,s), 4.94(2H,d,J=6.8 Hz), 5.38–5.54(1H,m), 7.01(2H,d,J=8.8 Hz), 7.80(2H,d,J=8.8 Hz), 8.62(1H,s), 14.27(1H,br). IR (KBr) cm$^{-1}$: 1740,1653, 1629,1609,1517,1477,1420,1252,900. Mass (m/z): 314 (M$^+$).

Example 93

Preparation of 4-ethoxycarbonylamino-6-(4-methoxyphenyl)-2-(3-methyl-2-butenyl)-2H-pyridazin-3-one Using 4-carboxy-6-(4-methoxyphenyl)-2-(3-methyl-2-butenyl)-2H-pyridazin-3-one as a starting material, the procedures of Example 87 were repeated likewise, whereby the title compound was obtained in a yield of 25.9%.
Pale yellow needles (chloroform-hexane)
Melting point: 130.2–131.2° C. $^1$H-NMR (CDCl$_3$) δ: 1.33(3H,t,J=7.1 Hz), 1.75(3H,s), 1.87(3H,s), 3.86(3H,s), 4.27(2H,q,J=7.1 Hz), 4.84(2H,d,J=7.1 Hz), 5.41–5.50(1H, m), 6.96(2H,d,J=8.8 Hz), 7.78(2H,d,J=8.8 Hz), 8.09(1H,br), 8.23(1H,s). IR (KBr) cm$^{-1}$: 3216,1722,1644,1605,1539, 1518,1255,1225,1176,1027,832. Mass (m/z): 357 (M$^+$).

Example 94

Preparation of 4-carboxy-2-cyclopropylmethyl-6-(4-methoxyphenyl)-2H-pyridazin-3-one Using 2-cyclopropylmethyl-4-ethoxycarbonyl-6-(4-methoxyphenyl)-2H-pyridazin-3-one as a starting material, the procedures of Example 86 were repeated likewise, whereby the title compound was obtained in a yield of 99.7%.
Yellow crystals
Melting point: 153.9–154.7° C. $^1$H-NMR (CDCl$_3$) δ: 0.50–0.66(4H,m), 1.41–1.51(1H,m), 3.88(3H,s), 4.23(2H,d, J=7.3 Hz), 7.02(2H,d,J=8.9 Hz), 7.81(2H,d,J=8.9 Hz), 8.64 (1H,s), 14.31(1H,br). IR (KBr) cm$^{-1}$: 1743,1630,1608,1558, 1515,1482,1461,1418.

Example 95

Preparation of 2-cyclopropylmethyl-4-ethoxycarbonylamino-6-(4-methoxyphenyl)-2H-pyridazin-3-one Using 4-carboxy-2-cyclopropylmethyl-6-(4-methoxyphenyl)-2H-pyridazin-3-one as a starting material, the procedures of Example 87 were repeated likewise, whereby the title compound was obtained in a yield of 44.2%.
Colorless needles (chloroform-hexane)
Melting point: 119.1–119.6° C. $^1$H-NMR (CDCl$_3$) δ: 0.45–0.60(4H,m), 1.32–1.45(4H,m), 3.86(3H,s), 4.11(2H,d, J=7.3 Hz), 4.28(2H,q,J=7.1 Hz), 6.96(2H,d,J=8.9 Hz), 7.79 (2H,d,J=8.9 Hz), 8.10(1H,br), 8.25(1H,s). IR (KBr) cm$^{-1}$: 3320,1722,1636,1606,1541,1515,1250,1178,1031,1021, 887,836. Mass (m/z): 343 (M$^+$).

Example 96

Preparation of 2-benzyl-4-carboxy-6-(4-methoxyphenyl)-2H-pyridazin-3-one

Using 2-benzyl-4-ethoxycarbonyl-6-(4-methoxyphenyl)-2H-pyridazin-3-one as a starting material, the procedures of Example 86 were repeated likewise, whereby the title compound was obtained in a yield of 94.8%.
Yellow crystals
$^1$H-NMR (CDCl3) δ: 3.88(3H,s), 5.50(2H,s), 7.01(2H,d, J=8.8 Hz), 7.30–7.55(5H,m), 7.81(2H,d,J=8.8 Hz), 8.62(1H, s), 14.14(1H,br). IR (KBr) cm$^{-1}$: 1750,1633,1607,1516, 1472,1457,1419,1250,1026,898,838. Mass (m/z): 336 (M$^+$).

Example 97

Preparation of 2-benzyl-4-ethoxycarbonylamino-6-(4-methoxyphenyl)-2H-pyridazin-3-one Using 2-benzyl-4-carboxy-6-(4-methoxyphenyl)-2H-pyridazin-3-one as a starting material, the procedures of Example 87 were repeated likewise, whereby the title compound was obtained in a yield of 11.2%.
Pale yellow needles (chloroform-diethyl ether)
Melting point: 152.1–162.5° C. $^1$H-NMR (CDCl3) δ: 1.33(3H,t,J=7.1 Hz), 3.86(3H,s), 4.25(2H,q,J=7.1 Hz), 5.40 (2H,s), 6.96(2H,d,J=8.9 Hz), 7.27–7.38(3H,m), 7.45–7.50 (2H,m), 7.78(2H,d,J=8.9 Hz), 8.07(1H,brs), 8.24(1H,s). IR (KBr) cm$^{-1}$: 3225,1728,1641,1606,1540,1516,1256,1226, 1180,1171,829. Mass (m/z): 379 (M$^+$).

Example 98

Preparation of 4-carboxy-6-(4-methoxyphenyl)-2-(3-phenylpropyl)-2H-pyridazin-3-one Using 4-methoxycarbonyl-6-(4-methoxyphenyl)-2-(3-phenylpropyl)-2H-pyridazin-3-one as a starting material, the procedures of Example 86 were repeated likewise, whereby the title compound was obtained in a yield of 85.8%.
Pale yellow needles (chloroform-hexane)
Melting point: 121.0–122.1° C. $^1$H-NMR (CDCl$_3$) δ: 2.23–2.36(2H,m), 2.77(2H,t,J=7.3 Hz), 3.88(3H,s), 4.41 (2H,t,J=7.3 Hz), 7.01(2H,d,J=8.8 Hz), 7.14–7.30(5H,m), 7.79(2H,d,J=8.8 Hz), 8.57(1H,s), 14.21(1H,br). IR (KBr) cm$^{-1}$: 1740,1632,1609,1515,1474,1451,1417,1249,1187, 837.

Example 99

Preparation of 4-ethoxycarbonylamino-6-(4-methoxyphenyl)-2-(3-phenylpropyl)-2H-pyridazin-3-one Using 4-carboxy-6-(4-methoxyphenyl)-2-(3-phenylpropyl)-2H-pyridazin-3-one as a starting material, the procedures of Example 87 were repeated likewise, whereby the title compound was obtained in a yield of 41.1%.
Colorless needles (chloroform-diethyl ether-hexane)
Melting point: 100.9–101.3° C. $^1$H-NMR (CDCl$_3$) δ: 1.35(3H,t,J=7.76 Hz), 2.16–2.28(2H,m), 2.73(2H,t,J=7.7 Hz), 3.86(3H,s), 4.28(2H,q,J=7.1 Hz), 4.30(2H,t,J=7.6 Hz), 6.96(2H,d,J=9.0 Hz), 7.14–7.31(5H,m), 7.77(2H,d,J=9.0 Hz), 8.08(1H,brs), 8.22(1H,s). IR (KBr) cm$^{-1}$: 3223,1725, 1641,1608,1547,1517,1225,1200,1175.

Example 100

Preparation of 4-benzyloxycarbonylamino-6-(4-methoxyphenyl)-2-(3-phenylpropyl)-2H-pyridazin-3-one Using 4-carboxy-6-(4-methoxyphenyl)-2-(3-phenylpropyl)-2H-pyridazin-3-one as a starting material, the procedures of Example 90 were repeated likewise, whereby the title compound was obtained in a yield of 52.8%.
Colorless needles (chloroform-hexane)
Melting point: 117.6–118.1° C. (dec.) $^1$H-NMR (CDCl$_3$) δ: 2.15–2.27(2H,m), 2.72(2H,t,J=7.1 Hz), 3.86(3H,s), 4.29 (2H,t,J=7.1 Hz), 5.23(2H,s), 6.36(2H,d,J=8.9 Hz), 7.13–7.30(5H,m), 7.32–7.44(5H,m), 7.76(2H,d,J=8.9 Hz), 8.16(1H,brs), 8.22(1H,s). IR (KBr) cm$^{-1}$: 3221,1733,1640, 1604,1539,1516,1500,1252,1220,1175.

Example 101

Preparation of 4-carboxy-2-(4-chlorocinnamyl)-6-(3,4-dimethoxyphenyl)-2H-pyridazin-3-one Using 2-(4-chlorocinnamyl)-6-(3,4-dimethoxyphenyl)-4-methoxycarbonyl-2H-pyridazin-3-one as a starting material, the procedures of Example 86 were repeated likewise, whereby the title compound was obtained in a yield of 99.1%.
Yellow fine needles (chloroform-hexane)
Melting point: 229.5–230.9° C. (dec.) $^1$H-NMR (CDCl$_3$) δ: 3.95(6H,s), 5.11(2H,dd,J=1.0,6.8 Hz), 6.40(1H,td,J=6.8, 16.1 Hz), 6.75(1H,td,J=1.0,16.1 Hz), 6.97(1H,d,J=8.8 Hz), 7.33(2H,d,J=8.8 Hz), 7.39–7.45(2H,m), 8.67(1H,s), 14.09 (1H,brs). IR (KBr) cm$^{-1}$: 1753,1635,1570,1520,1471,1460, 1238. Mass (m/z): 428 (M$^+$), 426 (M$^+$).

Example 102

Preparation of 2-(4-chlorocinnamyl)-6-(3,4-dimethoxyphenyl)-4-ethoxycarbonylamino-2H-pyridazin-3-one Using 4-carboxy-2-(4-chlorocinnamyl)-6-(3,4-dimethoxyphenyl)-2H-pyridazin-3-one as a starting material, the procedures of Example 87 were repeated likewise, whereby the title compound was obtained in a yield of 43.6%.
Slightly yellow needles (chloroform-hexane)
Melting point: 183.8–184.8° C. $^1$H-NMR (CDCl$_3$) δ: 1.35(3H,t,J=7.3 Hz), 3.93(3H,s), 3.94(3H,s), 4.29(2H,q,J= 7.3 Hz), 5.01(2H,dd,J=1.0,6.6 Hz), 6.41(1H,td,J=6.3,15.8 Hz), 6.65(1H,dt,J=15.8,1.0 Hz), 6.92(1H,d,J=8.2 Hz), 7.26 (2H,d,J=8.6 Hz), 7.31(2H,d,J=8.6 Hz), 7.37(1H,dd,J=2.2, 8.2 Hz), 7.42(1H,d,J=2.0 Hz), 8.09(1H,br), 8.27(1H,s). IR (KBr) cm$^{-1}$: 3232,3023,1725,1636,1607,1544,1519,1491, 1423,1262,1223,1151,1022. Mass (m/z): 471 (M$^+$), 469 (M$^+$).

Example 103

Preparation of 4-carboxy-2-(4-chlorocinnamyl)-6-(3-fluoro-4-methoxyphenyl)-2H-pyridazin-3-one Using 2-(4-chlorocinnamyl)-6-(3-fluoro-4-methoxyphenyl)-4-methoxycarbonyl-2H-pyridazin-3-one as a starting material, the procedures of Example 86 were repeated likewise, whereby the title compound was obtained in a yield of 96.5%.
Pale yellow fine needles (chloroform-hexane)
Melting point: 215.8–219.2° C. $^1$H-NMR (CDCl$_3$) δ: 3.97(3H,s), 5.10(2H,dd,J=1.5,6.8 Hz), 6.39(1H,td,J=6.8, 16.1 Hz), 6.75(1H,td,J=1.5,16.1 Hz), 7.03–7.10(1H,m), 7.30 (2H,d,J=9.0 Hz), 7.33(2H,d,J=9.0 Hz), 7.54–7.59(1H,m), 7.66–7.72(1H,m), 8.61(1H,s), 13.99(1H,br). IR (KBr) cm$^{-1}$: 1745,1628,1523,1481,1437,1271. Mass (m/z): 416 (M$^+$), 414 (M$^+$).

Example 104

Preparation of 2-(4-chlorocinnamyl)-4-ethoxycarbonylamino-6-(3-fluoro-4-methoxyphenyl)-2H-pyridazin-3-one Using 4-carboxy-2-(4-chlorocinnamyl)-6-(3-fluoro-4-methoxyphenyl)-2H-pyridazin-3-one as a starting material, the procedures of Example 87 were repeated likewise, whereby the title compound was obtained in a yield of 29.4%.
Slightly yellow fine needles (chloroform-hexane)
Melting point: 186.7–187.5° C. $^1$H-NMR (CDCl$_3$) δ: 1.35(3H,t,J=7.1 Hz), 3.94(3H,s), 4.29(2H,q,J=7.1 Hz), 4.99 (2H,dd,J=1.2,6.6 Hz), 6.39(1H,td,J=6.6,16.1 Hz), 6.65(1H, td,J=1.2,16.1 Hz), 6.97–7.04(1H,m), 7.27(2H,d,J=8.8 Hz), 7.30(2H,d,J=8.8 Hz), 7.51–7.56(1H,m), 7.62–7.68(1H,m), 8.08(1H,brs), 8.24(1H,s). IR (KBr) cm$^{-1}$: 3217,1728,1644, 1610,1544,1520. Mass (m/z): 459 (M$^+$), 457 (M$^+$).

Example 105

Preparation of 4-carboxy-2-(4-chlorocinnamyl)-6-(3-chloro-4-methoxyphenyl)-2H-pyridazin-3-one Using 2-(4-chlorocinnamyl)-6-(3-chloro-4-methoxyphenyl)-4-methoxycarbonyl-2H-pyridazin-3-one as a starting material, the procedures of Example 86 were repeated likewise, whereby the title compound was obtained in a yield of 95.1%.
Pale yellow crystalline powder (chloroform-hexane)
$^1$H-NMR (CDCl$_3$) δ: 3.98(3H,s), 5.11(2H,dd,J=1.0,6.8 Hz), 6.39(1H,td,J=6.8,15.6 Hz), 6.76(1H,td,J=1.0,15.6 Hz), 7.03 (1H,d,J=8.6 Hz), 7.30(2H,d,J=8.8 Hz), 7.33(2H,d,J=8.8 Hz), 7.71(1H,dd,J=2.1,8.6 Hz), 7.96(1H,d,J=2.1 Hz), 8.63(1H,s), 13.99(1H,br). IR (KBr) cm$^{-1}$: 1748,1628,1508,1481,1407, 1292,1260. Mass (m/z): 432 (M$^+$), 430 (M$^+$).

Example 106

Preparation of 2-(4-chlorocinnamyl)-6-(3-chloro-4-methoxyphenyl)-4-ethoxycarbonylamino-2H-pyridazin-3-one Using 4-carboxy-2-(4-chlorocinnamyl)-6-(3-chloro-4-methoxyphenyl)-2H-pyridazin-3-one as a starting material, the procedures of Example 87 were repeated likewise, whereby the title compound was obtained in a yield of 44.9%.
Colorless fine needles (chloroform-hexane)
Melting point: 183.0–183.8° C. $^1$H-NMR (CDCl$_3$) δ: 1.35(3H,t,J=7.1 Hz),3.95(3H,s), 4.29(2H,q,J=7.1 Hz), 4.99 (2H,dd,J=1.0,6.6 Hz), 6.40(1H,td,J=6.6,15.8 Hz), 6.66(1H, dt,J=15.8,1.0 Hz), 6.97(1H,d,J=8.6 Hz), 7.27(2H,d,J=8.7 Hz), 7.31(2H,d,J=8.7 Hz), 7.69(1H,dd,J=2.3,8.6 Hz), 7.91 (1H,d,J=2.3 Hz), 8.09(1H,brs),8.24(1H,s). IR (KBr) cm$^{-1}$: 3235,1724,1641,1606,1540,1508,1264,1229. Mass (m/z): 475 (M$^+$), 473 (M$^+$).

Example 107

Preparation of 4-carboxy-2-(4-chlorocinnamyl)-6-[4-(methylthio)phenyl]-2H-pyridazin-3-one Using 2-(4-chlorocinnamyl)-4-methoxycarbonyl-6-[4-(methylthio)phenyl]-2H-pyridazin-3-one as a starting material, the procedures of Example 86 were repeated likewise, whereby the title compound was obtained in a yield of 77.1%.
Yellow prisms (chloroform-hexane)
Melting point: 176.0–177.6° C. (dec.) $^1$H-NMR (CDCl$_3$) δ: 2.54(3H,s), 5.11(2H,d,J=6.8 Hz), 6.39(1H,td,J=6.8,15.9 Hz), 6.74(1H,d,J=15.9 Hz), 7.25–7.37(6H,m), 7.78(2H,d,J=8.8 Hz), 8.66(1H,s), 14.01(1H,br). IR (KBr) cm$^{-1}$: 1749, 1655,1630,1594,1567,1492,1474,1403. Mass (m/z): 414 (M$^+$), 412 (M$^+$).

Example 108

Preparation of 2-(4-chlorocinnamyl)-4-ethoxycarbonylamino-6-[4-(methylthio)phenyl]-2H-pyridazin-3-one Using 4-carboxy-2-(4-chlorocinnamyl)-6-[4-(methylthio)phenyl]-2H-pyridazin-3-one as a starting material, the procedures of Example 87 were repeated likewise, whereby the title compound was obtained in a yield of 13.6%.
Pale yellow fine needles (chloroform-hexane)
Melting point: 158.3–162.1° C. $^1$H-NMR (CDCl$_3$) δ: 1.35(3H,t,J=7.1 Hz), 2.52(3H,s), 4.29(2H,q,J=7.1 Hz), 5.00 (2H,dd,J=1.1,6.5 Hz), 6.40(1H,td,J=6.5,15.9 Hz), 6.65(1H, td,J=1.1,15.9 Hz), 7.27(2H,d,J=8.8 Hz), 7.30(2H,d,J=8.7 Hz), 7.30(2H,d,J=8.8 Hz), 7.76(2H,d,J=8.7 Hz), 8.13(1H, br), 8.27(1H,s). IR (KBr) cm$^{-1}$: 3220,1728,1641,1606,1538, 1501,1491. Mass (m/z): 457 (M$^+$), 455 (M$^+$).

Example 109

Preparation of 4-carboxy-2-(2,4-difluorocinnamyl)-6-(4-methoxyphenyl)-2H-pyridazin-3-one Using 2-(2,4-difluorocinnamyl)-4-methoxycarbonyl-6-(4-methoxyphenyl)-2H-pyridazin-3-one as a starting material, the procedures of Example 86 were repeated likewise, whereby the title compound was obtained in a yield of 93.1%.
Slightly yellow fine needles (chloroform-hexane)
Melting point: 200.3–201.3° C. $^1$H-NMR (CDCl$_3$) δ: 3.88(3H,s), 5.11(2H,dd,J=1.2,6.8 Hz), 6.45(1H,td,J=6.8, 16.1 Hz), 6.73–6.92(3H,m), 7.01(2H,d,J=8.8 Hz), 7.37–7.48 (1H,m), 7.82(2H,d,J=8.8 Hz), 8.66(1H,s), 14.09(1H,brs). IR (KBr) cm$^{-1}$: 3065,1741,1632,1608,1504,1474,1419,1252, 967. Mass (m/z): 398 (M$^+$).

Example 110

Preparation of 2-(2,4-difluorocinnamyl)-4-ethoxycarbonylamino-6-(4-methoxyphenyl)-2H-pyridazin-3-one Using 4-carboxy-2-(2,4-difluorocinnamyl)-6-(4-methoxyphenyl)-2H-pyridazin-3-one as a starting material, the procedures of Example 87 were repeated likewise, whereby the title compound was obtained in a yield of 30.0%.
Pale yellow needles (chloroform-hexane)
Melting point: 128.3–128.9° C. $^1$H-NMR (CDCl$_3$) δ: 3.15(3H,t,J=7.1 Hz), 3.86(3H,s), 4.28(2H,q,J=7.1 Hz), 5.01 (2H,dd,J=1.2,6.6 Hz), 6.44(1H,td,J=6.6,16.1 Hz), 6.73–6.86 (3H,m), 6.96(2H,d,J=8.8 Hz), 7.36–7.46(1H,m), 7.79(2H,d, J=8.8 Hz), 8.08(1H,brs), 8.26(1H,s). IR (KBr) cm$^{-1}$: 3221, 3073,1728,1641,1605,1541,1519,1502,1256,1224,1176. Mass (m/z): 398(M$^+$).

Example 111

Preparation of 4-amino-2-(4-chlorocinnamyl)-6-(4-methoxyphenyl)-2H-pyridazin-3-one To a suspension of 2-(4-chlorocinnamyl)-4-ethoxycarbonylamino-(4-methoxyphenyl)-2H-pyridazin-3-one (335 mg, 0.76 mmol) in methanol (40 ml), a 4N aqueous solution of sodium hydroxide (20 ml) was added, followed by stirring at 70° C. for 30 minutes. The methanol was distilled off. Water (100 ml) was added to the residue, followed by extraction with chloroform. The organic layer was washed with brine and then dried over anhydrous sodium sulfate. The solvent was distilled off, and the residue was separated and purified by chromatography on a silica gel column (silica gel: 10 g, chloroform). Crystallization was conducted from chloroform-hexane, whereby the title compound (266 mg, 95.0%) was obtained as colorless fine needles.
Melting point: 142.7–143.2° C. $^1$H-NMR (CDCl$_3$) δ: 3.84(3H,s), 4.93–5.01(4H,m), 6.43(1H,td,J=6.4,15.9 Hz), 6.64(1H,td,J=1.0,15.9 Hz), 6.69(1H,s), 6.95(2H,d,J=8.9 Hz), 7.25(2H,d,J=8.6 Hz), 7.31(2H,d,J=8.6 Hz), 7.69(2H,d, J=8.9 Hz). IR (KBr) cm$^{-1}$: 3435,3325,3038,1646,1612, 1597,1521,1491,1252,1238,833. Mass (m/z): 369 (M$^+$), 367 (M$^+$).

Example 112

Preparation of 2-(4-chlorocinnamyl)-4-formylamino-6-(4-methoxyphenyl)-2H-pyridazin-3-one To a solution of 4-amino-2-(4-chlorocinnamyl)-6-(4-methoxyphenyl)-2H-pyridazin-3-one (40 mg, 0.11 mmol) in benzene (2 ml), triethylamine (151 mg, 1.49 mmol) and a formic acid-acetic acid (1:1) mixed solution (0.5 ml) were added, followed by stirring at room temperature for 16 hours. The reaction mixture was extracted with chloroform. The extract was washed successively with a saturated solution of sodium hydrogencarbonate and brine, and was then dried over anhydrous sodium sulfate. The solvent was distilled off and the residue was crystallized from chloroform-hexane, whereby the title compound (41 mg, 95.2%) was obtained as colorless needles.
Melting point: 213.0–213.8° C. $^1$H-NMR (CDCl$_3$) δ: 3.86(3H,s), 5.00(2H,dd,J=1.0,6.5 Hz), 6.40(1H,td,J=6.5, 15.9 Hz), 6.66(1H,td,J=1.0,15.9 Hz), 6.97(2H,d,J=9.0 Hz), 7.26(2H,d,J=8.8 Hz), 7.32(2H,d,J=8.8 Hz), 7.79(2H,d,J=9.0 Hz), 8.59(1H,s), 8.64(1H,s), 8.79(1H,br). IR (KBr) cm$^{-1}$: 3277,1702,1634,1601,1549,1518,1491,1418,1245,1138, 1033,812. Mass (m/z): 397 (M$^+$), 395 (M$^+$).

Example 113

Preparation of 4-acetylamino-2-(4-chlorocinnamyl)-6-(4-methoxyphenyl)-2H-pyridazin-3-one Acetic anhydride (0.5 m!) was added to 4-amino-2-(4-chlorocinnamyl)-6-(4-methoxyphenyl)-2H-pyridazin-3-one (40 mg, 0.11 mmol), followed by heating under stirring at 70° C. for 12 hours. A saturated aqueous solution of sodium hydrogencarbonate was added to the reaction mixture. Subsequent to stirring at room temperature for 1 hour, the mixture was extracted with ethyl acetate. The organic layer was washed with brine and then dried over anhydrous sodium sulfate. The solvent was distilled off, and the residue was separated and purified by silica gel preparative chromatography [developer: hexane/ethyl acetate (1/1)]. Crystallization was conducted from chloroform-hexane, whereby the title compound (31 mg, 70.0%) was obtained as slightly brown needles.

Melting point: 158.7–161.9° C. $^1$H-NMR (CDCl$_3$) δ: 2.27(3H,s), 3.86(3H,s), 5.00(2H,dd,J=1.2,6.4 Hz), 6.39(1H, td,J=6.5,15.9 Hz), 6.65(1H,td,J=1.2,15.9 Hz), 6.97(2H,d,J=9.0 Hz), 7.27(2H,d,J=8.9 Hz), 7.30(2H,d,J=8.9 Hz), 7.79 (2H,d,J=9.0 Hz), 8.58(1H,s), 8.61(1H,brs). IR (KBr) cm$^{-1}$: 3274,3002,1701,1634,1603,1537,1516,1491,1405,1252, 1180,1070. Mass (m/z): 411 (M$^+$), 409 (M$^+$).

Example 114

Preparation of 2-(4-chlorocinnamyl)-6-(4-methoxyphenyl)-4-propionylamino-2H-pyridazin-3-one 4-Amino-2-(4-chlorocinnamyl)-6-(4-methoxyphenyl)-2H-pyridazin-3-one and propionic anhydride were processed as in Example 113, whereby the title compound was obtained in a yield of 84.6%.
Colorless needles (chloroform-hexane)

Melting point: 147.7–148.6° C. $^1$H-NMR (CDCl$_3$) δ: 1.26(3H,t,J=7.6 Hz), 2.51(2H,q,J=7.6 Hz), 3.86(3H,s), 5.00 (2H,dd,J=1.2,6.4 Hz), 6.40(1H,td,J=6.4,15.9 Hz), 6.65(1H, td,J=1.2,15.9 Hz), 7.27(2H,d,J=8.8 Hz), 7.30(2H,d,J=8.8 Hz), 7.79(2H,d,J=9.0 Hz), 8.61(1H,brs), 8.62(1H,s). IR (KBr) cm$^{-1}$: 3270,3046,1633,1599,1534,1516,1492,1255, 1173,833,772. Mass (m/z): 425 (M$^+$), 423 (M$^+$).

Example 115

Preparation of 4-n-butyrylamino-2-(4-chlorocinnamyl)-6-(4-methoxyphenyl)-2H-pyridazin-3-one 4-Amino-2-(4-chlorocinnamyl)-6-(4-methoxyphenyl)-2H-pyridazin-3-one and butyric anhydride were processed as in Example 113, whereby the title compound was obtained in a yield of 88.2%.
Colorless needles (chloroform-hexane)

Melting point: 152.1–152.7° C. $^1$H-NMR (CDCl$_3$) δ: 1.04(3H,t,J=7.5 Hz), 1.70–1.85(2H,m), 2.45(2H,t,J=7.3 Hz), 3.86(3H,s), 5.00(2H,dd,J=1.2,6.4 Hz), 6.41(1H,td,J=6.4,15.9 Hz), 6.64(1H,td,J=1.2,15.9 Hz), 6.96(2H,d,J=8.9 Hz), 7.27(2H,d,J=8.8 Hz), 7.30(2H,d,J=8.8 Hz), 7.79(2H,d, J=8.9 Hz), 8.60(1H,brs), 8.62(1H,s). IR (KBr) cm$^{-1}$: 3271, 3051,3034,1632,1598,1532,1517,1500,1258,1172. Mass (m/z): 439 (M$^+$), 437 (M$^+$).

Example 116

Preparation of 2-(4-chlorocinnamyl)-6-(4-methoxyphenyl)-4-(N-methylethoxycarbonylamino)-2H-pyridazin-3-one In N,N-dimethylformamide, 2-(4-chlorocinnamyl)-4-ethoxycarbonylamino-6-(4-methoxyphenyl)-2H-pyridazin-3-one (100 mg) was stirred at 80° C. for 1 hour in the presence of methyl iodide and potassium carbonate. The procedures of Example 1 were then repeated likewise, whereby the title compound (92 mg, 89.2%) was obtained.
Slightly yellow fine needles (chloroform-hexane)

Melting point: 130.8–131.5° C. $^1$H-NMR (CDCl$_3$) δ: 1.27(3H,t,J=7.1 Hz), 3.30(3H,s), 3.86(3H,s), 4.22(2H,q,J=7.1 Hz), 5.00(2H,dd,J=1.0,6.3 Hz), 6.42(1H,td,J=6.6,15.9 Hz), 6.67(1H,td,J=1.0,15.9 Hz), 6.97(2H,d,J=9.0 Hz), 7.27 (2H,d,J=8.7 Hz), 7.31(2H,d,J=8.7 Hz), 7.63(1H,s), 7.71(2H, d,J=9.0 Hz). IR (KBr) cm$^{-1}$: 1706,1655,1611,1520,1316, 1307,1252,1176. Mass (m/z): 455 (M$^+$), 453 (M$^+$).

Example 117

Preparation of 2-(4-chlorocinnamyl)-6-(4-methoxyphenyl)-4-methylamino-2H-pyridazin-3-one Using 2-(4-chlorocinnamyl)-6-(4-methoxyphenyl)-4-(N-methylethoxycarbonylamino)-2H-pyridazin-3-one (68 mg) as a starting material, the procedures of Example 111 were repeated likewise (stirred at 70° C. for 1 hour), whereby the title compound (49 mg, 93.9%) was obtained.
Colorless needles (chloroform-hexane)

Melting point: 148.4–149.2° C. $^1$H-NMR (CDCl$_3$) δ: 2.96(3H,d,J=5.1 Hz), 3.85(3H,s), 4.96(2H,dd,J=1.2,6.4 Hz), 5.77(2H,brq,J=5.1 Hz), 6.33(1H,s), 6.42(1H, td,J=6.4,15.9 Hz), 6.62(1H,td,J=1.2,15.9 Hz), 6.96(2H,d,J=9.0 Hz), 7.25 (2H,d,J=8.9 Hz), 7.30(2H,d,J=8.9 Hz), 7.74(2H,d,J=9.0 Hz). IR (KBr) cm$^{-1}$: 3318,1630,1606,1519,1432,1240. Mass (m/z): 383 (M$^+$), 381 (M$^+$).

Example 118

Preparation of 2-(4-chlorocinnamyl)-6-(4-methoxyphenyl)-4-[N-(3-phenylpropyl) ethoxycarbonylamino]-2H-pyridazin-3-one Using 2-(4-chlorocinnamyl)-4-ethoxycarbonylamino-6-(4-methoxyphenyl)-2H-pyridazin-3-one (70 mg) and 3-phenylpropyl bromide as starting materials, the procedures of Example 116 were repeated likewise, whereby the title compound (61 mg, 68.7%) was obtained.
Colorless fine needles (chloroform-diethyl ether-hexane)

Melting point: 113.5–114.2° C. $^1$H-NMR (CDCl$_3$) δ: 1.22(3H,t,J=7.1 Hz), 1.85–1.98(2H,m), 2.65(2H,t,J=7.7 Hz), 3.79(2H,t,J=7.4 Hz), 3.86(3H,s), 4.19(2H,q,J=7.1 Hz), 4.99(2H,dd,J=1.0,6.3 Hz), 6.42(1H,td,J=6.6,15.9 Hz), 6.65 (1H,td,J=1.0,15.9 Hz), 6.97(2H,d,J=8.8 Hz), 7.27(2H,d,J=8.9 Hz), 7.10–7.33(9H,m), 7.48(1H,s), 7.68(2H,d,J=8.8 Hz). IR (KBr) cm$^{-1}$: 1678,1657,1616,1522,1305,1252,1183, 1166. Mass (m/z): 559 (M$^+$), 557 (M$^+$).

Example 119

Preparation of 2-(4-chlorocinnamyl)-6-(4-methoxyphenyl)-4-(3-phenylpropyl)amino)-2H-pyridazin-3-one Using 2-(4-chlorocinnamyl)-6-(4-methoxyphenyl)-4-[N-(3-phenylpropyl)ethoxycarbonylamino]-2H-pyridazin-3-one (31 mg) as a starting material, the procedures of Example 111 were repeated likewise, whereby the title compound (26 mg, 96.3%) was obtained.
Colorless fine needles (chloroform-hexane)

Melting point: 161.2–162.6° C. $^1$H-NMR (CDCl$_3$) δ: 1.96–2.09(2H, m), 2.76(2H,t,J=7.4 Hz), 3.17–3.26(2H,m), 3.85(3H,s), 4.96(2H,dd,J=1.2,6.4 Hz), 5.79(1H,brt,J=5.5 Hz), 6.25(1H,s), 6.43(1H,td,J=6.4,15.9 Hz), 6.63(1H,td,J=1.2,15.9 Hz), 6.95(2H,d,J=8.9 Hz), 7.17–7.34(9H,m), 7.68 (2H,d,J=8.9 Hz). IR (KBr) cm $^{-1}$: 3315,1630,1602,1519, 1258,1177,821. Mass (m/z): 487 (M$^+$), 485 (M$^+$).

Example 120

Preparation of 2-(4-chlorocinnamyl)-6-(4-methoxyphenyl)-4-[N-(2-pyridylmethyl)ethoxycarbonylamino]-2H-pyridazin-3-one 2-(4-Chlorocinnamyl)-4-ethoxycarbonylamino-6-(4-methoxyphenyl)-2H-pyridazin-3-one (70 mg) and 2-pyridylmethyl bromide were processed as in Example 116 (stirred at 70° C. for 4 hours), whereby the title compound (82 mg, 97.0%) was obtained.
Pale brown oil $^1$H-NMR (CDCl$_3$) δ: 1.18(3H,t,J=7.1 Hz), 3.85(3H,s), 4.20(2H,q,J=7.1 Hz), 4.98(2H,dd,J=1.0,6.3 Hz), 5.05(2H,s), 6.40(1H,td,J=6.6,15.9 Hz), 6.63(1H,td,J=1.0,15.9 Hz), 6.95 (2H,d,J=8.8 Hz), 7.11–7.17(1H,m), 7.27(2H,d,J=9.0 Hz), 7.29(2H,d,J=9.0 Hz), 7.40–7.45(1H,m), 7.59–7.64(1H,m), 7.67(2H,d,J=8.8 Hz), 7.78(1H,s), 8.49–8.53(1H,m). IR (film) cm$^{-1}$: 1716,1660,1652,1610,1519,1305,1252,1209, 1169. Mass (m/z): 532 (M$^+$), 530 (M$^+$).

In a manner known per se in the art, the monochloride of the title compound was obtained in a yield of 74.2%.
Pale brown amorphous Melting point: 90° C. (softened) $^1$H-NMR (CDCl3) δ: 1.16(3H,t,J=7.1 Hz), 3.85(3H,s), 4.17(2H,q,J=7.1 Hz), 5.05 (2H,dd,J=1.0,6.4 Hz), 5.09(2H,s), 6.48(1H,td,J=6.4,15.9 Hz), 6.69(1H,td,J=1.0,15.9 Hz), 7.03(2H,d,J=8.8 Hz), 7.30 (2H,d,J=8.5 Hz), 7.40(2H,d,J=8.5 Hz), 7.72–7.79(1H,m), 7.83(2H,d,J=8.8 Hz), 7.97–8.03(1H,m), 8.16(1H,s), 8.27–8.36(1H,m), 8.69–8.74(1H,m). IR (KBr) cm$^{-1}$: 1717, 1652,1570,1519,1305,1251,1225,1169.

Example 121

Preparation of 4-amino-2-benzyl-6-(4-methoxyphenyl)-2H-pyridazin-3-one

Using 2-benzyl-4-ethoxycarbonylamino-6-(4-methoxyphenyl)-2H-pyridazin-3-one as a starting material, the procedures of Example 111 were repeated likewise, whereby the title compound was obtained in a yield of 57.4%.
Slightly brown prisms (chloroform-hexane)

Melting point: 115.1–115.6° C. $^1$H-NMR (CDCl$_3$) δ: 3.85(3H,s), 4.94(2H,br), 5.39(2H,s), 6.95(2H,d,J=8.8 Hz), 7.24–7.37(3H,m), 7.47–7.52(2H,m), 7.69(2H,d,J=8.8 Hz). IR (KBr) cm$^{-1}$: 3419,3322,3286,3259,1644,1600,1519, 1251,1184,1021,839. Mass (m/z): 307 (M$^+$).

Example 122

Preparation of 2-benzyl-4-methanesulfonylamino-6-(4-methoxyphenyl)-2H-pyridazin-3-one (1) Preparation of 2-benzyl-4-dimethanesulfonylamino-6-(4-methoxyphenyl)-2H-pyridazin-3-one To a solution of 4-amino-2-benzyl-6-(4-methoxyphenyl)-2H-pyridazin-3-one (60 mg, 0.20 mmol) and triethylamine (80 mg, 0.79 mmol) in toluene (1 ml), methanesulfonyl chloride (70 mg, 0.61 mmol) was added, followed by heating under stirring at 40° C. for 1 hour. Chloroform was added to the reaction mixture. The organic layer was washed with water and brine, and was then dried over anhydrous sodium sulfate. The solvent was distilled off under reduced pressure and the residue was separated and purified by silica gel preparative chromatography [developer: hexane/ethyl acetate (1/1)], whereby the title compound (76 mg, 90.4%) was obtained.

$^1$H-NMR (CDCl$_3$) δ: 3.55(6H,s), 3.86(3H,s), 5.43(2H,s), 6.70(2H,d,J=9.2 Hz), 7.27–7.37(3H,m), 7.42–7.46(2H,m), 7.65–7.70(3H,m).

(2) Preparation of 2-benzyl-4-methanesulfonylamino-6-(4-methoxyphenyl)-2H-pyridazin-3-one To a solution of 2-benzyl-4-dimethanesulfonylamino-6-(4-methoxyphenyl)-2H-pyridazin-3-one (36 mg, 0.08 mmol) in methanol (1 ml), a 4N aqueous solution of sodium hydroxide (1 ml) was added, followed by stirring at room temperature for 2 hours. The reaction mixture was acidified with hydrochloric acid under ice cooling, added with water (30 ml), and then extracted with chloroform (20 ml×2). The organic layer was washed with brine and then dried over anhydrous sodium sulfate. The solvent was distilled off and the residue (31 mg) was crystallized from chloroform-hexane, whereby the title compound (26 mg, 86.9%) was obtained as slightly brown needles.

Melting point: 195.0–195.5° C. $^1$H-NMR (CDCl$_3$) δ: 3.13(3H,s), 3.86(3H,s), 5.40(2H,s), 6.98(2H,d,J=8.8 Hz), 7.30–7.39(3H,m), 7.47–7.51(2H,m), 7.75(2H,d,J=8.8 Hz), 8.02(1H,br). IR (KBr) cm$^{-1}$: 3151,1634,1599,1440,1250, 1154,1021,835,770,753,700. Mass (m/z): 385 (M$^+$).

Example 123

Preparation of 2-benzyl-4-(3-isopropylureido)-6-(4-methoxyphenyl)-2H-pyridazin-3-one To a solution of 4-amino-2-benzyl-6-(4-methoxyphenyl)-2H-pyridazin-3-one (50 mg, 0.16 mmol) in benzene (2 ml), isopropyl isocyanate (0.1 ml, 1.02 mmol) was added, followed by stirring at 60° C. for 17 hours. The solvent was distilled off, and the residue was separated and purified by silica gel preparative chromatography [developer: chloroform/methanol (15/1)]. The crude crystals (63 mg) were recrystallized from chloroform-hexane, whereby the title compound (56 mg, 87.7%) was obtained as colorless needles.

Melting point: 200.2–201.0° C. $^1$H-NMR (CDCl$_3$) δ: 1.15(3H,s), 1.18(3H,s), 3.85(3H,s), 3.92–4.07(1H,m), 5.38–5.52(3H,m), 6.93(2H,d,J=8.9 Hz), 7.25–7.45(5H,m), 7.79(2H,d,J=8.9 Hz), 8.31(1H,brs), 8.47(1H,s). IR (KBr) cm$^{-1}$: 3370,3283,1698,1624,1592,1517,1255,1175,1032, 830,701. Mass (m/z): 392 (M$^+$).

Example 124

Preparation of 4-amino-2-cyclopropylmethyl-6-(4-methoxyphenyl)-2H-pyridazin-3-one Using 2-cyclopropylmethyl-4-ethoxycarbonylamino-6-(4-methoxyphenyl)-2H-pyridazin-3-one as a starting material, the procedures of Example 111 were repeated likewise (stirred at 60° C. for 40 minutes), whereby the title compound (82 mg, 97.0%) was obtained.
Colorless needles (chloroform-hexane)

Melting point: 110.8–111.3° C. $^1$H-NMR (CDCl$_3$) δ: 0.44–0.59(4H,m), 1.35–1.52(1H,m), 3.85(3H,s), 4.09(2H,d, J=7.3 Hz), 4.95(2H,br), 6.68(1H,s), 6.95(2H,d,J=8.9 Hz), 7.70(2H,d,J=8.9 Hz). IR (KBr) cm$^{-1}$: 3455,3300,3261,3206, 1641,1601,1575,1520,1420,1246,1239,1025,835. Mass (m/z): 271 (M$^+$).

Example 125

Preparation of 2-cyclopropylmethyl-4-(3-isopropylureido)-6-(4-methoxyphenyl)-2H-pyridazin-3-one Using 4-amino-2-cyclopropylmethyl-6-(4-methoxyphenyl)-2H-pyridazin-3-one as a starting material, the procedures of Example 123 were repeated likewise, whereby the title compound was obtained in a yield of 77.0%.
Colorless needles (chloroform-hexane)

Melting point: 195.8–197.0° C. $^1$H-NMR (CDCl$_3$) δ: 0.45–0.62(4H,m), 1.24(3H,s), 1.27(3H,s), 1.34–1.51(1H,m), 3.85(3H,s), 4.00–4.15(3H,m), 5.85(1H,brd,J=7.9 Hz), 6.95 (2H,d,J=8.9 Hz), 7.81(2H,d,J=8.9 Hz), 8.53(1H,s), 8.55(1H, brs). IR (KBr) cm$^{-1}$: 3324,1694,1622,1611,1591,1538, 1516,1253,1175,1033,836. Mass (m/z): 356 (M$^+$).

Example 126

Preparation of 2-cyclopropylmethyl-4-methanesulfonylamino-6-(4-methoxyphenyl)-2H-pyridazin-3-one (1) Preparation of 2-cyclopropylmethyl-4-dimethanesulfonylamino-6-(4-methoxyphenyl)-2H-pyridazin-3-one Using 4-amino-2-cyclopropylmethyl)-6-(4-methoxyphenyl)-2H-pyridazin-3-one as a starting material, the procedures of Examples 122-(1) were repeated likewise, whereby the title compound was obtained in a yield of 90.1%.

¹H-NMR (CDCl₃) δ: 0.43–0.63(4H,m), 1.33–1.49(1H, m), 3.57(6H,s), 3.87(3H,s), 4.13(2H,d,J=7.3 Hz), 6.99(2H, d,J=8.6 Hz), 7.71(2H,d,J=8.6 Hz), 7.72(1H,s).

(2) Preparation of 2-cyclopropylmethyl-4-methanesulfonylamino-6-(4-methoxyphenyl)-2H-pyridazin-3-one Using 2-cyclopropylmethyl-4-dimethanesulfonyl-amino-6-(4-methoxyphenyl)-2H-pyridazin-3-one as a starting material, the procedures of Examples 122-(2) were repeated likewise, whereby the title compound was obtained in a yield of 81.0%.

Colorless needles (chloroform-hexane)

Melting point: 203.3–203.9° C. ¹H-NMR (CDCl₃) δ: 0.45–0.63(4H,m), 1.35–1.50(1H,m), 3.16(3H,s), 3.87(3H,s), 4.12(2H,d,J=7.3 Hz), 6.98(2H,d,J=8.8 Hz), 7.74(1H,s), 7.75 (2H,d,J=8.8 Hz), 8.09(1H,br). IR (KBr) cm hu −1: 3124, 1641,1604,1583,1517,1448,1347,1253,1148,1025,864,833. Mass (m/z): 349 (M⁺)

Example 127

Preparation of 4-carbamoyl-6-(3-chloro-4-fluorophenyl)-2-cinnamyl-2H-pyridazin-3-one Using 6-(3-chloro-4-fluorophenyl)-2-cinnamyl-4-ethoxycarbonyl-2H-pyridazin-3-one as a starting material, the procedures of Example 38 were repeated likewise, whereby the title compound was obtained in a yield of 64.8%.

Pale yellow needles (methanol)

Melting point: 211.0–212.0° C. ¹H-NMR (DMSO-d₆) δ: 5.05(2H,d,J=5.9 Hz), 6.52(1H,td,J=5.9,15.8 Hz), 6.68(1H, d,J=15.8 Hz), 7.22–7.38(3H,m), 7.47(2H,d,J=6.9 Hz), 7.55 (1H,t,J=8.9 Hz), 7.95–8.02(1H,m), 7.08–8.20(2H,m), 8.29 (1H,s), 8.82(1H,brs). IR (KBr) cm⁻¹: 3306,3135,1705,1632, 1578,1506,1407,1266,959,816,801,735. Mass (m/z): 385 (M⁺), 383 (M⁺).

Example 128

Preparation of 4,5-dihydro-2-isobutyl-6-(4-methoxyphenyl)-4-methylcarbamoyl-2H-pyridazin-3-one To a solution of 2-isobutyl-6-(4-methoxyphenyl)-4-methylcarbamoyl-2H-pyridazin-3-one (50 mg, 0.16 mmol) in N,N-dimethylformamide (10 ml), 10% palladium on charcoal (45 mg) was added, followed by catalytic reduction at 80° C. Fourteen hours later, the catalyst was filtered off, the solvent was distilled off under reduced pressure, and the residue was separated and purified by silica gel preparative chromatography [developer: hexane/ethyl acetate (1/1)]. Crystallization was then conducted from chloroform-hexane, whereby the title compound (22 mg, 43.7%) was obtained as colorless needles.

Melting point: 124.2–125.0° C. ¹H-NMR (CDCl₃) δ: 0.926(3H,d,J=6.8 Hz), 0.932(3H,d,J=6.8 Hz), 2.07–2.24 (1H,m), 2.82(3H,d,J=4.6 Hz), 3.05–3.17(1H,m), 3.33–3.44 (2H,m), 3.65–3.70(2H,m), 3.85(3H,s), 6.93(2H,d,J=9.0 Hz), 7.36(1H,br), 8.24(2H,d,J=9.0 Hz). IR (KBr) cm⁻¹: 3392, 3015,1675,1646,1515,1405,1364,1256,1177,1026. Mass (m/z): 317 (M⁺).

Example 129

Preparation of 2-cyclopropylmethyl-6-(3-fluoro-4-methoxyphenyl)-4-methylthiocarbamoyl-2H-pyridazin-3-one To a solution of 2-cyclopropylmethyl-6-(3-fluoro-4-methoxyphenyl)-4-methylcarbamoyl-2H-pyridazin-3-one (133 mg, 0.40 mmol) in toluene (10 ml), Lawesson's reagent (162 mg, 0.40 mmol) was added, followed by stirring at 85° C. for 12 hours under argon. The toluene was distilled off, and the residue was separated and purified by chromatography on a silica gel column [silica gel: 6 g, hexane/ethyl acetate (4/1 to 2/1)]. Crystallization was conducted from chloroform-ethyl acetate, whereby the title compound (109 mg, 78.4%) was obtained as orange needles.

Melting point: 178.0–178.5° C. ¹H-NMR (CDCl₃) δ: 0.47–0.63(4H,m), 1.40–1.47(1H,m), 3.39(3H,d,J=4.9 Hz), 3.96(3H,s), 4.20(2H,d,J=7.3 Hz), 7.03–7.08(1H,m), 7.61–7.64(1H,m), 7.68–7.72(1H,m), 9.26(1H,s), 12.34(1H, br). IR (KBr) cm⁻¹: 3111,1641,1548,1521,1506,1425,1289, 1267,1117,1015. Mass (m/z): 347 (M⁺).

Example 130

Preparation of 2-isobutyl-6-(4-methoxyphenyl)-4-methylthiocarbamoyl-2H-pyridazin-3-one Using 2-isobutyl-6-(4-methoxyphenyl)-4-methylcarbamoyl-2H-pyridazin-3-one as a starting material, the procedures of Example 129 were repeated likewise, whereby the title compound was obtained in a yield of 27.7%.

Orange needles (ethyl acetate-diethyl ether)

Melting point: 116.0–116.6° C. ¹H-NMR (CDCl₃) δ: 1.00(6H,d,J=6.6 Hz), 2.36(1H,sept.,J=6.8 Hz), 3.38(3H,d,J= 4.9 Hz), 3.87(3H,s), 4.17(2H,d,J=7.3 Hz), 7.00(2H,d,J=8.8 Hz), 7.85(2H,d,J=9.0 Hz), 9.28(1H,s), 12.40(1H,br). IR (KBr) cm⁻¹: 2960,1640,1544,1515,1503,1266,1249. Mass (m/z): 331 (M⁺).

Test 1

(Inhibitory activity against interleukin-1β production)

HL-60 cells were cultured for 4 days until confluence on RPMI 1640 medium with 10% fetal bovine serum (FBS) added thereto. The medium was centrifuged. The supernatant was discarded, and the cells were then suspended at 1×10⁶ cells/me on RPMI 1640 medium with 3% FBS, and lipopolysaccharide was added to give a final concentration of 10 μg/ml. The culture was inoculated at 1 ml/well to a 24-well plate. A test compound was added at 1 μl/well, followed by culturing for 3 days. Three days later, the amount of interleukin-1β in each IC₅₀ value was determined by a comparison in yield with a control to which no test sample was added. Results on some representative compounds are shown in Table 1.

TABLE 1

| Inhibitory Activity against Interleukin-1β (IL-1β) Production | |
|---|---|
| Test compound (Example No.) | IL-1β IC₅₀ (μM) |
| 43 | 0.357 |
| 61 | 0.038 |
| 63 | 0.31 |
| 66 | 0.11 |
| 87 | 0.05 |
| 111 | 0.53 |
| 112 | 0.387 |
| 128 | 0.40 |
| Comp. Comp'd 1 | 29 |
| Comp. Comp'd 2 | 46 |
| Comp. Comp'd 3 | >100 |
| Comp. Comp'd 4 | 31.6 |

TABLE 1-continued

Inhibitory Activity against
Interleukin-1β (IL-1β) Production

| Test compound (Example No.) | IL-1β IC$_{50}$ (μM) |
|---|---|

(Comp. Comp'd 1)

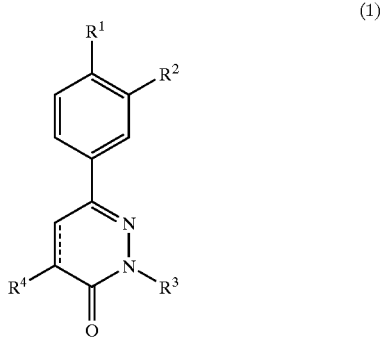

(Comp. Comd'd 2)

(Comp. Comd'd 3)

(Comp. Comd'd 4)

As is apparent from Table 1, the compounds according to the present invention have been found to have extremely good IL-1β inhibitory activity compared with the comparative compounds, which are the compounds disclosed in EOR. J. MED. CHEM., 14, 53–60, 1979 and are known to have anti-inflammatory and analgesic action.

Capability of Exploitation in Industry

The pyridazine derivatives (1) and their salts, which pertain to the present invention, have excellent inhibitory activity against interleukin-1β production, and are useful as medicines such as preventives and therapeutics for immune system diseases, inflammatory diseases and ischemic diseases.

What is claimed is:

1. A pyridazine derivative represented by the following formula (1):

$$(1)$$

wherein
$R^1$ represents a lower alkoxyl group, or a lower alkylthio group;
$R^2$ represents a hydrogen atom, a lower alkoxyl group, a lower alkylthio group or a halogen atom;
$R^3$ represents a linear or branched lower alkyl or lower alkenyl group, wherein said alkyl or alkenyl group may have one or more substituents each independently selected from the group consisting of a hydroxyl group, a halogen atom, a cyano group, a lower cycloalkyl group, a phenyl group which may be substituted, a naphthyl group which may be substituted, a pyridyl group which may be substituted, wherein said phenyl, naphthyl or pyridyl groups when substituted have 1 to 3 substituents independently selected from the group consisting of a halogen atom, a nitro group, an amino group, and a carbonylamino group substituted with a phenyl, naphthyl or pyridyl group; and a carbamoyl group that may be substituted with one or more substituents independently selected from the group consisting of a lower alkyl group, a lower alkyl group substituted by one or more hydroxy groups, a lower alkyl group substituted with phenyl, naphthyl or pyridyl, and a phenyl, naphthyl or pyridyl group which may be substituted with one or more lower alkythio groups;

$R^4$ represents a carboxyl group, a lower alkoxycarbonyl group, a carbamoyl group which may have one or more substituents each independently selected from a lower alkyl group, a phenyl, naphthyl or pyridyl group, or by a lower alkyl group substituted by one or more phenyl, naphthyl or pyridyl groups, a thiocarbamoyl group which may have one or more substituents each independently selected from a lower alkyl group, a phenyl, naphthyl or pyridyl group, or by a lower alkyl group substituted by one or more phenyl, naphthyl or pyridyl groups, a amino group which may have one or more substituents independently selected from a lower alkoxycarbonyl group which may be substituted by phenyl, naphthyl or pyridyl, a $C_1$–$C_5$ acyl group, a lower alkyl group which may be optionally substituted by phenyl, naphthyl or pyridyl, a lower alkylsulfonlyl group, or a ureido group, which may be substituted by one or more lower alkyl groups;

wherein the dashed line in formula I indicates that the carbon-carbon bond between the 4-position and the 5-position is a single bond or a double bond;

or a salt thereof.

2. A pyridazine derivative or a salt thereof according to claim 1, wherein the carbon-carbon bond between the 4-position and the 5-position in the formula (1) is a double bond.

3. A pyridazine derivative or a salt thereof according to claim 1, wherein $R^1$ represents a lower alkoxyl group or a lower alkylthio group; and $R^2$ represents a hydrogen atom, halogen atom or a lower alkoxyl group.

4. A pyridazine derivative or a salt thereof according to claim 1, wherein:

$R^3$ represents a linear or branched alkyl group having 1 to 6 carbon atoms or a linear or branched lower alkenyl group having 2 to 9 carbon atoms, wherein said alkyl or alkenyl groups may have one or more substituents each independently selected from the group consisting of:

a hydroxyl group, a halogen atom, a cyano group, a lower cycloalkyl group;

a phenyl or pyridyl group which may have 1 to 3 substituents each independently selected from a halogen atom, a nitro group, an amino group, a carbonylamino group substituted by one or more phenyl, naphthyl or pyridyl groups; and a carbamoyl group which may have one or more substituents each independently selected from a lower alkyl group, a hydroxy lower alkyl group, a lower alkyl group substituted by one or more phenyl, naphthyl or pyridyl groups or a lower alkylthiophenyl group; and $R^4$ represents a carboxyl group; a lower alkoxy-carbonyl group; a carbamoyl or thiocarbamoyl group which may have one or more substituents each independently selected from a lower alkyl group, a phenyl, naphthyl or pyridyl group or a lower alkyl group substituted by one or more phenyl, naphthyl or pyridyl groups; an amino group which may have one or more substituents each independently selected from a lower alkoxycarbonyl group, a lower alkoxycarbonyl group substituted by one or more phenyl, naphthyl or pyridyl groups, a $C_1$–$C_5$ acyl group, a lower alkyl group, a lower alkyl group substituted by one or more phenyl, naphthyl or pyridyl groups, a lower alkylsulfonyl group; or a ureido group which may have one or more lower alkyl groups as substituents.

5. A pyridazine derivative or a salt thereof that is 2-isobutyl-6-(4-methoxy-phenyl)-4-methylcarbamoyl-2H-pyridazin-3-one, 2-cyclo-propylmethyl-6-(4-methoxyphenyl)-4-methylcarbamoyl-2H-pyridazin-3-one, 2-cyclopropylmethyl-6-(3-fluoro-4-methoxyphenyl)-4-methylcarbamoyl-2H-pyridazin-3-one, 2-cyclopropylmethyl-4-ethylcarbamoyl-6-(4-methoxyphenyl)-2H-pyridazin-3-one, 2-(4-chlorocinnamyl)-4-ethoxycarbonylamino-6-(4-methoxyphenyl)-2H-pyridazin-3-one, or 2-(4-chlorocinnamyl)-4-formylamino-6-(4-methoxy-phenyl)-2H-pyridazin-3-one.

6. A pyridazine derivative or a salt thereof that is 6-(3-chloro-4-fluorophenyl)-2-cinnamyl-4-ethoxycarbonyl-2H-pyridazin-3-one or 4-carbamoyl-6-(3-chloro-4-fluorophenyl)-2-cinnamyl-2H-pyridazin-3-one.

7. A pharmaceutical composition or medicine comprising a pyridazine derivative or a salt thereof according to claim 1 and a pharmaceutically acceptable carrier.

8. A method for preparing a pharmaceutical composition or a medicine comprising admixing the pyridazine derivative or a salt thereof according to claim 1 with a pharmaceutically acceptable carrier.

9. A method for inhibiting interleukin-1β production comprising administering to a subject an effective amount of a pyridazine derivative or a salt thereof according to claim 1, wherein said subject has arthritis or rheumatism.

* * * * *

UNITED STATES PATENT AND TRADEMARK OFFICE
CERTIFICATE OF CORRECTION

PATENT NO.   : 6,403,586 B1
DATED        : June 11, 2002
INVENTOR(S)  : Masao Ohkuchi et al.

It is certified that error appears in the above-identified patent and that said Letters Patent is hereby corrected as shown below:

Column 50,
Line 63, the term "by" should be deleted.

Column 51,
Line 1, the term "by" should be deleted.

Signed and Sealed this

Tenth Day of December, 2002

JAMES E. ROGAN
*Director of the United States Patent and Trademark Office*